(12) United States Patent
Nguyen et al.

(10) Patent No.: US 8,932,398 B2
(45) Date of Patent: Jan. 13, 2015

(54) GALLOTANNIC COMPOUNDS FOR LITHOGRAPHIC PRINTING PLATE COATING COMPOSITIONS

(75) Inventors: My T Nguyen, Kirkland (CA); A Kha Phan, Travinh (VN); Quoc Khoi Nguyen, Travinh (VN); Marc-André Locas, Pierrefonds (CA)

(73) Assignee: Mylan Group, Travinh (VN)

( * ) Notice: Subject to any disclaimer, the term of this patent is extended or adjusted under 35 U.S.C. 154(b) by 177 days.

(21) Appl. No.: 13/390,285

(22) PCT Filed: Jun. 11, 2010

(86) PCT No.: PCT/CA2010/000862
§ 371 (c)(1),
(2), (4) Date: Feb. 13, 2012

(87) PCT Pub. No.: WO2011/050442
PCT Pub. Date: May 5, 2011

(65) Prior Publication Data
US 2012/0137929 A1    Jun. 7, 2012

Related U.S. Application Data

(60) Provisional application No. 61/255,918, filed on Oct. 29, 2009.

(51) Int. Cl.
| | | |
|---|---|---|
| *D21H 21/16* | (2006.01) |
| *C09B 67/00* | (2006.01) |
| *C04B 28/36* | (2006.01) |
| *B01F 17/00* | (2006.01) |
| *C01B 25/00* | (2006.01) |
| *G03F 7/038* | (2006.01) |
| *G03F 7/022* | (2006.01) |
| *G03F 7/027* | (2006.01) |
| *C07H 13/08* | (2006.01) |
| *B41C 1/10* | (2006.01) |
| *C07D 309/10* | (2006.01) |

(52) U.S. Cl.
CPC .............. *C07D 309/10* (2013.01); *G03F 7/038* (2013.01); *B41C 2210/08* (2013.01); *G03F 7/022* (2013.01); *B41C 2210/02* (2013.01); *G03F 7/027* (2013.01); *C07H 13/08* (2013.01); *B41C 1/1008* (2013.01); *B41C 2210/24* (2013.01); *B41C 2210/22* (2013.01); *B41C 2210/04* (2013.01)
USPC .............. 106/287.2; 106/287.21; 106/287.23; 106/287.24; 106/287.26

(58) Field of Classification Search
USPC ........ 106/287.2, 287, 287.21, 287.23, 287.26
See application file for complete search history.

(56) References Cited

U.S. PATENT DOCUMENTS

| | | |
|---|---|---|
| 3,600,166 A | 8/1971 | Sieg et al. |
| 3,862,842 A | 1/1975 | Bissonette |

(Continued)

FOREIGN PATENT DOCUMENTS

| | | |
|---|---|---|
| CA | 2015759 | 11/1990 |
| CN | 1057254 A | 12/1991 |

(Continued)

OTHER PUBLICATIONS

Extended European Search Report; EP10825873.2; Nov. 16, 2012.

(Continued)

*Primary Examiner* — James McDonough
(74) *Attorney, Agent, or Firm* — Lathrop & Gage LLP; Brian C. Trinque

(57) ABSTRACT

There is provided a gallotannic compound, a method of producing a gallotannic compound, a lithographic printing plate coating composition, a lithographic printing plate, a method of producing a lithographic printing plate and a method of printing.

19 Claims, 31 Drawing Sheets

(56) References Cited

U.S. PATENT DOCUMENTS

| | | | |
|---|---|---|---|
| 4,090,919 | A | 5/1978 | Chibata et al. |
| 4,565,769 | A | 1/1986 | Dueber et al. |
| 5,208,135 | A | 5/1993 | Patel et al. |
| 5,569,573 | A | 10/1996 | Takahashi et al. |
| 5,629,354 | A | 5/1997 | West et al. |
| 6,124,425 | A | 9/2000 | Nguyen |
| 6,177,182 | B1 | 1/2001 | Nguyen |
| 6,255,033 | B1 | 7/2001 | Levanon et al. |
| 6,261,740 | B1 | 7/2001 | Nguyen et al. |
| 6,420,087 | B1 | 7/2002 | Bennett et al. |
| 6,461,795 | B1 | 10/2002 | McCullough et al. |
| 6,506,536 | B2 | 1/2003 | Pappas et al. |
| 6,541,181 | B1 | 4/2003 | Levanon et al. |
| 6,562,543 | B2 | 5/2003 | Ogata et al. |
| 6,569,603 | B2 | 5/2003 | Furukawa |
| 6,582,882 | B2 | 6/2003 | Pappas et al. |
| 6,596,464 | B2 | 7/2003 | Van Damme et al. |
| 6,613,494 | B2 | 9/2003 | Savariar-Hauck et al. |
| 6,787,281 | B2 | 9/2004 | Tao et al. |
| 6,846,614 | B2 | 1/2005 | Timpe et al. |
| 6,899,994 | B2 | 5/2005 | Huang et al. |
| 6,902,860 | B2 | 6/2005 | Asawa et al. |
| 6,960,422 | B2 | 11/2005 | Goto |
| 6,969,575 | B2 | 11/2005 | Inno |
| 6,983,694 | B2 | 1/2006 | Vermeersch et al. |
| 7,001,704 | B2 | 2/2006 | Oshima et al. |
| 7,083,895 | B2 | 8/2006 | Hunter et al. |
| 7,135,271 | B2 | 11/2006 | Kawauchi et al. |
| 7,261,998 | B2 | 8/2007 | Hayashi et al. |
| 7,288,273 | B1 * | 10/2007 | Feldman ................ 424/776 |
| 7,473,515 | B2 | 1/2009 | Nguyen et al. |
| 7,544,462 | B2 | 6/2009 | Levanon et al. |
| 2002/0142244 | A1 | 10/2002 | Takashima et al. |
| 2003/0064318 | A1 | 4/2003 | Huang et al. |
| 2003/0170571 | A1 | 9/2003 | Nozaki et al. |
| 2003/0226462 | A1 | 12/2003 | Latunski et al. |
| 2005/0123853 | A1 | 6/2005 | Munnelly et al. |
| 2007/0269739 | A1 | 11/2007 | Nguyen et al. |
| 2007/0291077 | A1 | 12/2007 | Seki et al. |
| 2008/0070850 | A1 * | 3/2008 | Feldman ................ 514/35 |
| 2008/0171286 | A1 | 7/2008 | Nguyen et al. |
| 2009/0004599 | A1 | 1/2009 | Levanon et al. |
| 2009/0012088 | A1 * | 1/2009 | Hergenrother et al. .... 514/236.5 |
| 2009/0035694 | A1 | 2/2009 | Nguyen et al. |
| 2009/0111051 | A1 | 4/2009 | Tao et al. |
| 2009/0118202 | A1 * | 5/2009 | Thekkumkara ................ 514/25 |
| 2009/0186299 | A1 | 7/2009 | Tao et al. |

FOREIGN PATENT DOCUMENTS

| | | | |
|---|---|---|---|
| EA | 005106 | B1 | 10/2004 |
| EP | 0083971 | A2 | 7/1983 |
| EP | 0397009 | A2 | 11/1990 |
| EP | 0438123 | | 7/1991 |
| EP | 0626139 | A1 | 11/1994 |
| EP | 0770495 | | 5/1997 |
| EP | 0823327 | | 2/1998 |
| EP | 0909657 | | 4/1999 |
| EP | 1182033 | | 2/2002 |
| GB | 1399482 | A | 7/1975 |
| JP | 52091898 | A | 8/1977 |
| WO | WO 97/39894 | | 10/1997 |
| WO | WO 98/42507 | | 10/1998 |
| WO | WO 99/11458 | | 3/1999 |
| WO | WO 00/66705 | | 11/2000 |
| WO | WO 01/36436 | | 5/2001 |
| WO | WO01/85453 | A1 | 11/2001 |
| WO | WO 2004/009094 | A1 | 1/2004 |
| WO | WO 2004/020484 | | 3/2004 |
| WO | WO 2004/101280 | | 11/2004 |
| WO | WO 2008/058333 | A1 | 5/2008 |
| WO | WO 2008/156552 | | 12/2008 |

OTHER PUBLICATIONS

Barbehenn et al.; "Ellagitannins have Greater Oxidative Activities than Condensed Tannins and Galloyl Glucoses at High pH: Potential Impact on Caterpillars"; Journal of Chemical Ecology 2006, vol. 32, pp. 2253-2267.

Office Action for Korean Patent Application No. 10-2012-7007809 mailed Dec. 23, 2013 (7 pages total: 3 pages Office Action, 4 pages translation).

International Search Report for PCT/CA2010/000862 mailed Jul. 18, 2011.

Khanbabee, K. et al., "Tannins: Classification and Definition", Nat. Prod. Rep.18: pp. 641-649, 2001.

Fanwen, Z. Et al., "Dendrimers in Supramolecular Chemistry: From Molecular Recognition to Self-Assembly", Chem. Rev. 197: pp. 1684-1712, 1997.

Revised International Search Report, mailed Sep. 22, 2011.

* cited by examiner

GALLOTANNIC COMPOUNDS FOR LITHOGRAPHIC PRINTING PLATE COATING COMPOSITIONS

This application is the U.S. national phase of International Application No. PCT/CA2010/000862 filed 11 Jun. 2010 which designated the U.S. and claims priority to US Provisional Application No. 61/255,918 filed 29 Oct. 2009, the entire contents of each of which are hereby incorporated by reference.

FIELD OF THE INVENTION

The present invention relates to lithographic printing plates and their coatings. More specifically, the invention relates to gallotannin and gallotannic compounds and their use in coating compositions for lithographic printing plates.

BACKGROUND OF THE INVENTION

In lithographic printing, a printing plate is mounted on the cylinder of a printing press. The printing plate carries a lithographic image on its surface and a printed copy is obtained by applying ink to the image and then transferring the ink from the printing plate onto a receiver material, typically a sheet of paper. Generally, the ink is first transferred to an intermediate blanket, which in turn transfers the ink to the surface of the receiver material (offset printing).

In conventional, so-called "wet" lithographic printing, ink as well as an aqueous fountain solution (also called dampening liquid) are supplied to the lithographic image which consists of oleophilic (or hydrophobic, i.e. ink-accepting, water-repelling) areas as well as hydrophilic (or oleophobic, i.e. water-accepting, ink-repelling) areas. When the surface of the printing plate is moistened with water and ink is applied, the hydrophilic regions retain water and repel ink, and the ink-receptive regions accept ink and repel water. During printing, the ink is transferred to the surface of the receiver material upon which the image is to be reproduced.

Lithographic printing plates typically comprise an imageable layer (also called imaging layer or imaging coating) applied over the hydrophilic surface of a substrate, typically aluminium. The imageable layer includes one or more radiation-sensitive components, often dispersed in a suitable binder.

To produce the lithographic image on the printing plate, the printing plate is imaged by targeted radiation. This can be carried out in different ways. In direct digital imaging (computer-to-plate), printing plates can be imaged with infrared or UV lasers or light sources. Such a laser or light source can be digitally controlled via a computer; i.e. the laser can be turned on or off so that imagewise exposure of the precursor can be affected via stored digitized information in the computer. Therefore, the imageable layers of printing plates, which are to be imagewise exposed by means of such image-setters, need to be sensitive to radiation in the near-infrared region or UV of the spectrum.

The imaging device will thus etch the image on the printing plate by eliciting a localized transformation of the imageable layer. Indeed, in such systems, the imageable layer typically contains a dye or pigment that absorbs the incident radiation and the absorbed energy initiates the reaction producing the image. Exposure to the imaging radiation triggers a physical or chemical process in the imageable layer so that the imaged areas become different from the non-imaged areas and development will produce an image on the printing plate. The change in the imageable layer can be a change of hydrophilicity/oleophilicity, solubility, hardness, etc.

Following exposure, either the exposed regions or the unexposed regions of the imageable layer are removed by a suitable developer, revealing the underlying hydrophilic surface of the substrate. Developers are typically aqueous alkaline solutions, which may also contain organic solvents.

Alternatively, "on-press developable" lithographic printing plate can be directly mounted on a press after imaging, and are developed through contact with ink and/or fountain solution during initial press operation. In other words, either the exposed regions or the unexposed regions of the imageable layer are removed by the ink and/or fountain solution, not by a developer. More specifically, a so-called on-press development system is one in which an exposed printing plate is fixed on the plate cylinder of a printing press, and a fountain solution and ink are fed thereto while revolving the cylinder to remove the undesired areas. This technique allows an imaged, but un-developed printing plate (also called a printing plate precursor) to be mounted as is on a press and be made into a developed printing plate on an ordinary printing line.

If the exposed regions are removed, the precursor is positive-working. Conversely, if the unexposed regions are removed, the precursor is negative-working. In each instance, the regions of the imageable layer (i.e., the image areas) that remain are ink-receptive, and the regions of the hydrophilic surface revealed by the developing process accept water and aqueous solutions, typically a fountain solution, and do not accept ink.

On-press developable negative-working lithographic (offset) printing plates are known in the prior art.

For example, U.S. Pat. No. 5,569,573 teaches lithographic printing plates comprising a laser imaging layer containing microencapsulated oleophilic materials in hydrophilic polymer binders.

EP 0 770 495 teaches lithographic printing plates comprising near infrared absorption materials, polymer binders and thermoplastic particles capable of coalescing under heat.

U.S. Pat. No. 6,983,694 teaches on-press developable negative-working offset printing plates coated with near infrared sensitive coating compositions comprising thermoplastic polymer particles, such as polystyrene or poly(acrylonitrile-co-styrene) particles, non-reactive hydrophilic polymer binder and near infrared absorption dyes.

U.S. Pat. No. 6,261,740 teaches a non-process negative working laser imageable lithographic offset printing plate having radiation-sensitive composition coated on a hydrophilic substrate. The radiation-sensitive composition comprises copolymers having acid catalyzed pendant groups, which were polymerized from N-alkoxy methyl methacrylamide, and 3,4-epoxycyclohexyl methyl methacrylate. It further comprises phenolic binder resins, iodonium salt as acid generator, near infrared absorbing dye, visible dyes and film forming additives. Upon exposure to near infrared laser light, a crosslinking reaction occurs via cationic polymerization. The unexposed area could be developed on press with fountain solution.

Also, U.S. Pat. Nos. 6,124,425 and 6,177,182 teach on-press developable negative-working offset printing plates coated with thermally near-infrared absorbing polymers, which undergo crosslinking reactions via cationic polymerization upon exposure to near infrared radiation. The near infrared chromophoric moieties are functionalized to the polymeric backbone via ether and ammonium bonds.

U.S. Pat. No. 6,960,422 teaches negative-working offset printing plates containing a near infrared sensitive base-coat composition comprising molecular near infrared dyes, radical generators, radical polymerizable urethane compounds, reactive polymer binders and other additives.

Moreover, U.S. Pat. Nos. 6,969,575 and 7,001,704 teach on-press developable negative-working offset printing plates having an image-forming layer that comprises near infrared absorbing microcapsules and an acid generating compound.

U.S. Pat. Nos. 6,582,882, 6,846,614, and 6,899,994 and U.S. Patent application 2005/0123853 teach on-press developable negative-working offset printing plates coated with thermally imageable compositions containing polymer binders, initiator systems and polymerizable components. The described polymer binders are copolymers having non-reactive polyethylene oxide and polypropylene block, or graft copolymers having non-reactive polyethylene oxide side chains co-polymerized with acrylonitrile, styrene and other monomers. The polymerizable components are viscous liquid oligomers containing multiple acrylic functional groups. The initiator system contains near infrared absorption dyes and radical producing compounds, such as triazine and iodonium salts.

U.S. Pat. No. 7,261,998 teaches on-press or off-press developable negative-working offset printing plates comprising an image-forming layer, which comprises near infrared absorbing dyes having a tetraaryl pentadiene chromophore, a polymeric binder comprising a hydrophobic backbone to which poly(alkylene glycol) side chains are directly or indirectly linked, and free radical generating iodonium salt. The image-forming layer further comprises, as an adhesion promoter, a nonionic liquid phosphate acrylate having a molecular weight of at least 250.

U.S. Patent Application No. 2009/0186299 teaches a negative-working imaging coating composition that comprises an initiator element, a near infrared radiation absorbing compound, a polymeric binder and an adhesion promoter to increase the printing durability of the coating composition. The described adhesion promoters are liquid organic compounds having an ethylenically unsaturated carbon-carbon double bond that is connected to an alkoxysilyl or hydroxysilyl group, such as vinyltrimethoxysilane, vinylmethyldimethoxy-silane, vinyltriethoxysilane, vinyltris(2-methoxyethoxy)silane, vinyltriacetyloxy-silane, 3-acryloxypropyltrimethoxysilane, 3-methacryloxypropyltrimethoxy-silane, and 3-methacryloxypropylmethyldimethoxysilane.

U.S. Patent Application No. 2009/0111051 teaches a negative-working imaging coating composition including an initiator element, a near infrared radiation absorbing compound, a polymeric binder and a stabilizing composition. The stabilizing composition comprises liquid poly(ethylene glycol) diacid and free radical reactive compounds containing ureido terminated group, such as Sipomer WAM II from Rhodia (USA) and 1-[N-[poly(3-alkoxy-2-hydroxypropy)]-2-aminoethyl]-2-imidazolidinone from Aldrich Chemical Company (USA).

Positive working lithographic (offset) printing plates containing near infrared laser radiation sensitive polymeric coatings are also known in the prior art. See for example, WO 97/39894, EP 0 823 327, EP 0 909 657, WO 98/42507. These documents taught to prepare heat sensitive coatings comprising Novolak and (meth)acrylate type polymeric substances, near infrared absorbing compounds and dissolution inhibiting compounds. The near infrared absorbing and dissolution inhibiting compounds prevent the polymeric substance from dissolving in the liquid developer. This is due to the formation of a network structure via hydrogen bonding and/or ionic interactions within the coating composition. Upon imaging with near infrared laser light, this network structure within the exposed areas is disrupted and dissolves faster in the liquid developer compared to the non-exposed areas (image areas).

However, the solubility difference between the exposed and non-exposed areas may sometimes vary during storage and usage of the plate. Different approaches have been taught in the prior art toward overcoming the above problems.

For example, U.S. Pat. No. 6,461,795 teaches to treat the lithographic printing plates before shipping to the customers at a preferred temperature between 50 and 60° C. in low relative humidity for several hours to accelerate the formation of a stable network structure within the coating composition. This heat treatment process however increases the lithographic printing plates production cost and time.

U.S. Pat. No. 6,613,494 teaches to apply a thin over-layer to protect the non-exposed areas of the polymeric coating from attack by the liquid developer. Again, this approach increases the production cost and time of the lithographic printing plates.

U.S. Pat. No. 6,420,087 teaches to prepare coating compositions containing siloxane compounds as image protecting agent in order to reduce the dissolution of the non exposed areas during developing. The presence of these siloxane compounds caused however some phase separation in the coating solution making it difficult to coat this composition on substrates, for example with the roller coating techniques and pinhole. In addition, such siloxane compounds are not soluble in the alkaline developers. This causes sludge buildup in the processor and redeposit on the printing plates and shortens the lifetime of developer.

WO 2004/020484 teaches to prepare coating compositions consisting of acetal copolymers containing carboxylic acid, sulfonic acid and phosphoric acid terminated pendant groups, Novolak resin, near infrared absorption dyes, visible dye and image protecting agent for production of high chemical resistant thermally sensitive positive working lithographic offset printing plates. Such coating compositions require post heat treatment at 50° C. for one day in order to keep the image area from being attacked by the developer.

U.S. Pat. Nos. 6,255,033 and 6,541,181 teach to prepare and use acetal copolymers containing carboxylic acid, hydroxy, halide, methoxy, and acetylene functional groups as binder resins for production of positive-working lithographic offset printing plates that can be imaged with near infrared laser radiation. Such coating compositions require an adhesive promotion agent and a near infrared absorbing dye as dissolution inhibitor. In practice, high loading levels of near infrared dye and visible dye are used to differentiate between exposed and non-exposed areas during development. Moreover, the presence of such small organic molecules in the coating compositions might cause phase separation during coating. It also reduces the mechanical strength and causes blooming during storage.

U.S. Pat. Nos. 6,124,425 and 6,177,182 teach to prepare heat sensitive polymeric coating compositions for positive-working lithographic printing plates comprising near infrared absorbing chromophores grafted on the backbone of Novolak, acrylate and methacrylate based polymers. Optionally, the coating compositions may contain other binder resins and film-forming additives. The use of near infrared absorbing polymers in the thermally sensitive polymeric coating compositions exhibited several advantages, such as quick formation of stable network structure, good resistance of the non-exposed area to attack by the liquid developer without the need for a heat treatment or a protective over-layer.

U.S. Pat. No. 7,473,515 teaches to prepare heat sensitive polymeric coating compositions for positive-working lithographic printing plates comprising near infrared absorbing chromophores grafted on the backbone of acetal co-polymers. Optionally, the coating compositions may contain Novolak binder resins, colorants and film-forming additives.

U.S. Pat. No. 7,544,462 teaches to prepare heat sensitive polymeric coating compositions for positive-working lithographic printing plates comprising phenolic or acetal polymer binder resins, near infrared absorbing dyes and low molecular development enhancing compounds, such as dialkylamino benzoic acid.

U.S. 2009/0004599 teaches to prepare heat sensitive polymeric coating compositions for positive-working lithographic printing plates comprising acetal polymer having cyclic-ester pendant groups to improve resistance to press chemicals, such as alcohol substituted fountain solutions, UV wash solutions and UV inks.

WO 99/11458 also teaches about positive-working lithographic offset printing plates.

Despite all these advances in the art, there remains a need for new materials and new coatings for lithographic printing plates.

SUMMARY OF THE INVENTION

In accordance with the present invention, there are provided:

Item 1. A gallotannic compound comprising gallotannin wherein at least one hydroxyl group is replaced by a substituent.

Item 2. The gallotannic compound of item 1 having a molecular weight greater than 1701 g/mol.

Item 3. The gallotannic compound of item 1 or 2, wherein more than one hydroxyl group of gallotannin is replaced by said substituents, wherein the substituents replacing each of the hydroxyl groups are the same or different from each other.

Item 4. The gallotannic compound of any one of items 1 to 3, wherein the substituent(s) is/are attached directly to the gallotannin.

Item 5. The gallotannic compound of any one of items 1 to 3, wherein the substituent(s) is/are attached to the gallotannin through a linking group.

Item 6. The gallotannic compound of item 5, wherein the linking group is alkyl optionally comprising one or more ester, ether, amine, amido, urea, carbamate, sulfonamide, or

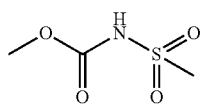

functional group.

Item 7. The gallotannic compound of any one of items 1 or 6, wherein the substituent(s) comprise(s) a molecule, oligomer or polymer used in lithographic printing plate coatings, gallotannin or another gallotannic compound.

Item 8. The gallotannic compound of any one of items 1 to 7, wherein the substituent(s) comprise(s):
  a) a crosslinker,
  b) an initiator,
  c) an adhesion promoter,
  d) a hydrogen bonding promoter,
  e) a chromophore,
  f) a binder,
  g) any other molecule, oligomer, or polymer used in lithographic printing plate coatings,
  h) gallotannin, or
  i) another gallotannic compound.

Item 9. The gallotannic compound of any one of items 1 to 8, wherein the gallotannic compound is of formula

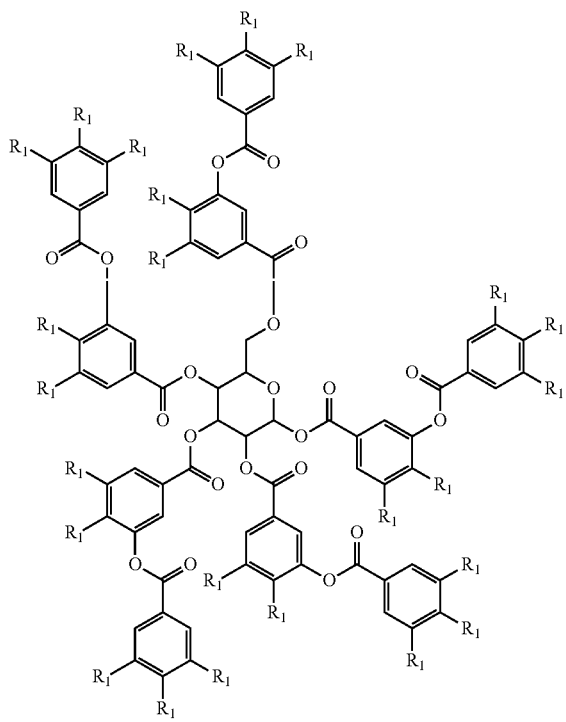

wherein each $R_1$ independently is hydroxyl or comprises one or more of:
  a) a crosslinker,
  b) an initiator,
  c) an adhesion promoter,
  d) a hydrogen bonding promoter,
  e) a chromophore, and
  f) a binder,
  g) any other molecule, oligomer, or polymer used in lithographic printing plate coatings,
  h) gallotannin, or
  i) another gallotannic compound,
and optionally comprises a linking group,
with the proviso that at least one $R_1$ is not hydroxyl.

Item 10. The gallotannic compound of item 8 or 9, wherein the crosslinker comprises a functional group capable of undergoing a crosslinking reaction via radical polymerization.

Item 11. The gallotannic compound of item 10, wherein the functional group capable of undergoing a crosslinking reaction via radical polymerization is acrylate, methacrylate, acrylamide, methacrylamide, alkylacrylate, alkylmethacrylate, alkylacrylamide, alkylmethacrylamide, vinyl ether, allyl, or styryl, Item 12. The gallotannic compound of item 8 or 9, wherein the crosslinker comprises functional group capable of undergoing a crosslinking reaction via cationic polymerization.

Item 13. The gallotannic compound of item 12, wherein the functional group capable of undergoing a crosslinking reaction via cationic polymerization is N alkoxymethylamido, N hydroxymethylamido, N-alkoxymethylacrylamide, N-alkoxymethylmethacrylamide, hydroxyalkyl, epoxy, or oxetane.

Item 14. The gallotannic compound of item 8 or 9, wherein the hydrogen bonding promoter comprises one or more alkyl and/or aryl, and wherein the alkyl and/or aryl comprises one or more functional groups capable of forming hydrogen bonds, the alkyl and/or aryl being optionally substituted by alkyl, aryl, alkyl aryl and/or poly(alkylene glycol).

Item 15. The gallotannic compound of item 7, wherein the lithographic printing plate coating is an imaging coating.

Item 16. The gallotannic compound of item 15, wherein the imaging coating is negative-working.

Item 17. The gallotannic compound of item 15, wherein the imaging coating is positive-working.

Item 18. The gallotannic compound of any one of items 15 to 17, wherein the imaging coating is NIR sensitive.

Item 19. The gallotannic compound of any one of items 15 to 17, wherein the imaging coating is UV sensitive.

Item 20. A method of producing a gallotannic compound, the method comprising the step of:
a) providing gallotannin; and
b) replacing at least one hydroxyl group of the gallotannin with a substituent, wherein the substituent is as described in any one of items 1 to 19.

Item 21. A printing plate coating composition comprising gallotannin and/or the gallotannic compound of any one of items 1 to 18.

Item 22. The coating composition of item 21 wherein said coating composition comprises at least 1.0 w/w % of gallotannin.

Item 23. The coating composition of item 21 wherein said coating composition comprises said gallotannic compound.

Item 24. The coating composition of item 23 wherein said coating composition comprises between about 1 and about 40 w/w % of said gallotannic compound.

Item 25. The coating composition of any one of items 21 to 24, wherein the coating composition is a negative-working imaging coating composition.

Item 26. The coating composition of any one of items 21 to 24, wherein the coating composition is a positive-working imaging coating composition.

Item 27. A lithographic printing plate comprising a coating produced using the coating composition of any one of items 21 to 26.

Item 28. A method of producing a lithographic printing plate, the method comprising the steps of:
a) providing a substrate, and
b) coating the coating composition of any one of items 21 to 26 onto the substrate.

Item 29. A method of printing, the method comprising the steps of:
a) providing a lithographic printing plate as defined in item 27,
b) imaging the printing plate with imaging radiation,
c) developing the imaged printing plate, and
d) using the developed printing plate on a printing press to print.

DETAILED DESCRIPTION OF THE INVENTION

Gallotannic Compound

Figure 1:
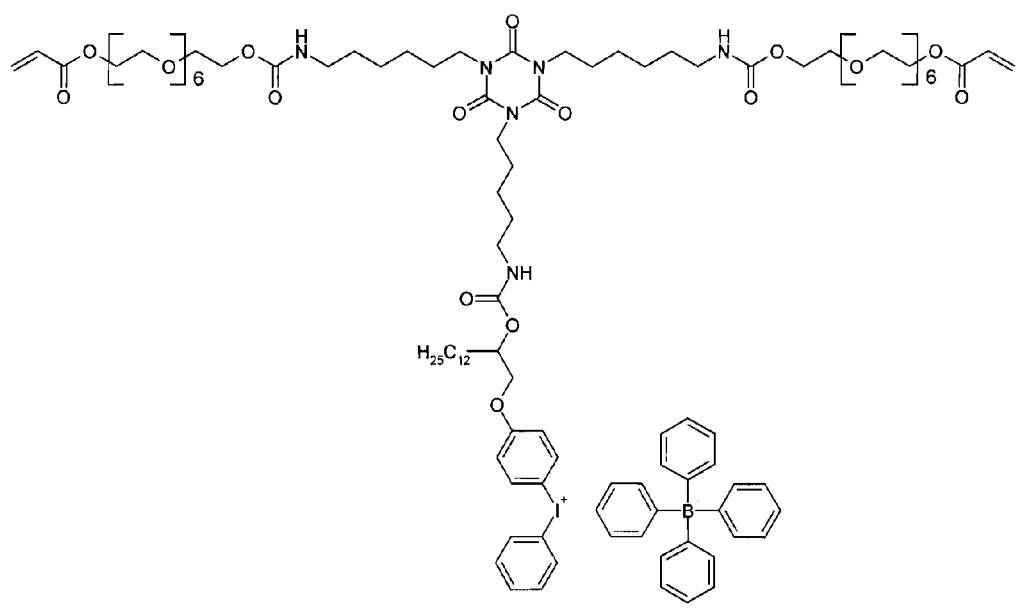
FIG. 1(a) to (f) show the reactive iodonium oligomers comprised in Tuxedo® 600 PFB commercially available from American Dye Source, Inc.
Figure 1:
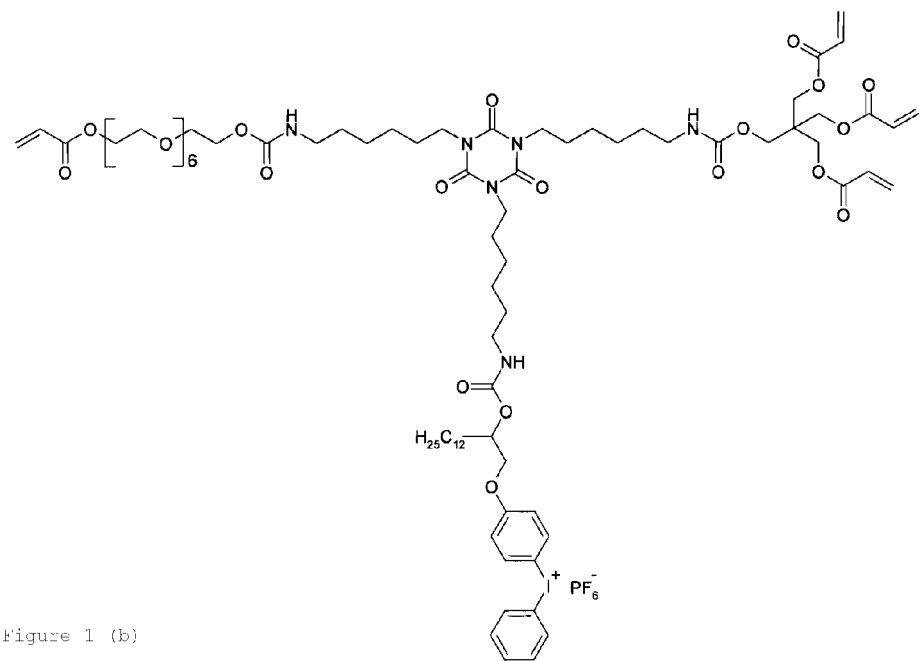
Figure 1:
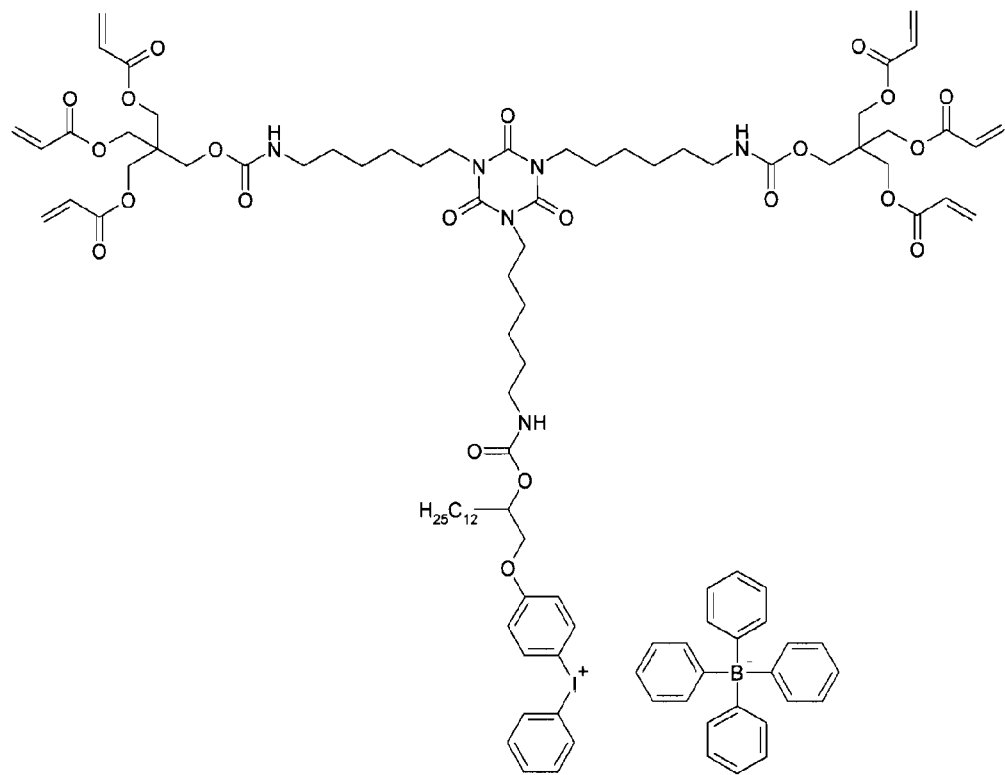
Figure 1:
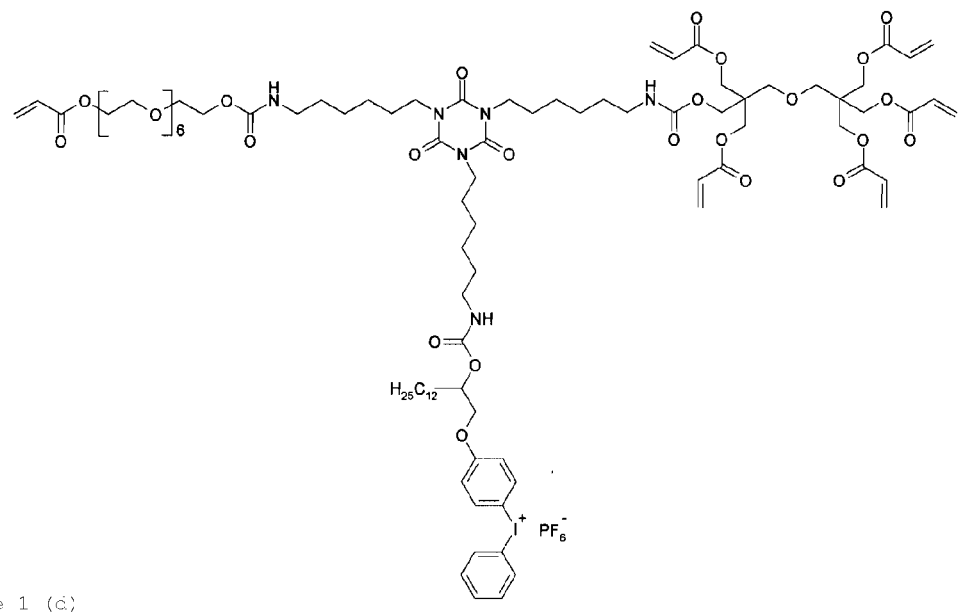
Figure 1:
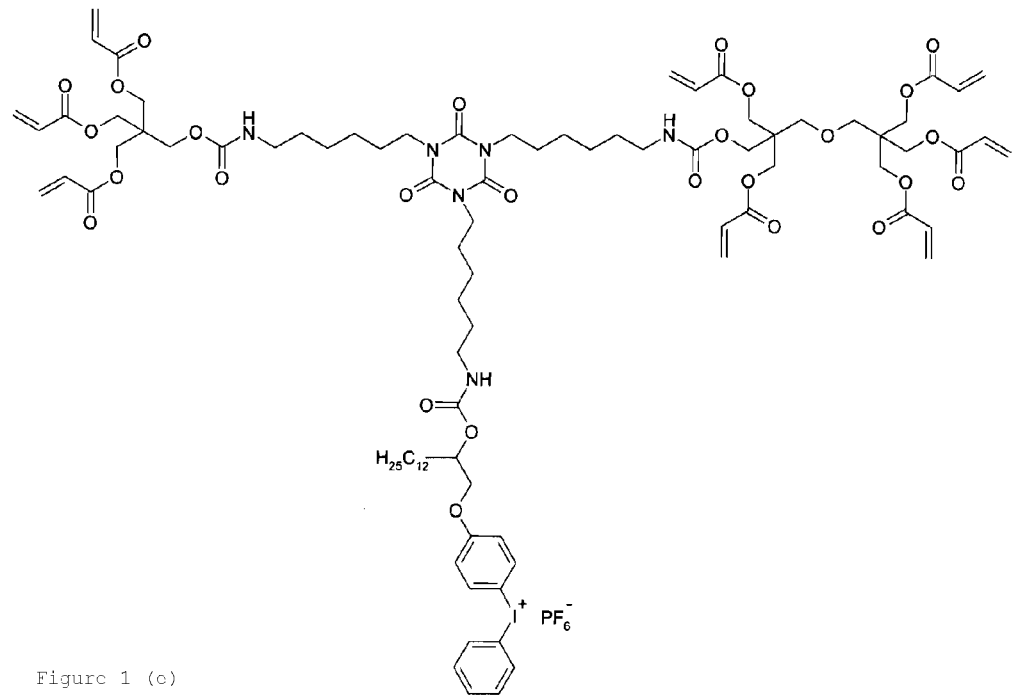
Figure 1:
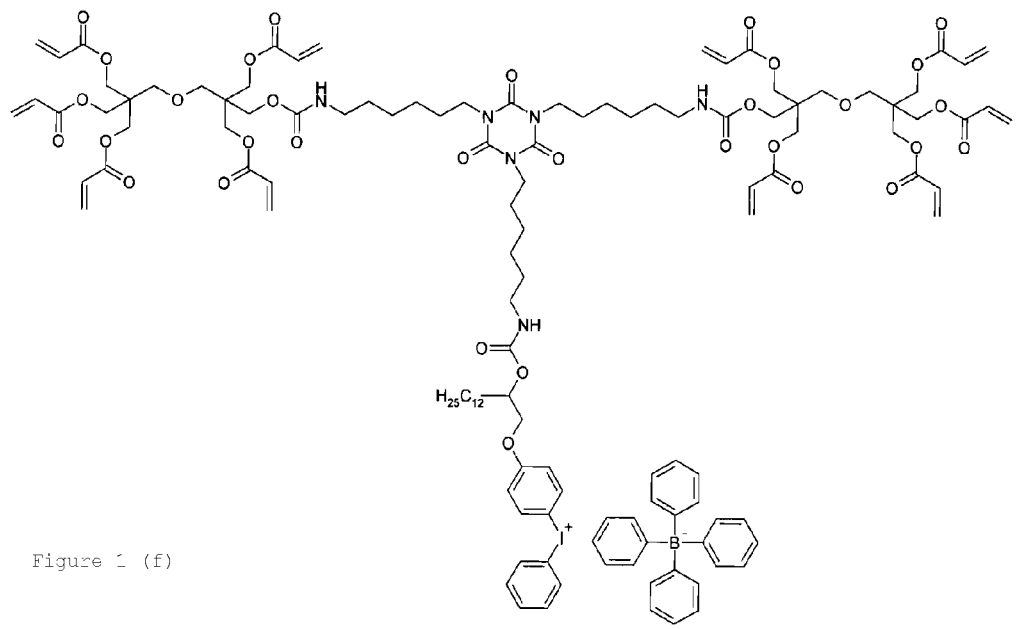

Turning now to the present invention in more details, there is provided, in a first aspect, a gallotannic compound comprising gallotannin wherein at least one hydroxyl group is replaced by a substituent.

Gallotannin, also known as tannic acid, is a solid material highly soluble in water. It is a polyphenol extracted from plants and has the following ideal structure based on glucose ester of gallic acid:

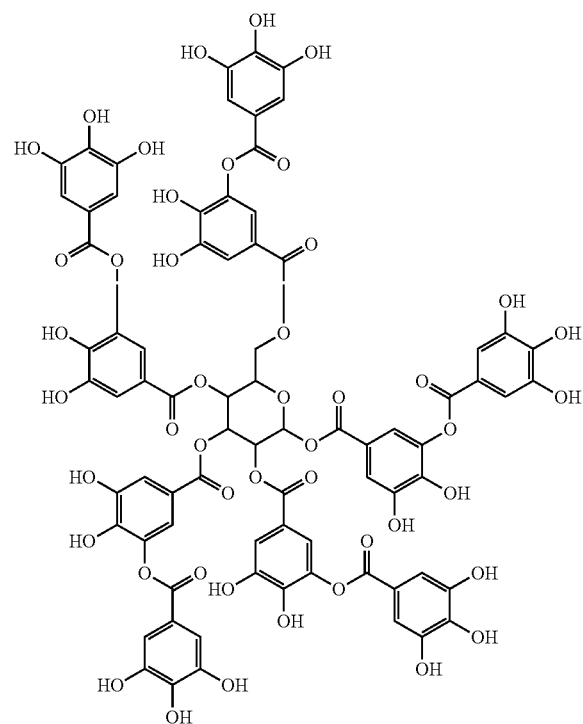 [SMILES: O=C(OCC1OC(OC(=O)c2cc(O)c(O)c(OC(=O)c3cc(O)c(O)c(O)c3)c2)C(OC(=O)c2cc(O)c(O)c(OC(=O)c3cc(O)c(O)c(O)c3)c2)C(OC(=O)c2cc(O)c(O)c(OC(=O)c3cc(O)c(O)c(O)c3)c2)C1OC(=O)c1cc(O)c(O)c(OC(=O)c2cc(O)c(O)c(O)c2)c1)c1cc(O)c(O)c(OC(=O)c2cc(O)c(O)c(O)c2)c1]

As can be seen above, gallotannin comprises several hydroxyl functional groups. These hydroxyl groups can be partially or completely replaced with different substituents.

The inventors have surprisingly found that gallotannin or gallotannic compounds in which at least one of the hydroxyl groups is replaced by another substituent are useful in lithographic printing plate coatings. It has indeed been surprisingly found that gallotannin and such gallotannic compounds generally promote adhesion of the coating to the substrate, which allows longer run length compared to similar coatings without gallotannin or such gallotannic compounds. More specifically, as can be seen in the Examples below, it has been found that gallotannin and gallotannic compounds are useful in coatings for printing plates as they tend to improve the adhesion of the radiation-sensitive coating to the substrate. The inventors have observed that a few weight % of gallotannin or such gallotannic compounds added to a known coating are typically sufficient to improve properties of the coating, such as its adhesion and run length properties.

In fact, it has been discovered by the present inventors that virtually all molecules, oligomers or polymers used in lithographic printing plate coatings can be attached to gallotannin so as to benefit from the advantageous effect of gallotannic compounds as illustrated in the Examples below. The molecules, oligomers or polymers may be those used in any coatings for lithographic printing plates, i.e. under-coatings, imaging coatings, over-coatings, etc. In embodiment, the substituents may be molecules, oligomers or polymers used in imaging coatings. More specifically, the imaging coating may be negative-working. In other embodiments, it is positive-working. In embodiments, the imaging coating is NIR sensitive. In other embodiments, the imaging coating is UV sensitive.

Non-limiting examples of substituents that can replace the hydroxyl groups of gallotannin in the gallotannic compound include substituents comprising:

crosslinkers, initiators, adhesion promoters, hydrogen bonding promoters, chromophores, binders, any other molecule, oligomer, or polymer used in lithographic printing plate coatings, gallotannin, and another gallotannic compound.

Of course, several hydroxyl groups of gallotannin may be replaced to produce the gallotannic compound. There is no need that all the hydroxyl groups be replaced by the same type of substituents. There is no need that all the substituents of a particular type be the same.

As stated above, the substituent may be gallotannin or another gallotannic compound. The inventors have indeed found that several gallotannin molecules or gallotannic compounds as described herein can be attached together to form dendrimers. These dendrimers show the herein described beneficial effect when used in printing plates. In embodiments, these dendrimers comprise from 2 to 25 gallotannin nucleuses.

The skilled person will appreciate that some of the above substituents are useful in negative plate, positive plates, or both types of plates. Therefore, the skilled person will know how to mix and match these substituents to obtain the desired effect.

Gallotannin has a molecular weight of 1701.22 g/mol. As such, in embodiments, the gallotannic compounds of the invention have a molecular weight greater than that, for example about 1702 g/mol or more. In embodiments, the gallotannic compound has a molecular weight of 2000, 2500, 3000, 3500 g/mol or more. The molecular can also be much higher than that, for example, in cases where one of the substituents is a polymer and in the case of dendrimers.

The skilled person will appreciate that the substituents [be they crosslinkers, initiators, adhesion promoters, hydrogen bonding promoters, chromophores, and binders (as well as, in the case of dendrimers, the other gallotannin molecules or gallotannic compounds)] can be attached directly to the gallotannin. Alternatively, the substituent(s) is/are attached to the gallotannin through a linking group. The nature of this linking group will be chosen to avoid interfering with the function of the groups it links to the gallotannin and for its ease of use in the synthesis of the gallotannic compound, however its exact nature is not crucial.

In embodiments, the linking group may be alkyl optionally comprising one or more ester, ether, amine, amido, urea, carbamate, sulfonamide, or

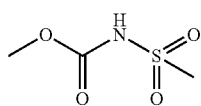

functional group (or any combination thereof). The alkyl may be linear, branched and/or cyclic. In other words, the alkyl may comprise linear parts, branched parts and cyclic parts at the same time. The alkyl group may have 1 to 50 carbon atoms. In the above, when it is said that the alkyl optionally comprises the listed functional groups, it means that the functional groups may be at end either of the alkyl or in between any two carbon atoms of the alkyl or its substituents. For more certainty, when more than one functional group is comprised in an alkyl, the functional groups do not need to be separated by carbons atoms of the alkyl; i.e. they may be directly attached to one another. For more certainty, herein an ether functional group is —O—; an ester functional group (or linker) is —(C=O)—O— or —O—(C=O)—; an amine functional group is —NR$_3$—, an amide (or amido) functional group (or linker) is —(C=O)—NR$_3$— or —NR$_3$—(C=O)—; an urea functional group is —NR$_3$—(C=O)—NR$_3$—; a sulfonamide functional group is —SO$_2$—NR$_3$— or —NR$_3$—SO$_2$—; and a carbamate functional group is —NR$_3$—(C=O)—O— or —O—(C=O)—NR$_3$—, R$_3$ being hydrogen or alkyl.

More specifically, in embodiments, there is provided a gallotannic compound of formula:

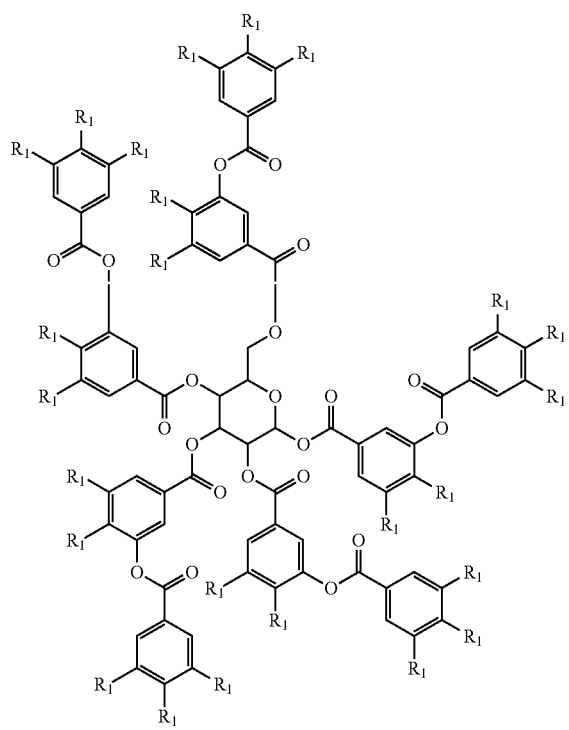

wherein each R$_1$ independently is hydroxyl or comprises one or more of:
   a crosslinker,
   an initiator,
   an adhesion promoter,
   a hydrogen bonding promoter,
   a chromophore,
   a binder,
   any other molecule, oligomer, or polymer used in lithographic printing plate coatings,
   gallotannin, or
   another gallotannic compound,
and optionally comprises a linking group,
with the proviso that at least one R$_1$ is not hydroxyl.

In embodiments, the crosslinker, initiator, adhesion promoter, hydrogen bonding promoter, chromophore, and binder are as described below.

Crosslinkers

As used herein, a "crosslinker" is a molecule, an oligomer or a polymer that comprises a functional group capable of undergoing a crosslinking reaction via cationic or radical polymerization. Herein, a functional group "capable of undergoing a crosslinking reaction via radical polymerization" means that the functional group is capable of reacting with another such functional group on the same or on a different molecule via free radical polymerization to form a 3D crosslinked network. As used herein, a functional group "capable of undergoing a crosslinking reaction via cationic polymerization" means that the functional group is capable of forming a covalent bond with another such functional group on the same or on a different molecule in the presence of an acid catalyst to form a 3D crosslinked network.

The purpose of the crosslinkers is to polymerize upon exposure to radical and/or acid. Such radicals and/or acid are generally produced by an initiator upon exposure to imaging radiation. The polymerization of the crosslinkers will produce a network in the imaged areas of the printing plates, thereby allowing developing the plates and printing with the plates. Functional groups capable of undergoing a crosslinking reaction via cationic or radical polymerization are well-known to the skilled persons. It will be clear to the skilled person that the exact nature of the crosslinkers is not crucial. The coupling of the crosslinkers with the gallotannin allows forming the desired network in the image areas and benefiting of the advantages of using gallotannin or a gallotannic compound as described above. According to the invention, any crosslinker comprising such functional group (with of without linking group) can replace one or more hydroxyl group of gallotannin.

In embodiments, the functional group capable of undergoing a crosslinking reaction via cationic or radical polymerization is a functional group capable of undergoing a crosslinking reaction via radical polymerization, e.g. a functional group that comprises a polymerizable carbon-carbon double bond (C=C). This functional group may be acrylate, methacrylate, acrylamide, methacrylamide, alkylacrylate, alkylmethacrylate, alkylacrylamide, alkylmethacrylamide, vinyl ether, allyl, or styryl, wherein, in embodiment, the alkyl has between 2 and 10 carbon atoms.

In embodiments, the functional group capable of undergoing a crosslinking reaction via cationic or radical polymerization is a functional group capable of undergoing a crosslinking reaction via cationic polymerization. This functional group may be N-alkoxymethylamido (such as N-methoxymethylamido), N-hydroxymethylamido, N-alkoxymethylacrylamide (such as N-methoxymethylacrylamide), N-alkoxymethylmethacrylamide (such as N-methoxymethylmethacrylamide), hydroxyalkyl, epoxy, or oxetane, wherein, in embodiments, alkyl has between 2 and 20 carbon atoms and/or alkoxy has between about 1 and 6 carbon atoms.

In embodiments, the crosslinker may be that described in U.S. Pat. Nos. 5,569,573 6,261,740, 6,960,422, 6,969,575, 6,846,614, 6,899,994, U.S. 2005/0123853, U.S. Pat. No. 7,261,998, or U.S. 2009/0186299, which are incorporated herein by reference.

It is to be noted that when a greater number of hydroxyl groups are replaced by crosslinkers, the imaging speed of the printing plate is increased due to greater availability of reactive sites. However, in some cases, the shelf-life of the plate may be somewhat reduced. Given the above, the skilled person will know how to balance these two effects to obtain a printing plate appropriate for his/her needs.

Initiators

Initiators are molecules, oligomers, or polymers used in printing plates for generating radicals and/or acid when the printing plate is exposed to imaging radiation. The purpose of the initiators is to generate radicals and/or acid upon exposure to imaging radiation or upon receiving electrons (donated for example by a chromophore). These radicals and/or acid will allow the polymerization of the crosslinkers which will produce a network in the imaged areas of the printing plates as described above, thereby allowing developing the plates and printing with the plates. Initiators are well-known by the skilled persons. It will be clear to the skilled person that the exact nature of the initiators is not crucial. The coupling of the initiators with the gallotannin allows generating radicals and/or acid in the image areas and benefiting of the advantages of using gallotannin or a gallotannic compound as described above. According to the invention, any initiator known to the skilled person can replace one or more hydroxyl group of gallotannin.

Such initiator may thus be sensitive to the imaging radiation to be used to image the printing plate. For use in a thermal (i.e. NIR sensitive) printing plate, an initiator sensitive to radiation in the near infrared (NIR) range of wavelength between 700 and 1100 nm may be used. Similarly, for use in an UV sensitive printing plate, an initiator sensitive to radiation in the ultraviolet (UV) range of wavelength between 300 and 450 nm may be used. It is to be noted that some initiators (or classes thereof) may be sensitive to both NIR and UV radiation.

In general, suitable initiators include but are not limited to, amines (such as alkanol amines), thiol compounds, anilinodiacetic acids or derivatives thereof, N-phenyl glycine and derivatives thereof, N,N-dialkylaminobenzoic acid esters, N-arylglycines and derivatives thereof (such as N-phenylglycine), aromatic sulfonylhalides, trihalogenomethylsulfones, imides (such as N-benzoyloxyphthalimide), diazosulfonates, 9,10-dihydroanthracene derivatives, N-aryl, S-aryl, or O-aryl polycarboxylic acids with at least 2 carboxy groups of which at least one is bonded to the nitrogen, oxygen, or sulfur atom of the aryl moiety (such as aniline diacetic acid and derivatives thereof and other "co-initiators" described in U.S. Pat. No. 5,629,354), oxime ethers and oxime esters (such as those derived from benzoin), α-hydroxy or α-amino-acetophenones, alkyltriarylborates, trihalogenomethylarylsulfones, benzoin ethers and esters, peroxides (such as benzoyl peroxide), hydroperoxides (such as cumyl hydroperoxide), azo compounds (such as azo bis-isobutyronitrile), 2,4,5-triarylimidazolyl dimers (also known as hexaarylbiimidazoles, or "HABI's") as described for example in U.S. Pat. No. 4,565,769, borate and organoborate salts such as those described in U.S. Pat. No. 6,562,543, and onium salts (such as ammonium salts, diaryliodonium salts, triarylsulfonium salts, aryldiazonium salts, and N-alkoxypyridinium salts). Other known initiator composition components are described for example in U.S Patent Application Publication 2003/0064318.

NIR and UV sensitive initiators also include diaryl iodonium salts, which are comprised of a positively charged iodine atom to which 2 aryl ring are attached and of a negatively charged counter ion. The negatively charged counter ions may be hexafluoro antimontate, tetraphenyl borate, triphenyl alkyl borate (wherein, in embodiments, alkyl has between 1 and 12 carbon atoms), tetrafluoro borate, hexafluoro phosphate, and tosylate.

The NIR sensitive initiators may also be, for example, the reactive oligomers described in U.S. Patent Application Nos. 2007/0269739, 2008/0171286 and 2009/0035694, which are incorporated herein by reference. Notably, these NIR sensitive initiators can also be used as UV sensitive initiators as they are sensitive to UV radiation.

In embodiments, the initiator may be that described in U.S. Pat. Nos. 5,569,573, 6,261,740, 6,960,422, 6,969,575, 6,846,614, 6,899,994, U.S. 2005/0123853, U.S. Pat. No. 7,261,998, U.S. 2009/0186299, U.S. 2009/0111051, and WO 2008/156552, which are incorporated herein by reference.

Also, the NIR sensitive initiators may be that commercially available from American Dye Source, Inc. (Baie d'Urfe, Quebec, Canada) under trade name Tuxedo® 600 PFB. This product is a mixture of the reactive iodonium oligomers shown in FIG. 1(a) to (f).

The NIR and UV sensitive initiators may be, for example, acid generating diazo compounds and polymers. These may be the following compound and polymers, which are commercially available from PCAS (France):

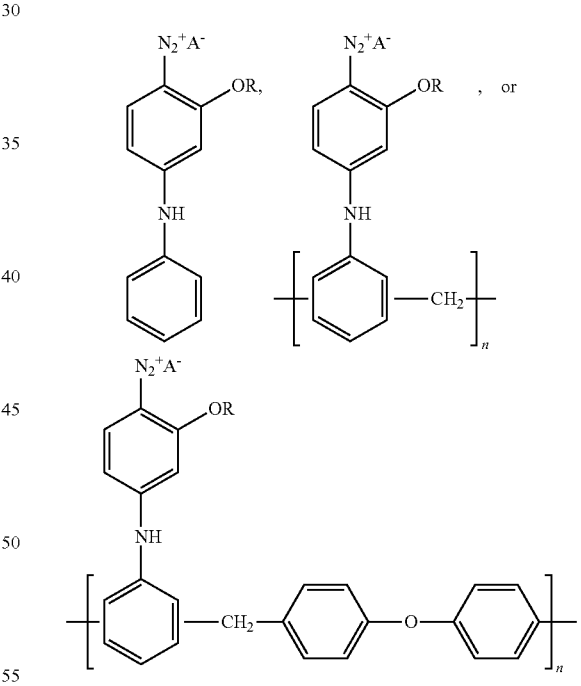

wherein:

A represents $PF_6$, $SbF_6$, aryl sulfonate, alkyl sulfonate and $BF_4$,

R represents linear or branched alkyl or poly(alkylene glycol), and n represents a number of repeating unit between 1 and 50, and wherein, in embodiments, the alkyl has between 1 and 5 carbon atoms and the poly(alkylene glycol) has between 1 and 50 repeat units.

In embodiments, the NIR and UV sensitive initiators may also be, for example, free radical generating triazine compounds. These may be the following compounds, which are also commercially available from PCAS (France):

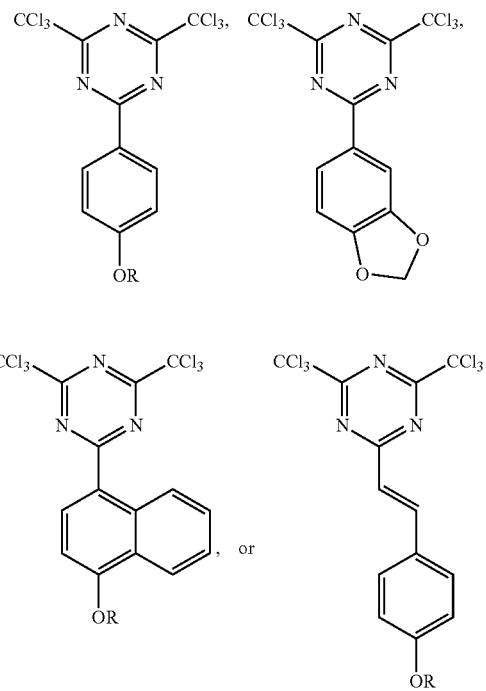

wherein R represents linear or branched alkyl or poly(alkylene glycol),
and wherein, in embodiments, the alkyl and/or alkylene has between 1 and 10 carbon atoms and poly(alkylene glycol) has between 1 and 50 repeat unit.

UV sensitive initiators also include triazine-based initiators.

Adhesion Promoters

Adhesion promoters are molecules, oligomers, or polymers used in printing plate to improve adhesion of a coating on a substrate.

The purpose of the adhesion promoter is to cause the imaging coating to better adhere to the substrate of the printing plate, thereby allowing longer press run with the plates. Adhesion promoters are well-known to persons of skill in the art. It will be clear to the skilled person that the exact nature of the adhesion promoters is not crucial. The coupling of the adhesion promoters with the gallotannin allows better adhesion while benefiting of the advantages of using gallotannin or a gallotannic compound as described above. According to the invention, any adhesion promoter known to the skilled person can replace one or more hydroxyl group of gallotannin.

In embodiments, the adhesion promoter may be that described in U.S. Pat. No. 7,083,895, which is incorporated herein by reference.

Typically, adhesion promoters comprise adhesion promoting functional groups such as cyano, ureido [i.e. $NH_2$—(C=O)—NH—] or phosphoric acid.

In embodiments, the adhesion promoter may be that described in U.S. 2009/0186299, U.S. Pat. Nos. 6,255,033, 6,541,181, WO 2008/156552, and U.S. 2007/0808434, which are incorporated herein by reference.

Hydrogen Bonding Promoters

The gallotannic compound may comprise hydrogen bonding promoters. These substituents are molecules, oligomers or polymers that comprise one or more functional groups capable of forming hydrogen bonds. In embodiments, these substituents comprise multiple functional groups capable of forming hydrogen bonds.

The purpose of the hydrogen bonding promoters is to form hydrogen bonds with other hydrogen bonding promoters and optionally other molecules present that have functional groups capable of forming hydrogen bonds. This allows the formation of a supramolecular structure in the coating. In negative-working plates, this improves the cohesion of the film. In positive-working plates, this also promotes cohesion and promotes the creation of a supramolecular structure (which may be disrupted upon imaging) thereby creating a stronger printing image (in the non-imaged areas).

Hydrogen bonding promoters are well-known to persons of skill in the art. They are often referred to "dissolution inhibitors" in positive printing plates of the prior art.

Functional groups capable of forming hydrogen bonds are also well known to the skilled person and include groups containing a hydrogen atom in a polar covalent bond and groups containing an electronegative atom with a pair of free electrons. Non limiting examples of such groups include hydroxy, carboxy, primary and secondary amines among others and any combination thereof. It will be clear to the skilled person that the exact nature of the hydrogen bonding promoters is not crucial. The coupling of the hydrogen bonding promoters with the gallotannin allows improving cohesion of the coating while benefiting of the advantages of using gallotannin or a gallotannic compound as described above. According to the invention, any hydrogen bonding promoter known to the skilled person can replace one or more hydroxyl group of gallotannin.

In embodiments, the hydrogen bonding promoter may be that described in U.S. Pat. Nos. 6,506,536 and 6,902,860, which are incorporated herein by reference.

Molecules, oligomers and polymers comprising functional groups, which provide multiple hydrogen bonds to form supramolecular polymers, are also disclosed in Chemical Review, 1997, Vol. 9-1-97, Pages 1,681 to 1,712 and Chemical Review, 2001, Volume 101, Pages 4071 to 4097, which are incorporated herein by reference.

In embodiments, the hydrogen bonding promoter may be that described in WO 98/42507 or WO 99/11458, U.S. Pat. Nos. 6,461,795, 6,613,494, 6,506,536, 6,902,860, WO 2004/020484.

In embodiments, the hydrogen bonding promoter may comprise one or more alkyl and/or aryl. The aryl and/or alkyl comprising one or more functional groups capable of forming hydrogen bonds. The alkyl and aryl may be substituted by alkyl, aryl, alkyl aryl and/or poly(alkylene glycol). The alkyl may be linear, branched and/or cyclic alkyl group. In other words, the alkyl may comprise linear parts, branched parts and cyclic parts at the same time. The alkyl group may have 1 to 12 carbon atoms. In the above, when it is said that the alkyl optionally comprises the listed functional groups, it means that the functional groups may be at end either of the alkyl or in between any two carbon atoms of the alkyl or its substituents. The aryl may comprise between 5 and 12 carbon atoms. The aryl may be a heteroaryl where one or more carbon atoms are replaced by nitrogen atoms.

In embodiments, the hydrogen bonding promoters may be derivatives of ureidopyrimidinone, 1,5-pyridine, or 1,8-naphthylridine. For example, these substituents may be:

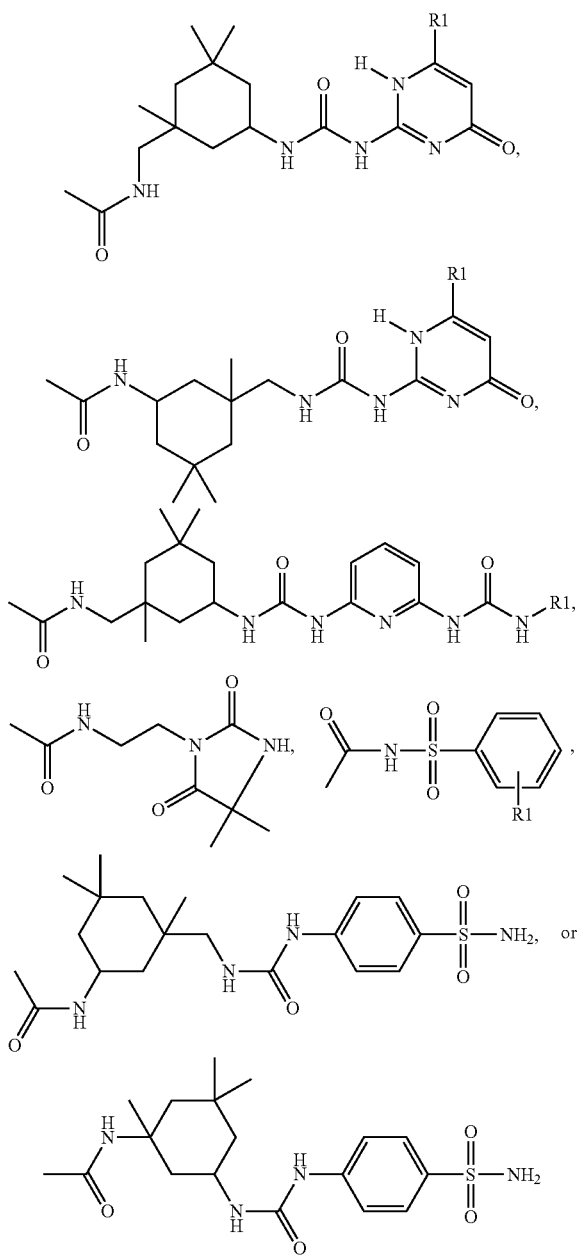

wherein R1 represents alkyl, poly(alkylene glycol), alkyl aryl, and aryl, wherein, in embodiments, alkyl has from 1 to 10 carbon atoms, poly(alkylene glycol) has between 1 and 50 repeat unit, alkylene has from 1 to 10 carbon atoms, and aryl has 5 or 6 carbon atoms.

Chromophores

Chromophores are molecules, oligomers, or polymers used in printing plates, which become excited and/or decompose when exposed to imaging light and thus generate heat, donate electrons and/or undergo reaction to produce functional groups that are more soluble in aqueous developers.

The purpose of the chromophores is to generate heat, donate electrons and/or become more soluble when exposed to imaging radiation. In positive plates, the heat will disrupt the supramolecular structure, which is formed via hydrogen bonds or ionic interaction, in the imaged areas of the printing plate, allowing developing the plates and printing. The increased solubility will also allow developing the plates and printing. In negative plates, the chromophore acts as an electron-donor, which donates electrons to the electron-acceptor initiator, which in turns will generate free radicals or acid to promote the crosslinking reaction.

Chromophores are well-known to persons of skill in the art. It will be clear to the skilled person that the exact nature of the chromophores is not crucial. The coupling of the chromophores with the gallotannin allows generating the necessary heat/electrons in the imaged areas of the coating while benefiting of the advantages of using gallotannin or a gallotannic compound as described above. According to the invention, any chromophore known to the skilled person can replace one or more hydroxyl group of gallotannin.

Such chromophores will be sensitive to the imaging radiation to be used to image the printing plate. For use in a thermal (or NIR sensitive) printing plate, a chromophore sensitive to radiation in the near infrared (NIR) range of wavelength will be used. Similarly, for use in an UV sensitive printing plate, a chromophore sensitive to radiation in the ultraviolet (UV) range of wavelength will be used.

In embodiments, the chromophore will be an NIR sensitive chromophore having a strong absorption band between 700 and 1100 nm.

Examples of NIR sensitive chromophores include azo dyes, squarylium dyes, croconate dyes, triarylamine dyes, thioazolium dyes, indolium dyes, oxonol dyes, oxazolium dyes, cyanine dyes, merocyanine dyes, phthalocyanine dyes, indocyanine dyes, indotricarbocyanine dyes, hemicyanine dyes, streptocyanine dyes, oxatricarbocyanine dyes, thiocyanine dyes, thiatricarbocyanine dyes, merocyanine dyes, cryptocyanine dyes, naphthalocyanine dyes, polyaniline dyes, polypyrrole dyes, polythiophene dyes, chalcogenopyryloarylidene and bi(chalcogenopyrylo)-polymethine dyes, oxyindolizine dyes, pyrylium dyes, pyrazoline azo dyes, oxazine dyes, naphthoquinone dyes, anthraquinone dyes, quinoneimine dyes, methine dyes, arylmethine dyes, polymethine dyes, squarine dyes, oxazole dyes, croconine dyes, porphyrin dyes, and any substituted or ionic form of the preceding dye classes.

Suitable NIR sensitive chromophores are also described in U.S. Pat. Nos. 5,208,135, 6,569,603, 6,787,281, WO 2004/101280, and EP 1 182 033, which are incorporated herein by reference. Further useful IR chromophores are described in EP 438 123 and U.S. Pat. No. 7,135,271.

In embodiments, the chromophore may be that described in U.S. Pat. Nos. 6,261,740, 6,124,425, 6,177,182, 6,960,422, 6,969,575, 6,582,882, 6,846,614, 6,899,994, U.S. 2005/0123853, U.S. 2009/0186299, U.S. 2009/0111051, EP 0 823 327, WO 98/42507, WO 99/11458, U.S. Pat. Nos. 6,461,795, 6,613,494, WO 2004/020484, U.S. Pat. No. 6,255,033. U.S. Pat. Nos. 6,541,181, 6,124,425, 6,177,182, 7,544,462, U.S. 2007/0808434, WO 2008/156552, and U.S. 2009/0004599, which are incorporated herein by reference.

NIR sensitive chromophores having the following structures can also be used:

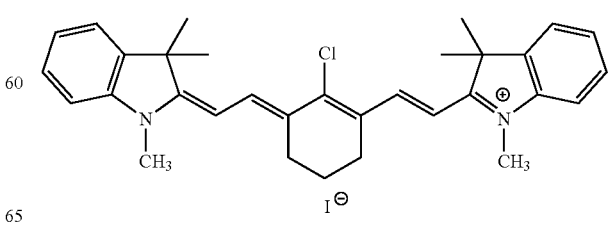

ADS775AT

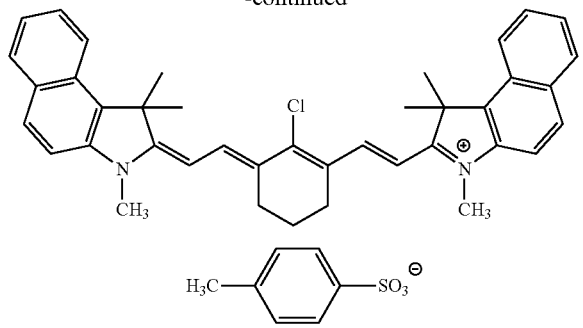

ADS830AT

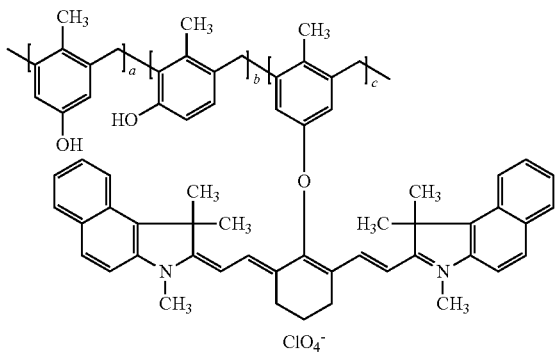

Thermolak® 1010 wherein a, b, and c are the molar ratios, which are 0.73, 0.25, and 0.02, respectively.

These are commercially available from American Dye Source, Inc. (Baie d'Urfe, Quebec, Canada)

In embodiments, the NIR sensitive chromophore may be an azo dye or an aryl amine dye. As used herein, an "azo dye" has its usual meaning in the art. More specifically, the "azo dye" can be understood as being a chromophore comprising an azo functional group, i.e. two double bonded nitrogen atoms: R—N=N—R'. In embodiments, the R and R' groups are aromatic, which helps stabilize the N=N group by making it part of an extended delocalized system. As used herein, an "aryl amine dye" has its usual meaning in the art. More specifically, the "aryl amine dye" can be understood to be a chromophore comprising an aryl amine group, i.e. an aryl group having attached thereto a nitrogen atom: Aryl-N($R_1$)($R_2$), wherein $R_1$ and $R_2$ independently are hydrogen, alkyl or aryl. In embodiments, alkyl may be linear, branched or cyclic $C_1$-$C_{12}$ and aryl may comprise between 5 and 12 carbon atoms.

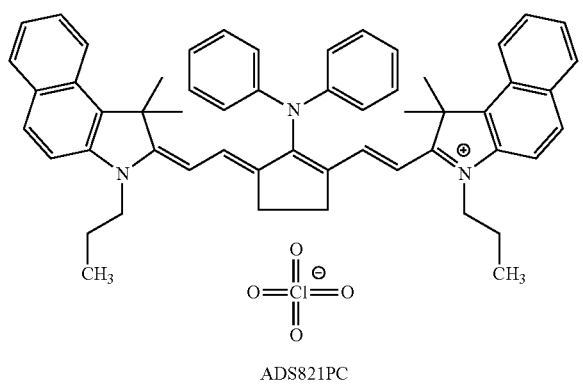

ADS821PC

These are available from American Dye Source, Inc. (Baie d'Urfe, Quebec, Canada).

Examples of suitable NIR sensitive polymeric chromophores are described in U.S. Pat. Nos. 6,124,425; 6,177,182; and 7,473,515, which are incorporated herein by reference. NIR sensitive polymeric chromophores having the following structures can be used:

In embodiments, the NIR sensitive chromophore is one of the following, which are commercially available from American Dye Source, Inc. (Bale d'Urfe, Quebec, Canada). This

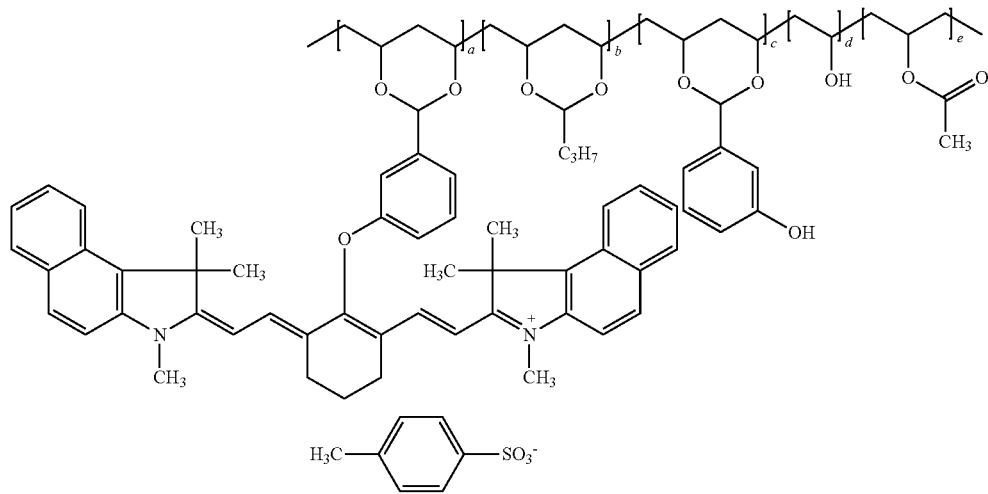

Thermolak® 8020 wherein a, b, c, d, and e are the molar ratios, which are 0.10, 0.30, 0.50, 0.08 and 0.02, respectively.

type of NIR chromophores is also an electron donor that can be used in negative-working printing plates.

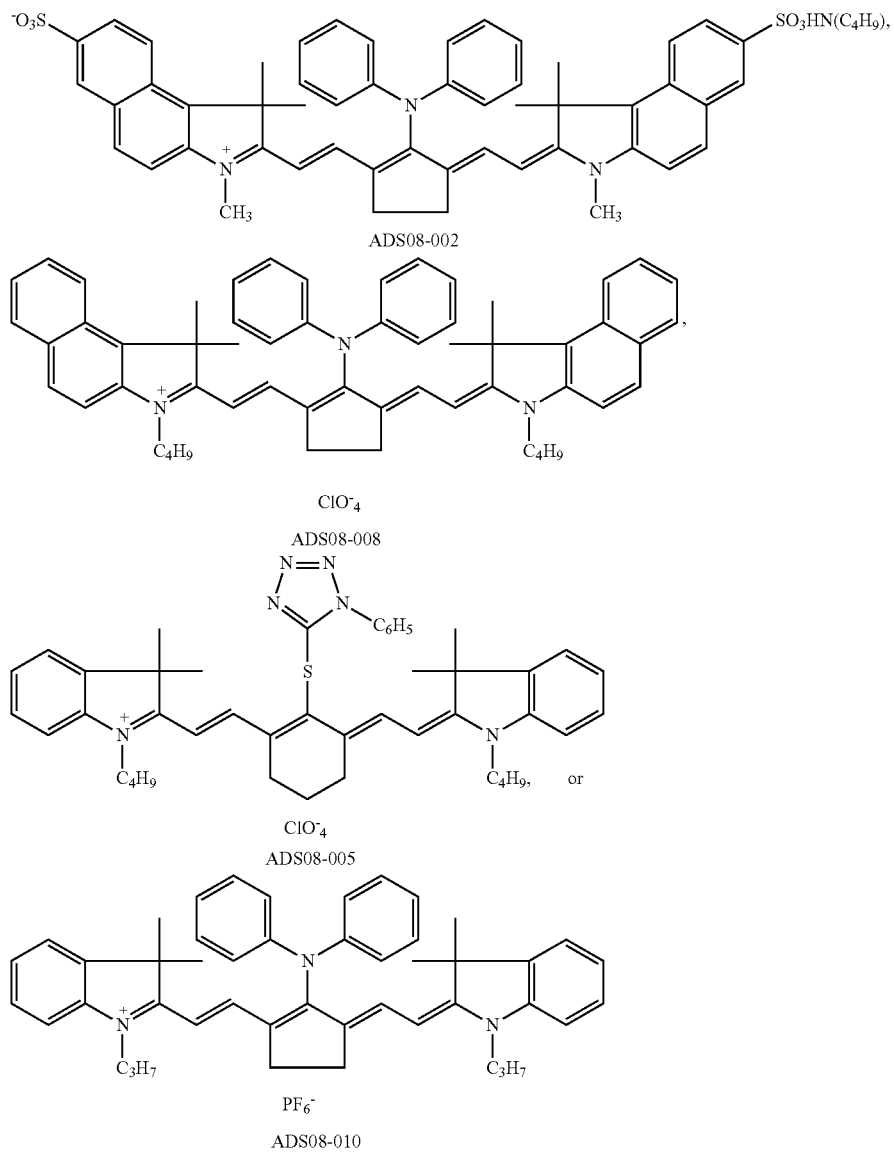

In embodiments, the NIR sensitive chromophore is a near infrared absorbing polymeric particles as described in U.S. Patent Application No. 2008/0171286, which is incorporated herein by reference.

In embodiments, the chromophore will be a UV sensitive chromophore having a strong absorption band between 300 and 450 nm.

Binders

Binders are oligomers or polymers used in printing plates to provide a cohesive film suprastructure.

The purpose of the binders is to provide a cohesive film suprastructure, which will be disrupted when exposed to the heat/electrons generated by the chromophores. This will create imaged areas on the printing plate, allowing developing the plates and printing. Binders are well-known to persons of skill in the art. It will be clear to the skilled person that the exact nature of the binders is not crucial. The coupling of the binders with the gallotannin allows generating the necessary cohesive film suprastructure while benefiting of the advantages of using gallotannin or a gallotannic compound as described above. According to the invention, any binder known to the skilled person can replace one or more hydroxyl group of gallotannin.

In embodiments, the binders can be oligomers or polymers derived from acrylate, methacrylate, vinyl alcohol and their copolymers thereof.

In embodiments, the binders may be that described in U.S. Pat. Nos. 6,846,614 or 6,899,994, U.S. 2005/0123853, U.S. Pat. No. 7,261,998, U.S. 2009/0111051, WO 98/42507, WO 99/11458, U.S. Pat. Nos. 6,461,795, 6,613,494, WO 2004/020484, U.S. Pat. Nos. 6,255,033, 6,541,181, 7,544,462, U.S. 2007/0808434, WO 2008/156552 and U.S. 2009/0004599, which are incorporated by reference herein.

Examples of binders include acetal copolymers. Such acetal copolymers may have the following chemical structures:

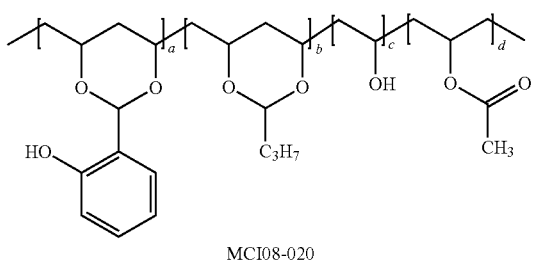

MCI08-020 wherein a, b, c and d are the molar ratios, which are 0.60, 0.25, 0.13, and 0.02, respectively.

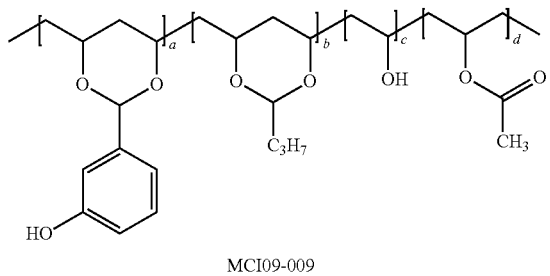

MCI09-009 wherein a, b, c, and d are the molar ratios, which are 0.60, 0.30, 0.08 and 0.02, respectively.

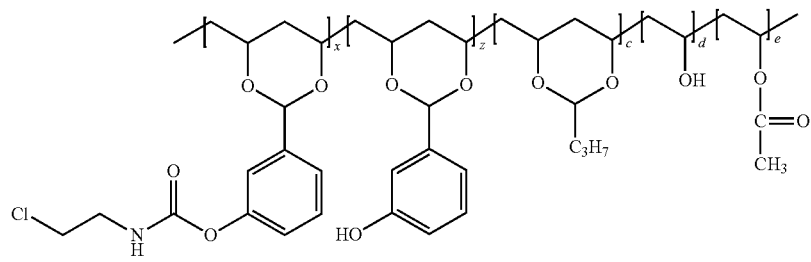

MCI09-030 wherein x, z, c, d and e are the number of repeating units, which are 9, 269, 76, 74, and 7, respectively.

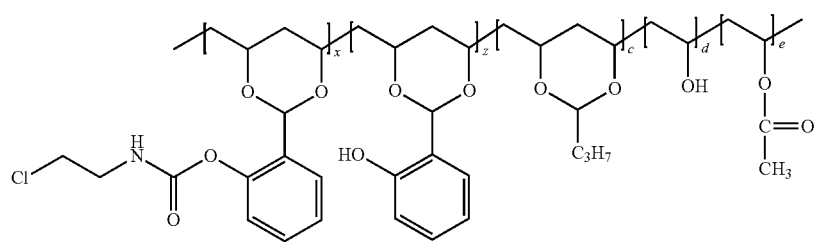

MCI09-032 wherein x, z, c, d and e are the number of repeating units, which are 3, 300, 83, 81, and 8, respectively.

These binders are available from MyLan Chemicals Inc. (LongDuc Industrial Park, Travinh, Vietnam)

Other examples of binders include Novolak resins. In embodiments, the Novolak resin is that commercially available from Hexion (USA) under trade names LB9900, LB6564, and PD494 or other commercially available Novolak resins from Asahi Chemical Specialty (Japan), such as EP6050 and EP4050.

Method of Producing a Gallotannic Compound

The present invention also relates a method of producing a gallotannic compound.

The method comprises the step of a) providing gallotannin, and b) replacing one hydroxyl group of gallotannic with a substituent, wherein the substituent is as described above.

Printing Plate Coating Compositions

The present invention also relates to a printing plate coating composition comprising gallotannin or the above-described gallotannic compound.

As stated above, the present inventors have found that adding gallotannin to a pre-existing lithographic printing plate coating composition and/or attaching gallotannin to one or more components of such a pre-existing coating composition [by way of substituting one or more of the hydroxyl groups of gallotannin with said component(s) to produce a gallotannic compound] improves properties of the coating, such as its adhesion to the substrate and its run length properties, which allows longer run length compared to similar coatings without gallotannin or gallotannic compounds.

There are numerous examples of pre-existing coating compositions in the prior art. The skilled person will know how to produce such compositions. Based on the present description of gallotannic compounds as well as the beneficial effect of using gallotannin and said gallotannic compounds in coating compositions for printing plates, the skilled person will be readily able to add gallotannin to any pre-existing coating composition and/or to attach gallotannin to one or more components of a pre-existing coating composition.

There are numerous components for use in coating compositions disclosed in the prior art. The skilled person knows how to produce these components. Moreover, the skilled person knows how to choose and match these components in suitable amounts to arrive at a coating composition suitable for his/her needs. Based on the present description of gallotannic compounds as well as the beneficial effect of using gallotannin and said gallotannic compounds in coating compositions for printing plates, the skilled person will be readily able, as stated above, to choose and match coating composition components in suitable amounts to arrive at coating compositions suitable for his/her need and, additionally, to add gallotannin to such coating compositions and/or to attach gallotannin to one or more components of such coating compositions.

Nevertheless, the following constitutes general indications on how to make such coating compositions and how to use gallotannin and/or gallotannic compounds in such compositions.

In embodiments, the coating composition may be sensitive to imaging radiation. There will be, upon exposure to imaging radiation, a physical or chemical process in the imaging coating produced using the coating composition so that 1) the imaged areas will be different from the non-imaged areas and 2) development will produce an image on the printing plate.

Such coating composition may be for positive-working or negative-working printing plates.

In embodiments, a coating composition for negative- or positive-working plates comprises between about 1 and about 80 w/w % of the gallotannic compound. In embodiments, the coating composition comprises 10, 20, 30, 40, 50, 60, or 70 w/w % or more of the gallotannic compound. In embodiments, the coating composition comprises 70, 60, 50, 40, 30, 20, or 10% or less of the gallotannic compound.

In embodiments, the composition comprises at least 1.0 w/w % of gallotannin. When gallotannin is used in positive- or negative-working printing plates, care should taken not to use too much of it as it is water soluble and may decrease the performances of the coating. Typically, gallotannin can be used in an amount of a few w/w %. In embodiments, the coating composition comprises about 3 w/w % of gallotannin. It is important to note that this precaution typically does not apply to gallotannic compounds, which are generally less soluble in water than gallotannin (or are even insoluble in water).

A coating composition for negative-working lithographic printing plate should generally include at least a crosslinker and an initiator. In embodiments, the composition may comprise between about 5 and about 50 w/w % of the crosslinker. In embodiments, the composition may comprise between about 1 and about 5 w/w % of the initiator.

A coating composition positive-working lithographic printing plate should generally include at least a binder and a chromophore. In embodiments, the composition may comprise between about 50 and about 90 w/w % of the binder. In embodiments, the composition may comprise between about 1 and about 10 w/w % of the chromophore.

Coating compositions for both positive- and negative-working lithographic printing plate may also include adhesion promoters and hydrogen bonding promoters. In embodiments, the composition may comprise between about 1 and about 5 w/w % of the adhesion promoter. In embodiments, the composition may comprise between about 1 and about 20 w/w % of the hydrogen bonding promoter.

The coating composition may be UV sensitive or NIR sensitive. If the coating composition is UV sensitive, the initiator and/or the chromophore as the case may be will absorb UV light. If the coating composition is NIR sensitive, the initiator and/or the chromophore as the case may be will absorb NIR light.

In embodiments, the crosslinkers, initiators, binders, chromophores, adhesion promoters and hydrogen bonding promoters are as described above with respect to the substituents that can be attached to gallotannin.

In the coating composition, the crosslinkers, initiators, binders, chromophores, adhesion promoters and hydrogen bonding promoters may "stand alone" or they may be attached to gallotannin as described above.

The coating composition comprises gallotannin and/or one or more of the gallotannic compounds described above. In embodiments, the coating composition may comprise a mixture of gallotannin with one or more gallotannic compounds or a mixture of gallotannic compounds.

Optional Additives

The coating composition may also comprise optional additives as described below.

In embodiments, the coating composition further comprises one or more additives. Such additives may be film forming additives, color formers, stabilizers, pigments, visible dyes and the like. Such additives are well known to the persons of skill in the art. Any optional additive known to the skilled person may be used in the coating composition. These additives may "stand alone" or they may be attached to gallotannin to form a gallotannic compound. The present invention thus also include gallotannic compounds wherein the substituent(s) is(are) any such additive.

Thus, the coating composition may comprise pigments and visible dyes. In embodiments, the pigment is phthalocyanine blue 15:3 dispersed in an acetal copolymer and 2-methoxy propanol solution. This material is commercially available from MyLan Chemicals Inc., Travinh, Vietnam. This pigment dispersion may be used in the coating composition in quantities ranging from 0.5 to 5 w/w %.

The coating composition may also comprise color formers to provide good image printout after laser imaging. Any color former known to the person of skill in the art to be suitable for use in the present composition may be used. The color formers may be the derivatives of triarylpyridine, xanthene and isobenzofuranone. In embodiments, the color formers may be chosen to be colorless and then become colored in the presence of free radical or acid. For example, the color formers may be:

3',6'-bis[N-[2-chlorophenyl]-N-methylamino]spiro[2-butyl-1,1-dioxo[1,2-benzisothiazole-3(3H), 9'-(9H)xanthene]](prepared by the method of U.S. Pat. No. 4,345,017);

3',6'-bis[N-[2-[methanesulfonyl]phenyl]-N-methylamino]spiro[2-butyl-1,1-dioxo[1,2-benzisothiazole-3(3H),9'-(9H)xanthene]](prepared by the method of U.S. Pat. No. 4,345,017);

9-Diethylamino[spiro[12H-benzo(a)xanthene-12,1'(3'H)-isobenzofuran)-3'-one] (available from BF Goodrich, Canada);

2'-di(phenylmethyl)amino-6'-[diethylamino]spiro[isobenzofuran-1(3H), 9'-(9H)-xanthen]-3-one (available from BF Goodrich, Canada);

3-[butyl-2-methylindol-3-yl]-3-[1-octyl-2-methylindol-3-yl]-1-(3H)-isobenzo furanone (available from BF Goodrich, Canada);

6-[dimethylamino]-3,3-bis[4-dimethylamino]-phenyl-(3H)-isobenzofuranone (available from BF Goodrich, Canada);

2-[2-Octyloxyphenyl]-4-[4-dimethylaminophenyl]-6-phenylpyridine (available from BF Goodrich, Canada); or Leuco lactone dyes, such as Blue-63, GN-169 and Red-40, which are available from Yamamoto Chemicals Inc., Japan.

The color formers may be used in the coating compositions in quantities ranging from about 0.5 to about 5 w/w %.

The coating composition may also comprise one or more suitable solvent. This allows forming a coating on a substrate. Any solvent known to the person of skill in the art to be appropriate for this purpose can be used. Non-limiting examples of such solvent include n-propanol, isopropanol, 2-methoxy propanol, ethyl glycol, water or a mixture thereof.

Lithographic Printing Plates and Method of Producing and Using

In another aspect, the present invention relates to a lithographic printing plate comprising a coating, the coating being a coating prepared from the above described coating composition.

The coating is deposited on a substrate. In embodiments, the substrate is anodized aluminum, plastic films or paper. Aluminum substrates may be brushed-grained or electrograined, then anodized with acidic solutions. The near infrared radiation-sensitive coating may have a coating weight between about 0.5 and about 2.5 g/m².

In embodiments, the coating is a radiation-sensitive coating. In embodiments, there may be one or more layer between the substrate and the radiation-sensitive coating and/or on top of the radiation-sensitive coating as known to the person of skill in the art.

Any such layer known to the skilled person may be used in the printing plates. The components in these layers may "stand alone" or they may be attached to gallotannin to form a gallotannic compound. The present invention thus also include gallotannic compounds wherein the substituent(s) is(are) any components used in such known layers.

For example, a polymeric adhesion-promoting and/or heat insulating layer may be present between the substrate and the near infrared radiation-sensitive coating. This layer may be obtained from aqueous solutions containing poly(acrylic acid), poly(acrylic acid-co-vinylphosphoric acid) or polyvinyl phosphoric acid, which are then dried using hot air at about 110° C. As stated above, these polymers can be attached to gallotannin and the present invention includes gallotannic compounds with these polymers attached. The coating weight of the adhesion-promoting and/or heat insulating layer may be between about 0.1 and about 1.0 g/m².

In another related aspect, the present invention relates to a method of producing a lithographic printing plate, the method comprising the step of: a) providing a substrate, and b) coating a coating composition as defined above on the substrate. In embodiments, the method further comprise the step of coating the substrate with a polymeric adhesion-promoting and/or heat insulating layer before step b).

In another related aspect, the present invention relates to a method of printing, the method comprising the step of: a) providing a lithographic printing plate as defined above, and b) imaging the printing plate with imaging radiation, c) developing the imaged printing plate, and d) using the developed printing plate on a printing press to print.

In embodiments, the imaged plate is developed off press with water or a developer. In alternative embodiments, the imaged plate is developed on press with fountain solutions and inks.

Some of the compounds described herein may exist as isomers of different types (optical, geometric and/or positional isomers for example). The present invention embraces all such isomers.

Unless otherwise noted, as used herein "alkyl" means linear, branched and/or cyclic alkyl group. In other words, the alkyl may comprise linear parts, branched parts and cyclic parts at the same time. The alkyl group may have 1 to 12 carbon atoms.

Unless otherwise noted, as used herein "aryl" means an aryl group having 1 to 3 cycles.

Herein, unless otherwise indicated, w/w % values are based on the total dry weight of the coating composition.

As used herein, "near infrared radiation" means electromagnetic radiation, such as that emitted by a laser, with a wavelength between about 700 and about 1100 nm. Non-limiting examples of such near infrared radiation is the light emitted by diode lasers, which are equipped with plate-setters available from Creo-Kodak, Dinippon Screen, Heidelberg and Presstek International.

As used herein, "UV radiation" means electromagnetic radiation, such as that emitted by a laser, with a wavelength between about 300 and about 450 nm. Non-limiting examples of such UV radiation is the light emitted by Nd-YAG and GaN lasers or mercury lamps.

As used herein, "about" means plus or minus 5% of the numerical value thus qualified.

Other objects, advantages and features of the present invention will become more apparent upon reading of the following non-restrictive description of specific embodiments thereof, given by way of example only with reference to the accompanying drawings.

Description of Illustrative Embodiments

The present invention is illustrated in further details by the following non-limiting examples. These examples use the compounds listed in the following glossary.

| | Glossary |
|---|---|
| ADS08-008 | Near infrared absorbing dye, available from American Dye Source, Inc., Baie d'Urfe, Quebec, Canada having the chemical formula given above. |
| ADS775PI | 2-[2-[2-chloro-3-[2-(1,3-dihydro-1,3,3-trimethyl-2H-indolenine-2-ylidene)-ethylidene]-1-cyclohexen-1-yl]-ethenyl]-1,3,3-trimethyl-1H-indolium iodide, available from American Dye Source, Inc., Quebec, Canada. |
| ADS830AT | 2-[2-[2-chloro-3-[2-(1,3-dihydro-1,3,3-trimethyl-2H-benz[e]indol-2-ylidene)-ethylidene]-1-cyclohexen-1-yl]-ethenyl]-1,3,3-trimethyl-1H-benz[e]indolium 4-methylbenzenesulfonate, available from American Dye Source, Inc., Quebec, Canada. |
| Basic Green 4 | Visible colorant available from Spectra Colors, Kearny, New Jersey, USA. |
| Blue 63 | Blue Color Former, available from Yamamoto Chemicals Inc., Japan. |
| BYK 307 | Polyether modified siloxane copolymer, available from BYK Chemie, USA. |
| BYK 336 | Polyether modified siloxane copolymer, available from BYK Chemie, USA. |
| CAP | Cellulose Acetate Phthalate, available from Eastman Chemicals Company, USA. |
| CEI | 2-Chloroethyl isocyanate, available from Sigma Aldrich Canada. |

-continued

| | Glossary |
|---|---|
| CN-M01 | 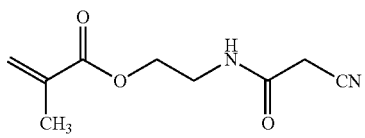<br>Cyanomethylamidoethyl methacrylate, available from American Dye Source, Inc., Baie d'Urfe, Quebec, Canada. |
| CN-M02 | 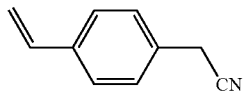<br>4-Vinylbenzyl cyanide, available from American Dye Source, Inc., Baie d'Urfe, Quebec, Canada. |
| CN-M04 | 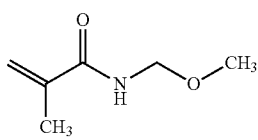<br>N-Methoxy methyl methacrylamide, available from American Dye Source, Inc., Baie d'Urfe, Quebec, Canada. |
| CN-M05 | 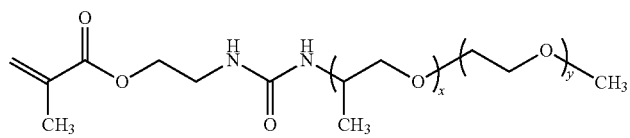<br>Urea linked poly(ethylene glycol-ran-propylene glycol), $M_n$~800, x = 1 and y = 9, available from American Dye Source, Inc., Baie d'Urfe, Quebec, Canada. |
| CN-M06 | 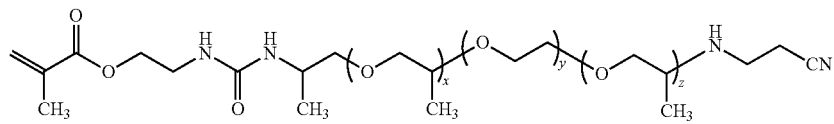<br>Urea linked poly(ethylene glycol-ran-propylene glycol), $M_n$~850, y = 9, x + z = 4, available from American Dye Source, Inc., Baie d'Urfe, Quebec, Canada. |
| CN-M07 | 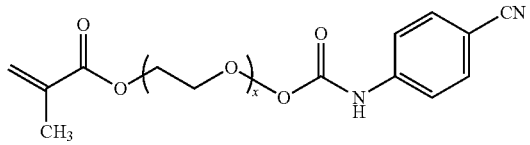<br>Poly(ethylene glycol) 4-cyanobenzyl carbamate methacrylate, $M_n$~2100, available from American Dye Source, Inc., Baie d'Urfe, Quebec, Canada. |
| Dowanol PM | 2-methoxy propanol, available from Dow Chemicals, USA. |
| Gallotannin | Gallotannin (tannic acid), available from Sigma Aldrich, Canada. |
| GSP90 | Aqueous alkaline developer for positive thermal plate, available from MyLan Chemicals Inc., Travinh, Vietnam. |
| HEMA | 2-hydroxymethacrylate, available from Sigma Aldrich, Canada. |
| Klucel E | Hydroxypropyl cellulose, available from Hercules, USA. |
| LB9900 | Novolak resin (50% solid in 2-methoxy propanol), available from Hexion, USA. |
| MMEA | 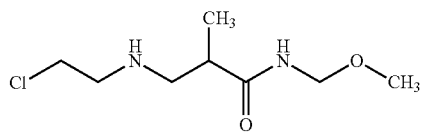<br>N-Methoxymethyl-(1-methyl-2-(2-chloroethyl)amino)-ethylamide, available from American Dye Source, Inc., Baie d'Urfe, Quebec, Canada. |

| | |
|---|---|
| MCI08-P020 | Acetal copolymer with average molecular weight 35,000 g/mole 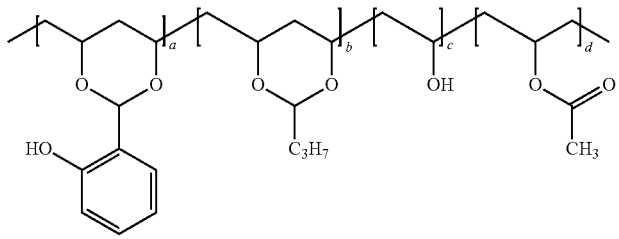 wherein a = 303, b = 83, c = 81 and d = 8. The molecular weight and molar ratios were obtained with GPC and proton NMR. |
| MCI09-P009 | Acetal copolymer with average molecular weight 32,000 g/mole. 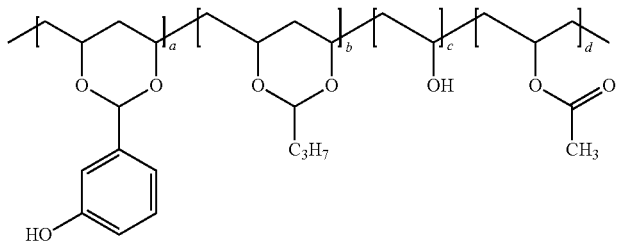 wherein a = 278, b = 76, c = 74, and d = 7. The molecular weight and molar ratios were obtained with GPC and proton NMR. |
| NCO-0450 | 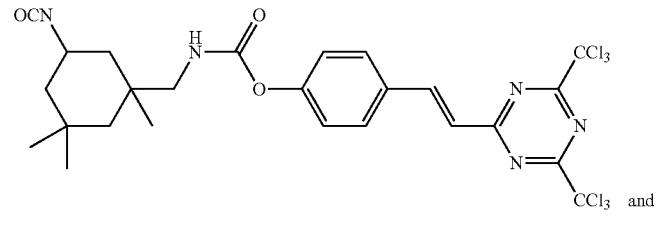 and 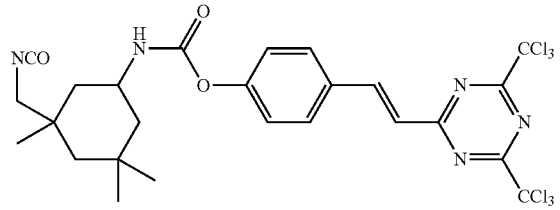 available in 1,3-dioxolane solution with 20% solid weight from American Dye Source, Inc., Baie d'Urfe, Canada. FW = 449.56 |
| NCO-0747 | 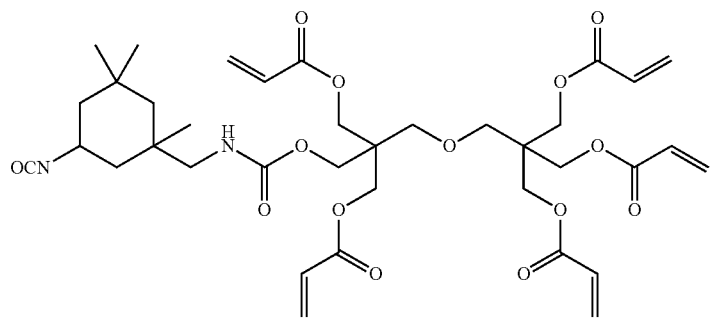 FW = 746.82, available in 1,3-dioxolane solution with 20% solid weight from American Dye Source, Inc., Baie d'Urfe, Canada. |

-continued

| | Glossary |
|---|---|
| NCO-1474 | A mixture of 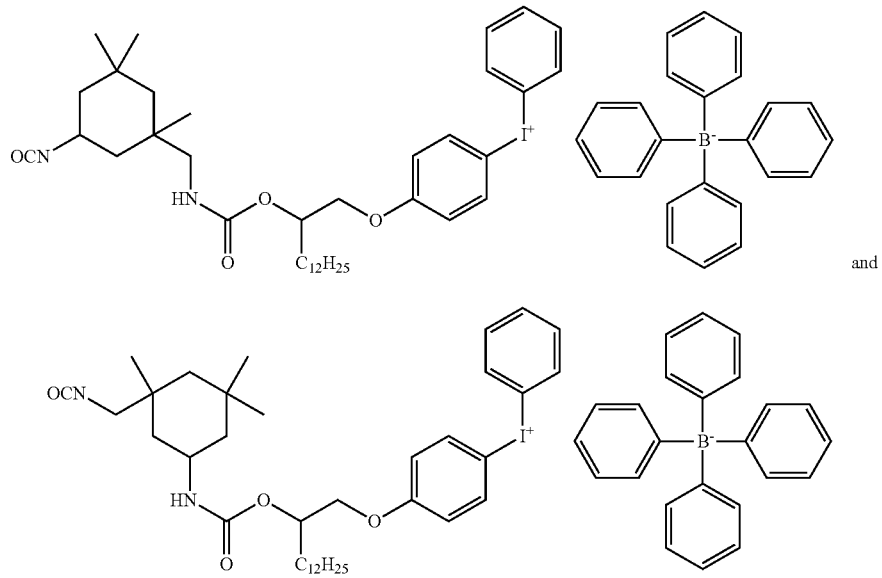 available in 1,3-dioxolane solution with 20% solid weight from American Dye Source, Inc., Baie d'Urfe, Canada. FW = 1474.22 |
| MMA | Methylmethacrylate, available from Sigma Aldrich, Canada. |
| PD08-001 | Phthalocyanine Blue 15:3 dispersed in acetal copolymer (50% pigment and 50% copolymer), available from MyLan Chemicals Inc., Travinh, Vietnam as 20% by solid weight in 2-methoxypropanol solution. |
| PP-06 | 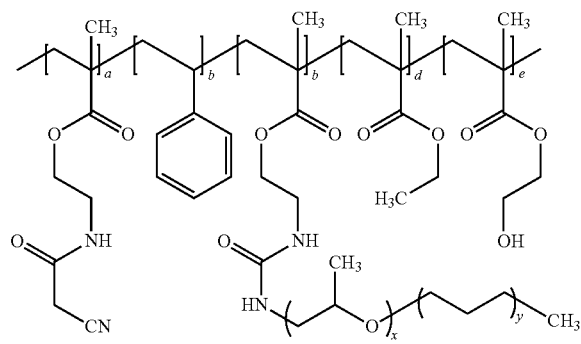 Polymeric particle PP-06, available from MyLan Chemicals Inc., Travinh, Vietnam |
| pTSI | 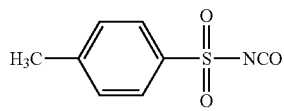 p-Toluenesulfonyl isocyate, available from Sigma Aldrich Canada. |
| Styrene | Styrene, available from Sigma Aldrich, Canada. |
| Thermolak ® 7525 | Novolak resin, available from Dye Source, Inc., Baie d'Urfe, Quebec, Canada. |
| Thermolak ® 8020 | As described above in the section relating to chromophores. |
| Tuxedo ® 600PFB | Mixtures of reactive iodonium oligomers, available from American Dye Source, Inc., Baie d'Urfe, Quebec, Canada. See FIG. 1(a) to (f). |

-continued

| Glossary | |
|---|---|
| Ureido-01 | 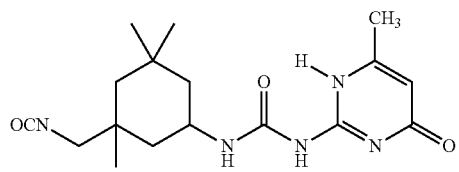<br>Ureidopyrimidinone precursor, available from American Dye Source, Inc., Baie d'Urfe, Quebec, Canada. |
| Ureido-02 | A mixture of following compounds<br>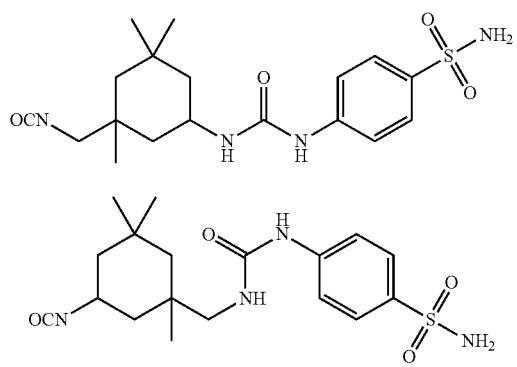<br>Available from American Dye Source, Inc., Baie d'Urfe, Quebec, Canada |
| Ureido-NCO | A mixture of the two following compounds<br>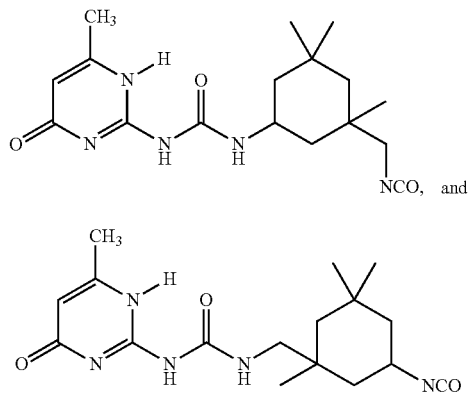<br>Available from American Dye Source, Inc., Baie d'Urfe, Quebec, Canada. |
| V59 | 2,2'-azobis(2-methylbutyronitrile), available from Wako (USA).<br>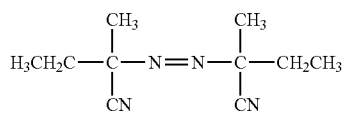 |

Synthesis of Gallotannic Compounds

The syntheses of the gallotannic compounds were performed in a 4 necks glass reactor equipped with a water condenser, a mechanical stirrer, a dropping funnel and a nitrogen or oxygen gas inlet. The molecular structures of the obtained materials were determined by proton NMR and FTIR spectroscopy. The UV-Visible near infrared spectra of the gallotannic compounds were measured in methanol solutions using a spectrophotometer Model PC (Shimazu).

Synthesis of Gallotannic Compounds for Use in Negative Plates

Gallotannic Compounds with Crosslinkers

EXAMPLE 1

Figure 2:
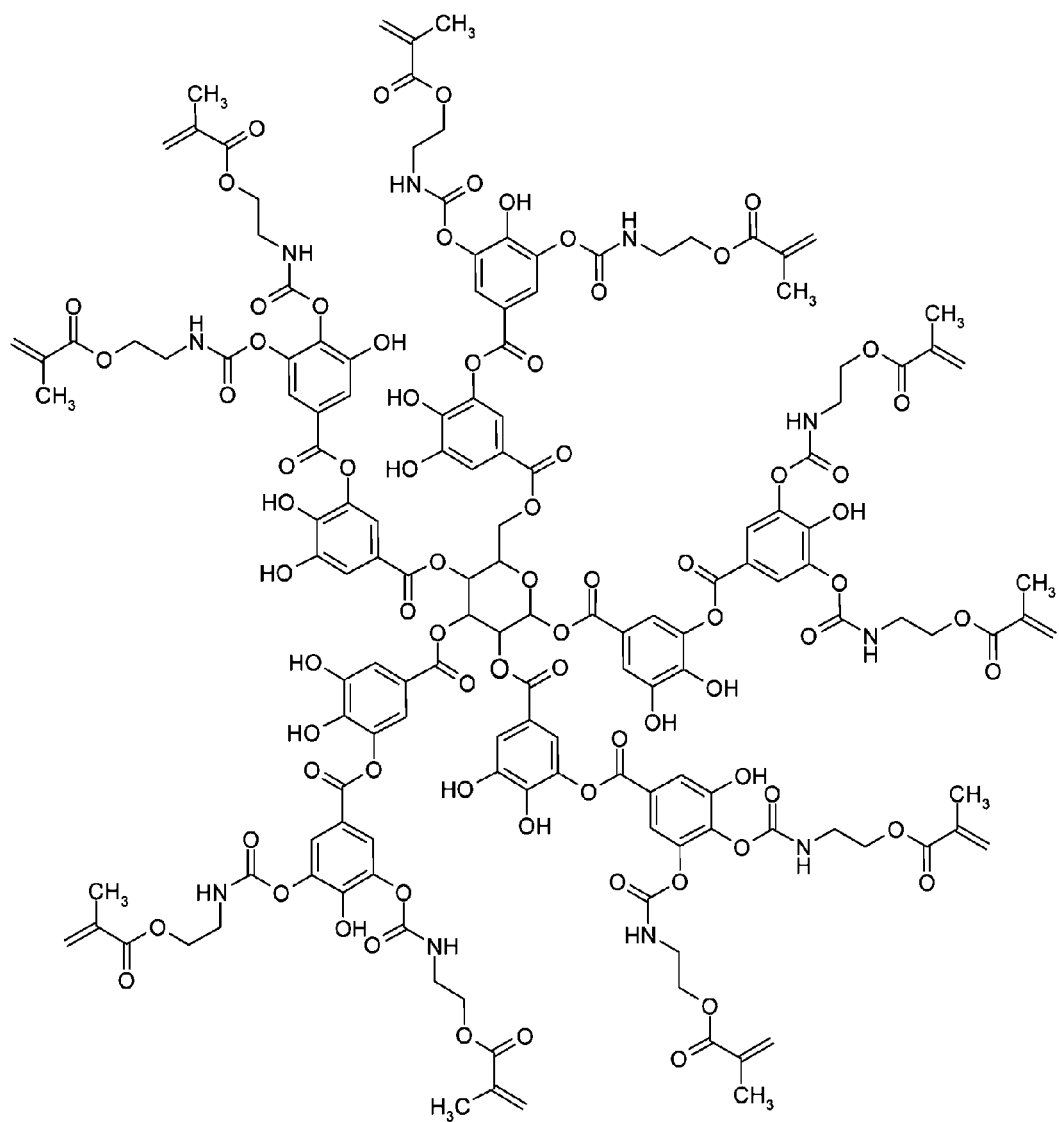
FIG. 2 is the ideal structure of gallotannic compound RGT-01.

Gallotannic compound RGT-01 shown in FIG. 2 was synthesized by slowly adding 155 grams of 2-isocyanatoethyl methacrylate (10 equivalents) in 500 grams anhydrous 1,3-dioxolane to a reaction flask containing 800 grams of anhydrous 1,3-dioxolane, in which were dissolved 170.1 grams of gallotannin (1 equivalent) and 0.5 grams of dibutyl tin dilaurate at 50° C., under oxygen atmosphere with constant stirring. After 30 hours of reaction, a sample of the reaction mixture was withdrawn from the reaction flask and its FTIR spectrum, recorded on KBr pellet, showed no —N═C═O peak at 2274 cm$^{-1}$, which indicated that the reaction was completed. The solid content of RGT-01 was adjusted to 20% by weight using 1,3-dioxolane.

EXAMPLE 2

Figure 3:
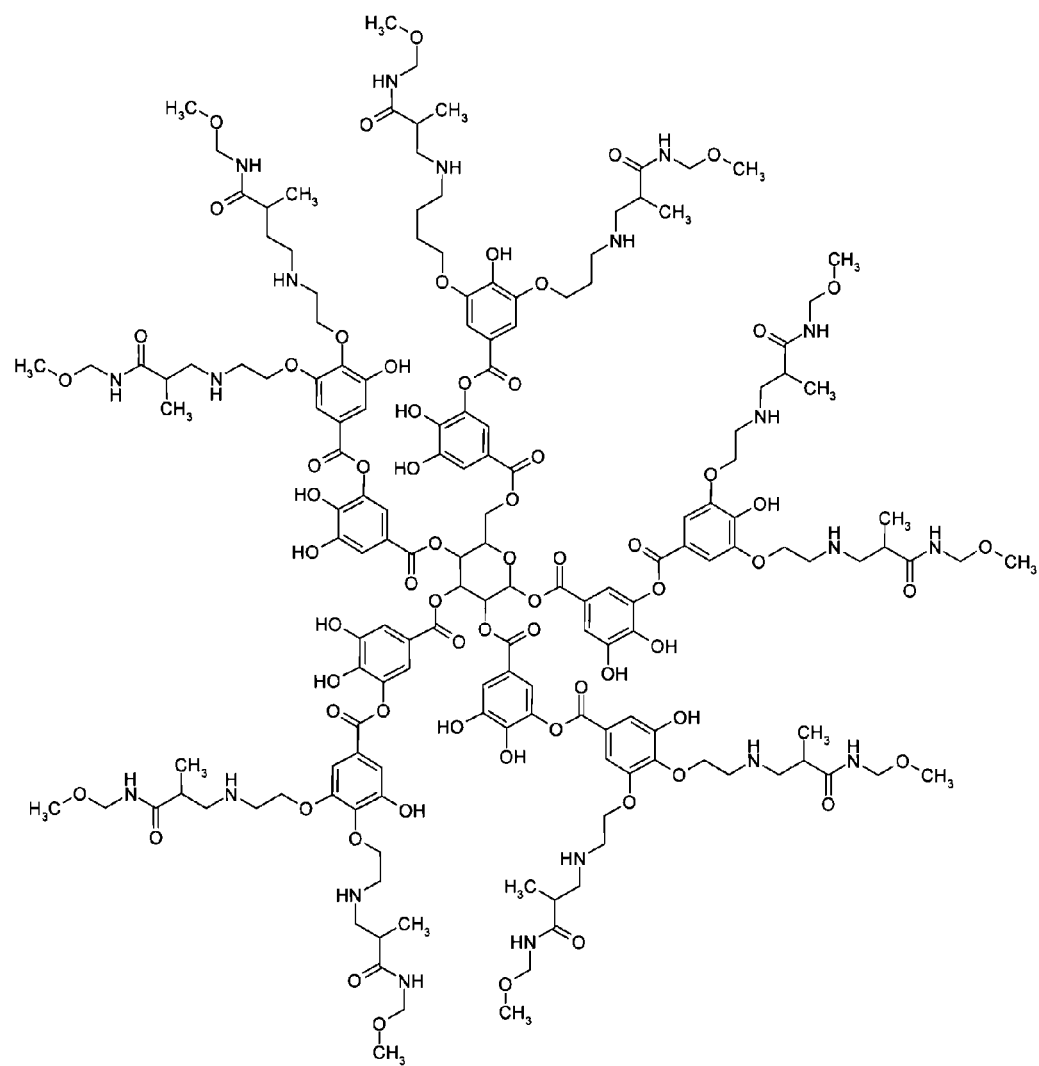
FIG. 3 is the ideal structure of gallotannic compound RGT-02.

Gallotannic compound RGT-02 shown in FIG. 3 was synthesized by slowly adding 42.0 grams of sodium hydride (10.5 equivalents) to a reaction flask containing 500 grams of anhydrous N,N-dimethylacetamide, in which were dissolved 170.1 grams of gallotannin under nitrogen atmosphere with constant stirring. About three hours later, the release of hydrogen gas by-product ceased and a solution containing 300 grams of N,N-dimethylacetamide and 209 grams of MMEA (10 equivalents) was slowly added to the reaction mixture. The reaction was stopped after 10 hours at 50° C. The solvent was removed using a rotary evaporator under vacuum until dry. The obtained solid was dissolved in anhydrous 1,3-dioxolane to provide a 20% solid solution. It was then gravity filtered to remove sodium chloride by-product.

EXAMPLE 3

Figure 4:
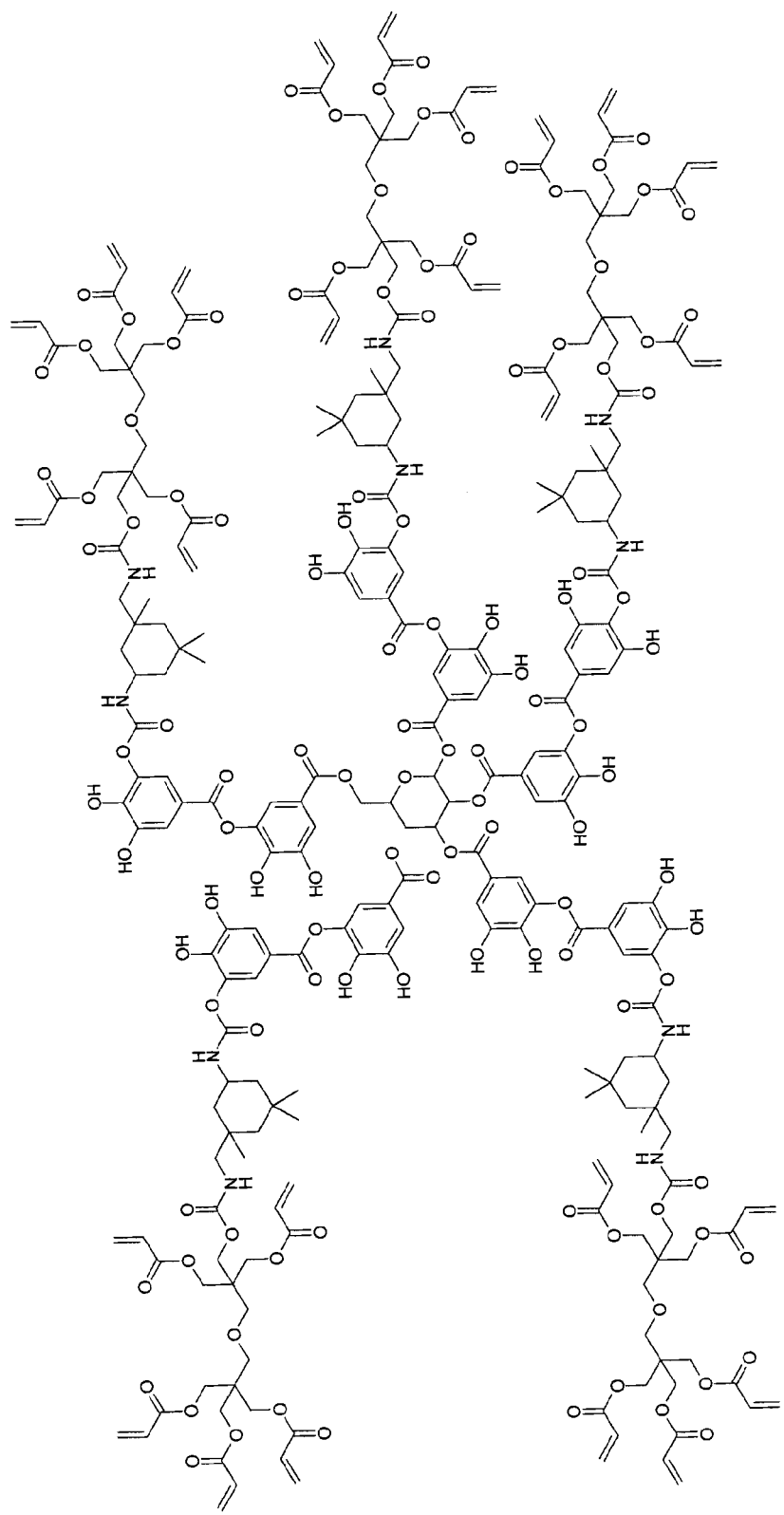
FIG. 4 is the ideal structure of gallotannic compound Gallo-25X.

The synthesis of Gallo-25X was performed by slowly adding 150 grams of a 1,3-dioxolane solution containing 37.4 grams of NCO-0747 into a mixture containing 100 grams of 1,3-dioxolane, 17.0 grams of gallotannin and 0.1 grams of dibutyl tin dilaurate under oxygen atmosphere and constant stirring at 57° C. After 5 hours of reaction, a sample was withdrawn from the reaction for FTIR analysis. The —NCO stretching band at 2210 cm$^{-1}$ had disappeared, which indicated that the reaction was complete. The solution was adjusted with 1,3-dioxolane to give 20% solid weight, which is a solution that is ready for use in coating plates. The idealized chemical structure of Gallo-25X is shown in FIG. 4.

Gallotannic Compounds with Initiators
Initiators for Thermal Plates

EXAMPLE 4

Figure 5:
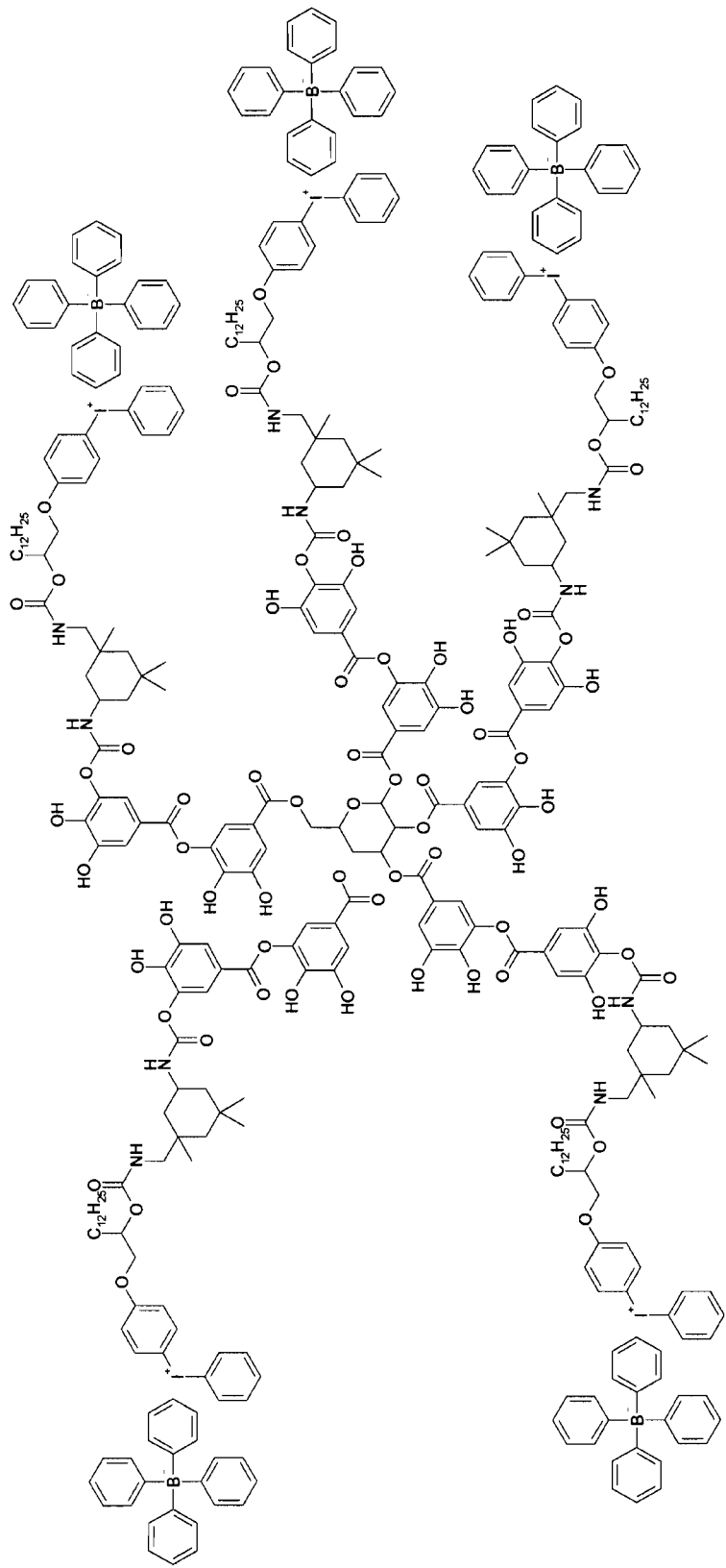
FIG. 5 is the ideal structure of gallotannic compound Gallo-Iodo.

The synthesis of a gallotannic compound comprising an iodonium salt substituent, Gallo-Iodo, for use as thermal free radical initiator was performed by slowly adding 300 grams of 1,3-dioxolane containing 73.8 of NCO-1474 and 0.1 grams of dibutyl tin dilaurate into a mixture containing 100 grams of 1,3-dioxolane and 17.0 grams of gallotannin under nitrogen atmosphere and constant stirring at 60° C. After 5 hours of reaction, a sample was withdrawn from the reaction for FTIR analysis. The —NCO stretching band at 2210 cm$^{-1}$ had disappeared, which indicated that the reaction was complete. The solution was adjusted with 1,3-dioxolane to give 20% solid weight, which is a solution that is ready for use in coating plates. The idealized chemical structure of Gallo-Iodonium is shown in FIG. 5.

Initiators for UV plates

EXAMPLE 5

Figure 6:
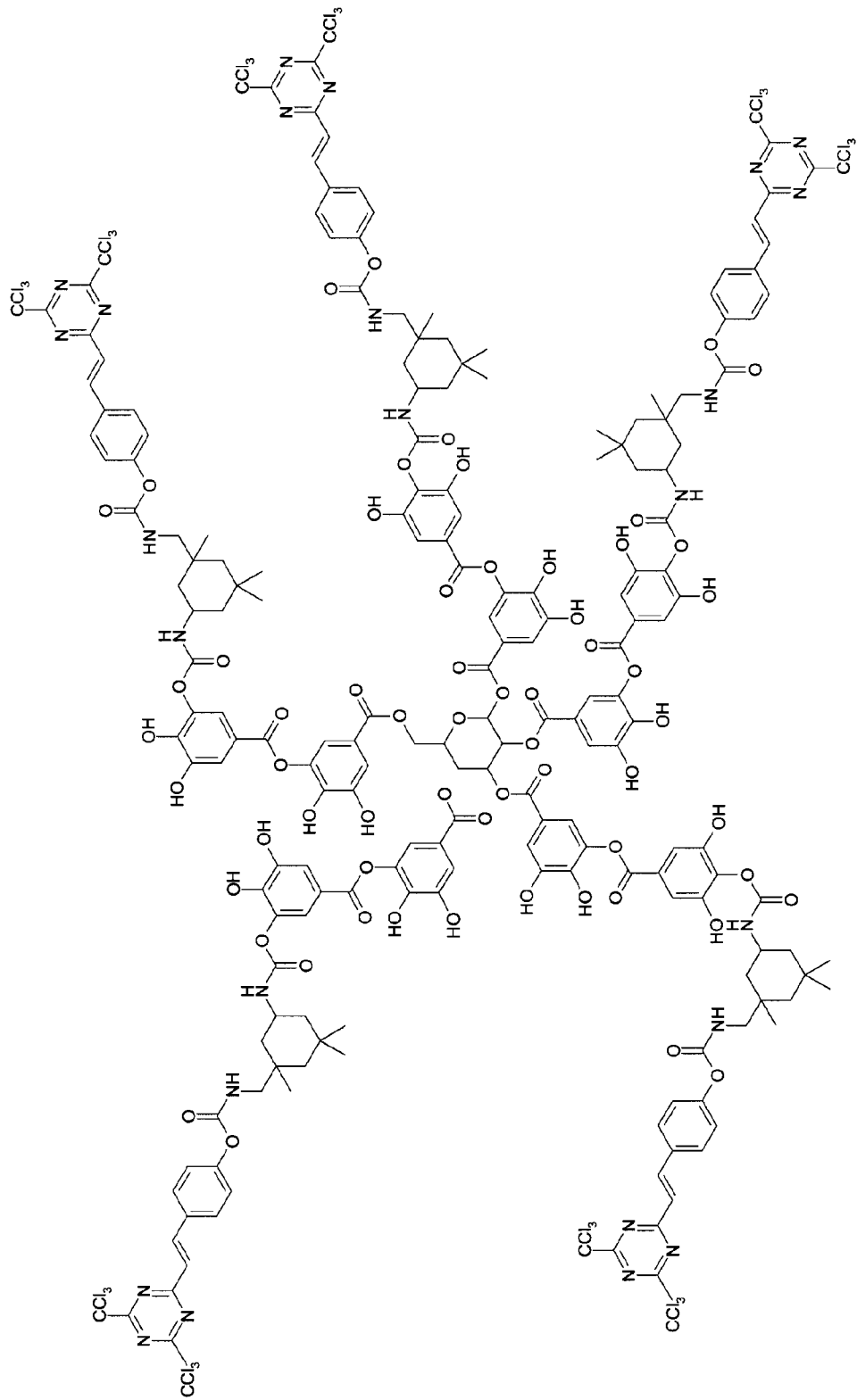
FIG. 6 is the ideal structure of gallotannic compound Gallo-Triazine.

A gallotannic compound comprising triazine substituent as a UV free radical initiator was synthesized by slowly adding 150 grams of 1,3-dioxolane, in which were dissolved 22.5 grams of NCO-0450 into a mixture containing 100 grams of 1,3-dioxolane and 17.0 grams of gallotannin under nitrogen atmosphere and constant stirring at 60° C. After 5 hours of reaction, a sample was withdrawn from the reaction for FTIR analysis. The —NCO stretching band at 2270 cm$^{-1}$ had disappeared, which indicated that the reaction was complete. The solution was adjusted with 1,3-dioxolane to give 20% solid weight, which is a solution ready for use in coatings plates. The idealized chemical structure of Gallo-Triazine is shown in FIG. 6.

Synthesis of Gallotannic Compounds for Use in Negative and Positive Plates
Gallotannic Compounds with Adhesion Promoters

EXAMPLE 6

Figure 7:
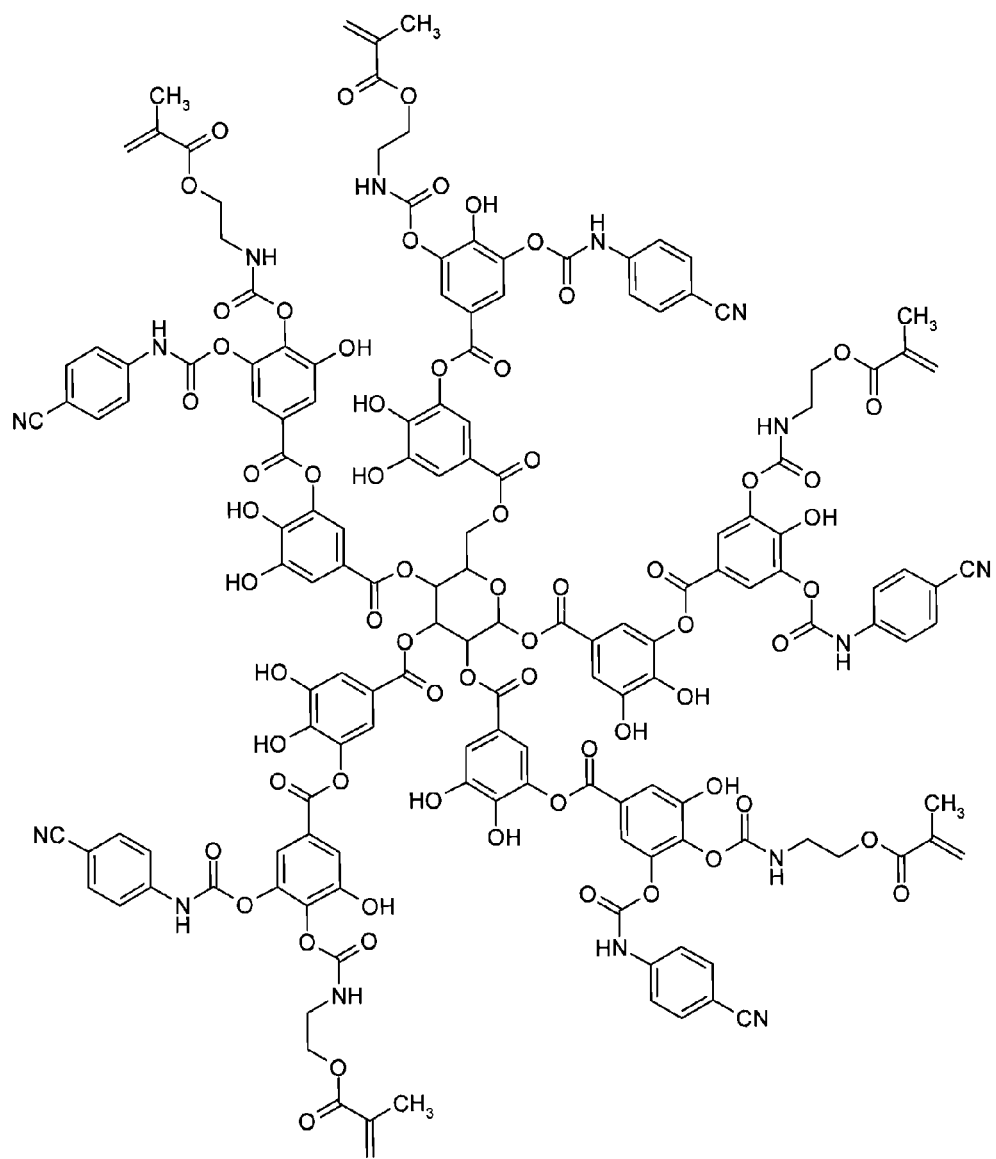
FIG. 7 is the ideal structure of gallotannic compound RGT-03.

Gallotannic compound RGT-03 shown in FIG. 7 was synthesized by slowly adding 79.0 grams of 4-cyanatobenzyl cyanide (5 equivalents) and 77.5 grams of 2-isocyanatoethyl methacrylate (5 equivalents) in 500 grams anhydrous 1,3-dioxolane to a reaction flask containing 800 grams of anhydrous 1,3-dioxolane in which were dissolved 170.1 grams of gallotannin (1 equivalent) and 0.5 grams of dibutyl tin dilaurate at 50° C., under oxygen atmosphere with constant stirring. After 10 hours of reaction, a sample of the reaction mixture was withdrawn from the reaction flask and its FTIR spectrum, recorded on KBr pellet, showed no —N═C═O peak at 2274 cm$^{-1}$, which indicated that the reaction was completed. The solid content of RGT-03 was adjusted to 20% by weight using 1,3-dioxolane.

Gallotannic Compounds with Hydrogen Bonding Promoters

EXAMPLE 7

Figure 8:
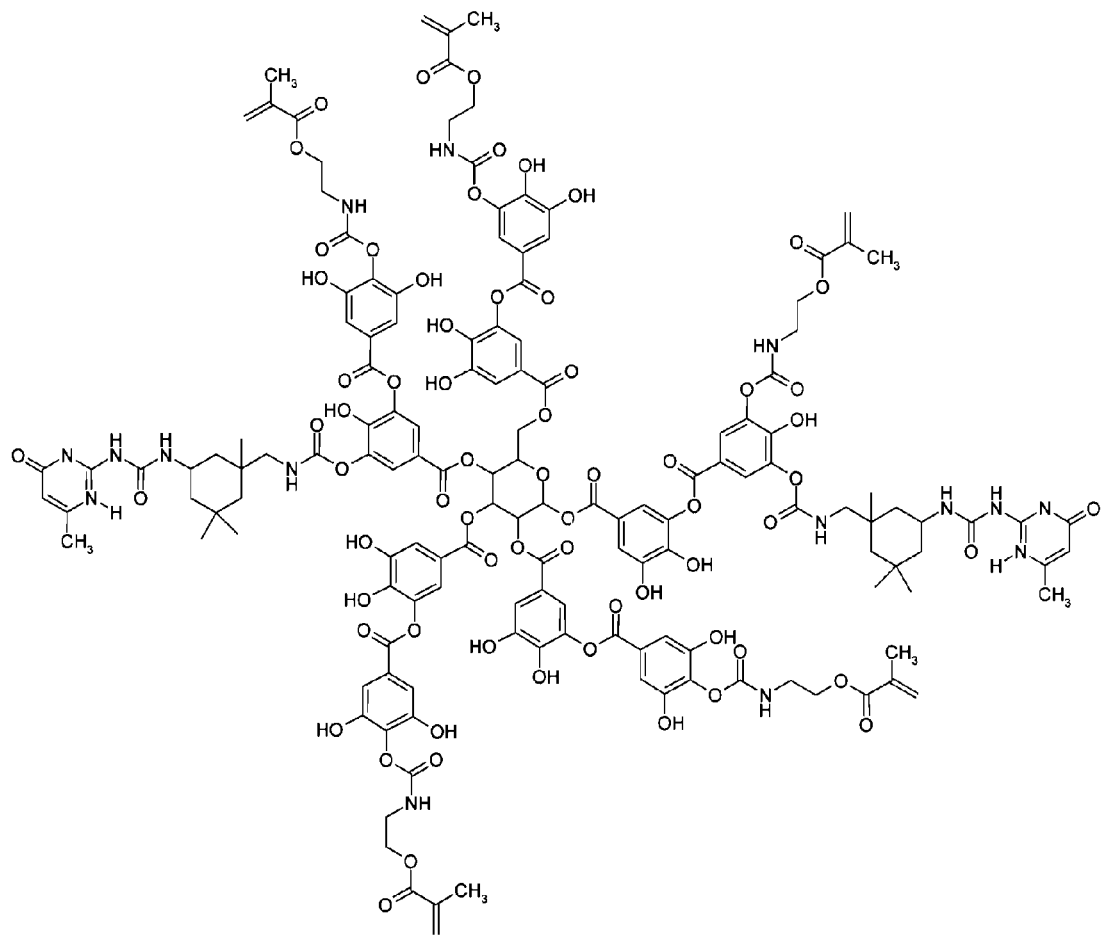
FIG. 8 is the ideal structure of gallotannic compound RGT-04.

Gallotannic compound RGT-04 shown in FIG. 8 was synthesized by slowly adding 69.8 grams of Ureido-01 (2 equivalents) and 77.5 grams of 2-isocyanatoethyl methacrylate (5 equivalents) in 500 grams anhydrous 1,3-dioxolane to a reaction flask containing 800 grams of anhydrous 1,3-dioxolane in which were dissolved 170.1 grams of gallotannin (1 equivalent) and 0.5 grams of dibutyl tin dilaurate at 50° C., under oxygen atmosphere with constant stirring. After 10 hours of reaction, a sample of the reaction mixture was withdrawn from the reaction flask and its FTIR spectrum, recorded on KBr pellet, showed no —N═C═O peak at 2274 cm$^{-1}$, which indicated that the reaction was completed. The solid content of RGT-04 was adjusted to 20% by weight using 1,3-dioxolane.

EXAMPLE 8

Figure 9:
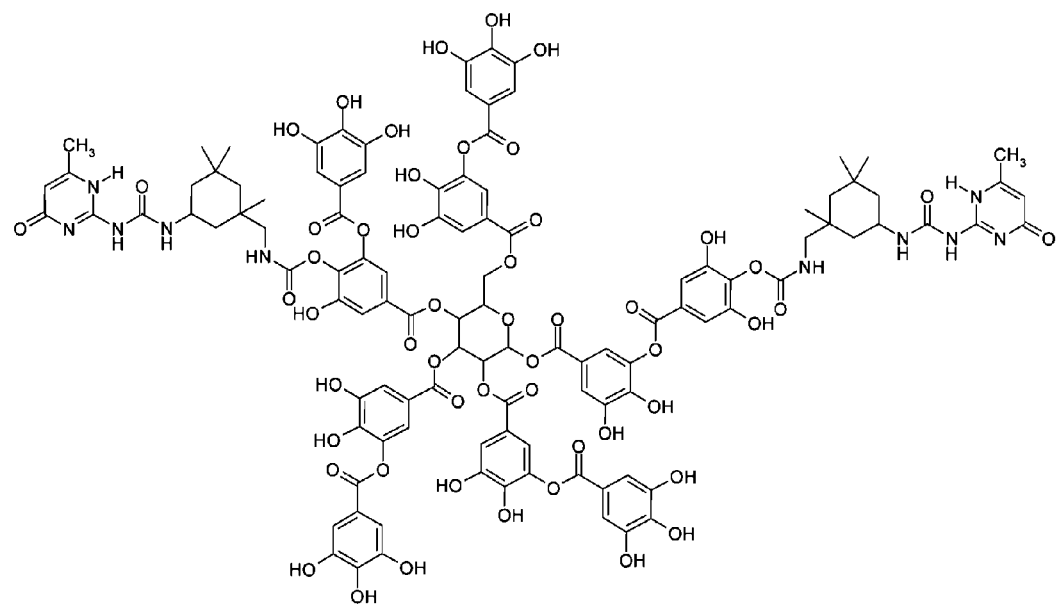
FIG. 9 is the ideal structure of gallotannic compound MCI09-M090.

The synthesis of gallotannic compound MCI09-M090 was performed by slowly adding a mixture containing 200 grams of 1,3-dioxolane and 70.0 grams of Ureido-NCO into a solution containing 100 grams of 1,3-dioxolane, 17.01 grams of gallotannin and 0.10 grams of dibutyl tin dilaurate under nitrogen atmosphere and constant stirring at 50° C. The reaction was then stirred for an additional 10 hours. A sample was withdrawn from the reaction. The FTIR spectrum was recorded on KBr pellet. The —NCO peak at 2210 cm$^{-1}$ was not observed on this FTIR spectrum, which indicated that the reaction was complete. The product was precipitated with 2 liters of water, filtered and washed copiously with water. It was air-dried until constant weight, which produced a pale yellow powder. The idealized chemical structure is shown in FIG. 9.

EXAMPLE 9

Figure 10:
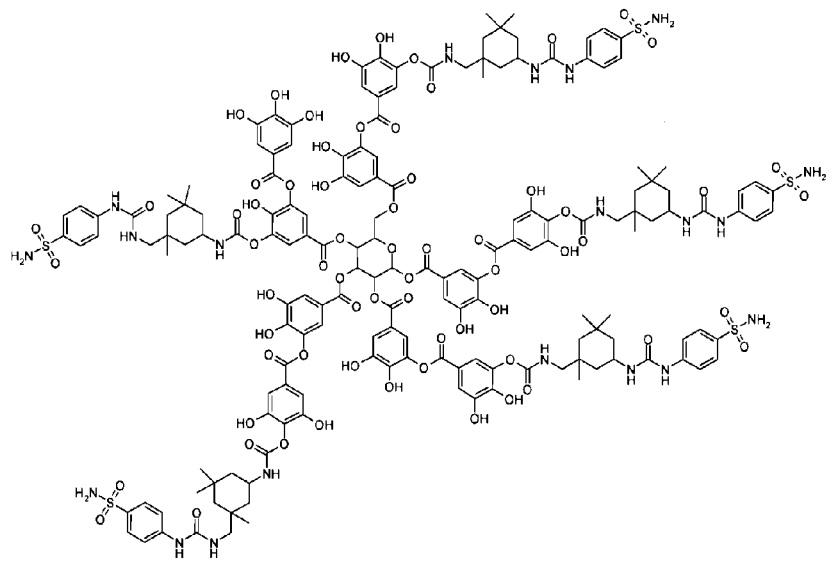
FIG. 10 is the ideal structure of gallotannic compound MCI09-H01.

The synthesis of gallotannic compound MCI09-H01 was performed by slowly adding a mixture containing 200 grams of 1,3-dioxolane and 20.0 grams of Ureido-02 into a solution containing 100 grams of 1,3-dioxolane, 17.01 grams of gallotannin and 0.10 grams of dibutyl tin dilaurate under nitrogen atmosphere and constant stirring at 50° C. The reaction was then stirred for an additional 10 hours. A sample was withdrawn from the reaction. The FTIR spectrum was recorded on KBr pellet. The —NCO peak at 2210 $cm^{-1}$ was not observed on this FTIR spectrum, which indicated that the reaction was complete. The product was precipitated with 2 liters of water, filtered and washed copiously with water. It was air-dried until constant weight, which produced a pale yellow powder. The idealized chemical structure is shown in FIG. 10.

EXAMPLE 10

Figure 11:
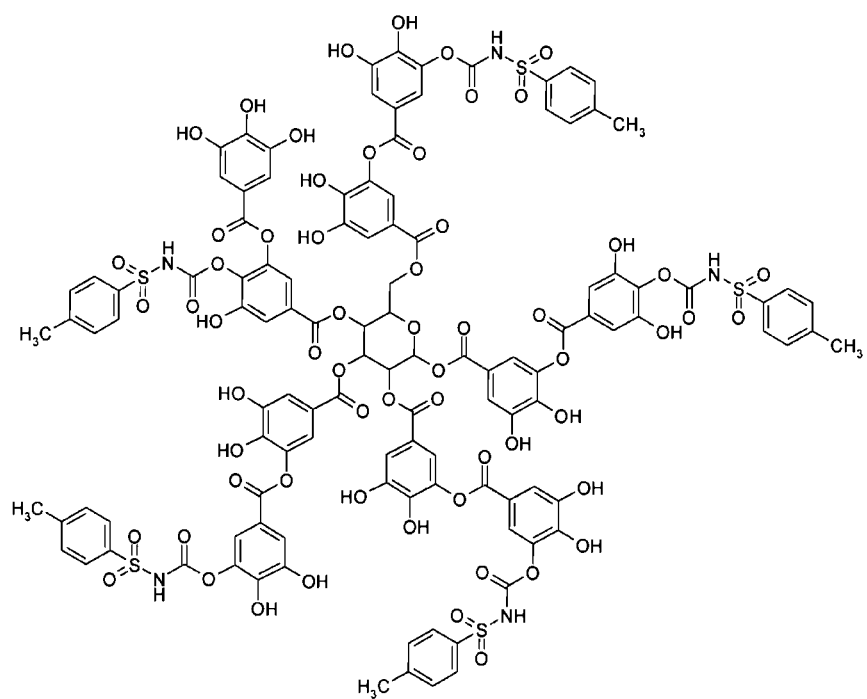
FIG. 11 is the ideal structure of gallotannic compound MCI09-H02.

The synthesis of gallotannic compound MCI09-H02 was performed by slowly adding a mixture containing 200 grams of 1,3-dioxolane and 10.0 grams of p-toluenesulfonyl isocyanate into a solution containing 100 grams of 1,3-dioxolane, 17.01 grams of gallotannin and 0.10 grams of dibutyl tin dilaurate under nitrogen atmosphere and constant stirring at 50° C. The reaction was then stirred for an additional 10 hours. A sample was withdrawn from the reaction. The FTIR spectrum was recorded on KBr pellet. The —NCO peak at 2210 $cm^{-1}$ was not observed on this FTIR spectrum, which indicated that the reaction was complete. The product solution is ready for use in coating formulation. The idealized chemical structure is shown in FIG. 11.

EXAMPLE 11

The synthesis of gallotannic compound MCI09-H03 was performed as follows. In a first reaction flask, a mixture containing 200 grams of 1,3-dioxolane and 10.0 grams of 2-chloroethyl isocyanate was added to a solution containing 100 grams of 1,3-dioxolane, 17.01 grams of gallotannin and 0.10 grams of dibutyl tin dilaurate under nitrogen atmosphere and constant stirring at 50° C. The reaction was then stirred for 10 hours. A sample was withdrawn from the reaction. The FTIR spectrum was recorded on KBr pellet. The —NCO peak at 2210 $cm^{-1}$ was not observed on this FTIR spectrum, which indicated that the reaction was complete.

Figure 12:
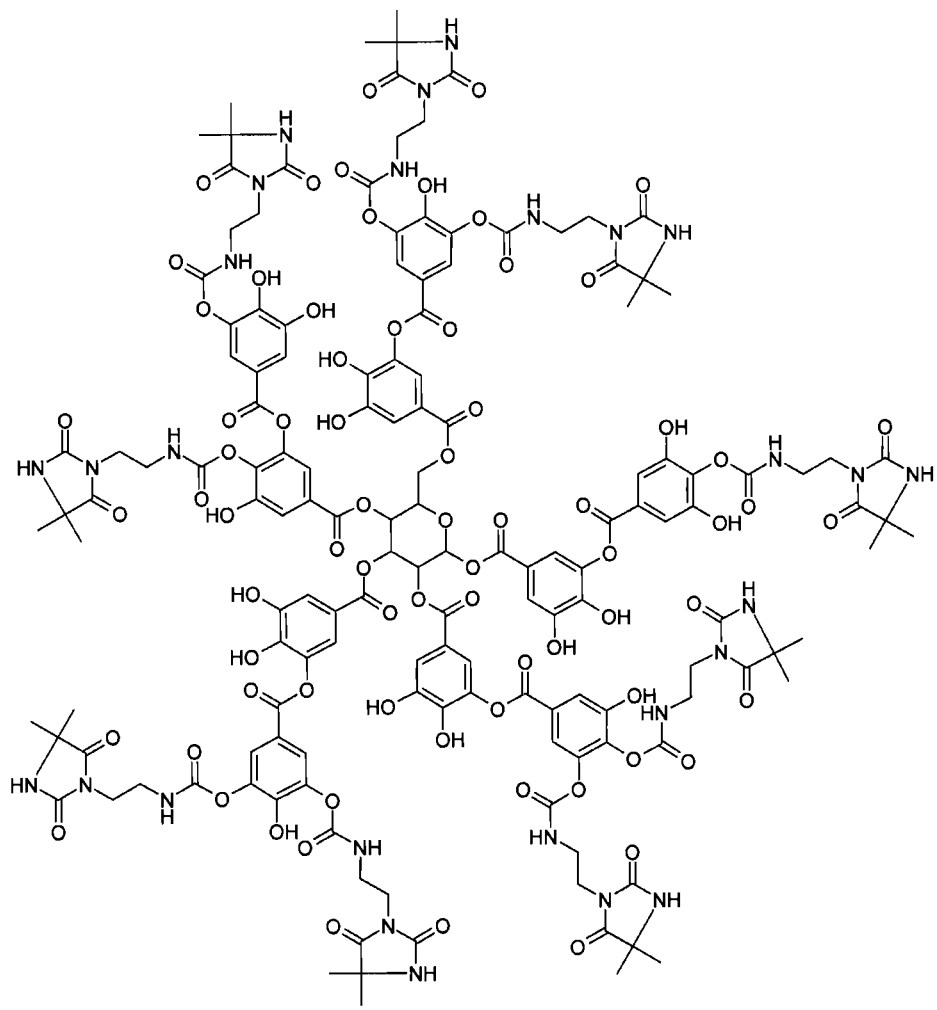
FIG. 12 is the ideal structure of gallotannic compound MCI09-H03.

In another reaction flask, 3.00 grams of potassium hydroxide was added into a solution containing 50 grams of ethanol and 11.6 grams of 5,5-dimethylhydantoin. The reaction mixture was stirred at 40° C. for 4 hours. It was then cooled to room temperature. Then, the obtained mixture was added to that in the first reaction flask. The mixture was heated at 40° C. for 10 hours. The product was precipitated with 2 liters of water, filtered and washed copiously with water. It was air-dried until constant weight, which produced a pale yellow powder. The idealized chemical structure is shown in FIG. 12.

Gallotannic Dendrimers

EXAMPLE 12

Figure 13:
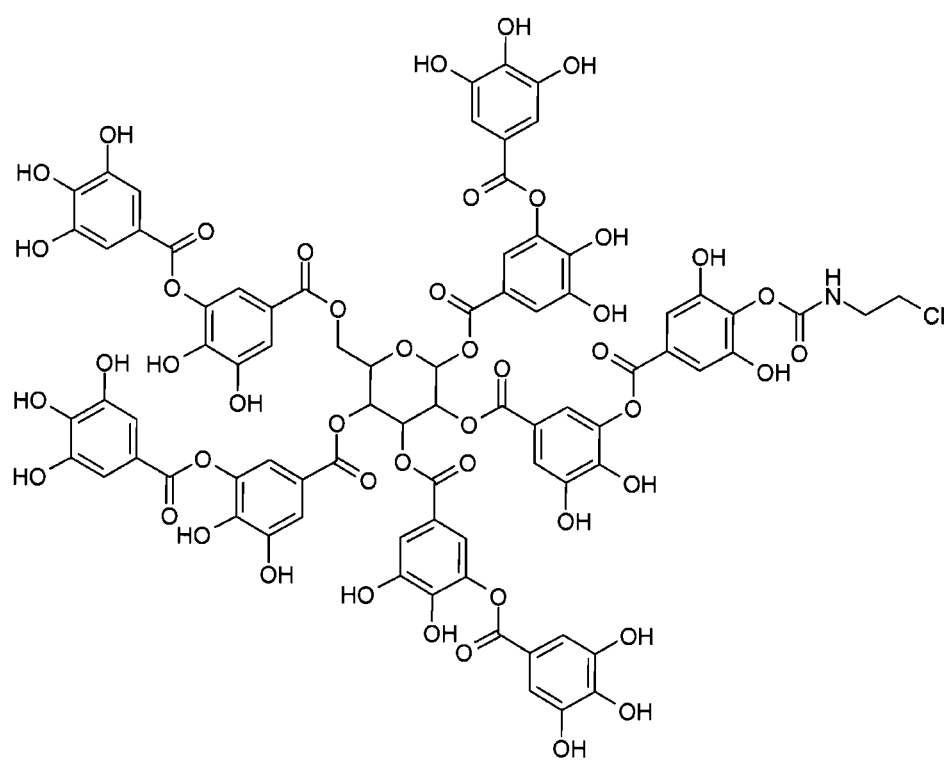
FIG. 13 is the ideal structure of intermediate MCI09-040.

Gallotannic compound MCI09-M040 was first prepared as an intermediate. This was performed by slowly adding 50 grams of a 1,3-dioxolane solution containing 5.25 grams of 2-chloroethyl isocyanate and 0.05 grams of dibutyl tin dilaurate into 350 grams of a 1,3-dioxolane solution containing 85.05 grams of gallotannin under nitrogen atmosphere and constant stirring at 60° C. The reaction was completed after 5 hours as indicated by the disappearance of the —NCO peak at 2270 $cm^{-1}$ on the FTIR spectrum. The ideal structure of this compound is shown in FIG. 13.

Figure 14:
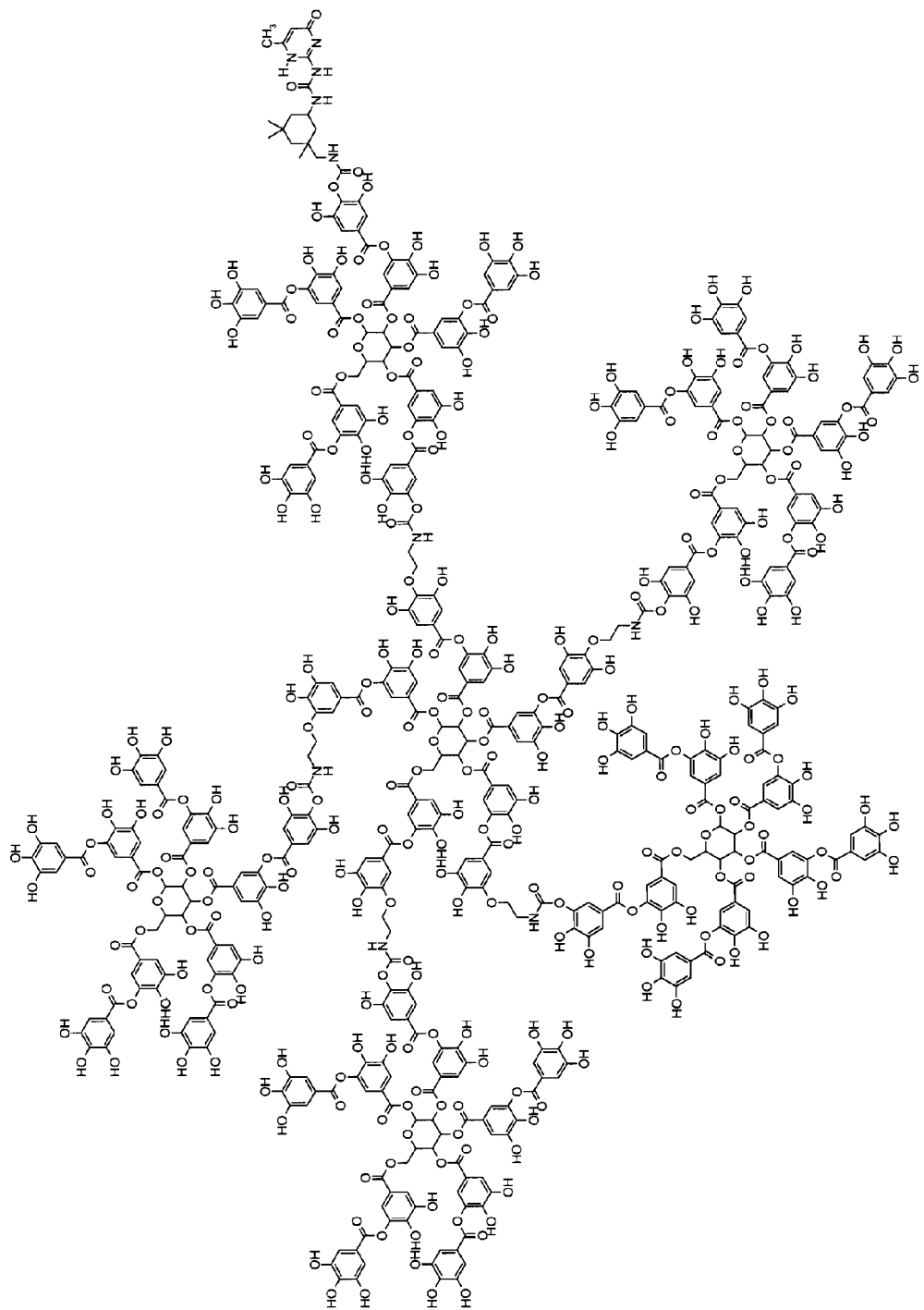
FIG. 14 is the ideal structure of gallotannic dendrimer MCI09-D001.

The synthesis of gallotannic dendrimer MCI09-D001 was performed by slowly adding 2.00 grams of sodium hydride (60% in mineral oil) into a mixture containing 300.0 grams of 1,3-dioxolane and 17.0 grams of gallotannin under nitrogen atmosphere and constant stirring at 50° C. When the hydrogen bubbles disappeared, a mixture containing 400 grams of 1,3-dioxolane and 90.30 grams of gallotannic compound MCI09-M040 was slowly added into the reaction mixture and stirring continued at 50° C. for an additional 10 hours. Then, a mixture containing 100 grams of 1,3-dioxolane, 34.7 grams of Ureido-NCO and 0.1 grams of dibutyl tin dilaurate was slowly added into the reaction mixture. Stirring continued at 60° C. for 10 hours. The FTIR spectrum of the reaction mixture showed no —NCO group at 2210 $cm^{-1}$, which indicated that the reaction was complete. The product was precipitated in 5 liters of water an then filtered and washed copiously with water. It was then air-dried until constant weight to produce a pale yellow powder. The idealized chemical structure of gallotannic dendrimer MCI09-D001 is shown in FIG. 14.

Synthesis of Gallotannic Compounds for Use in Positive Plates
Gallotannic Compounds with Chromophores
Molecular NIR Chromophores

EXAMPLE 13

Figure 15:
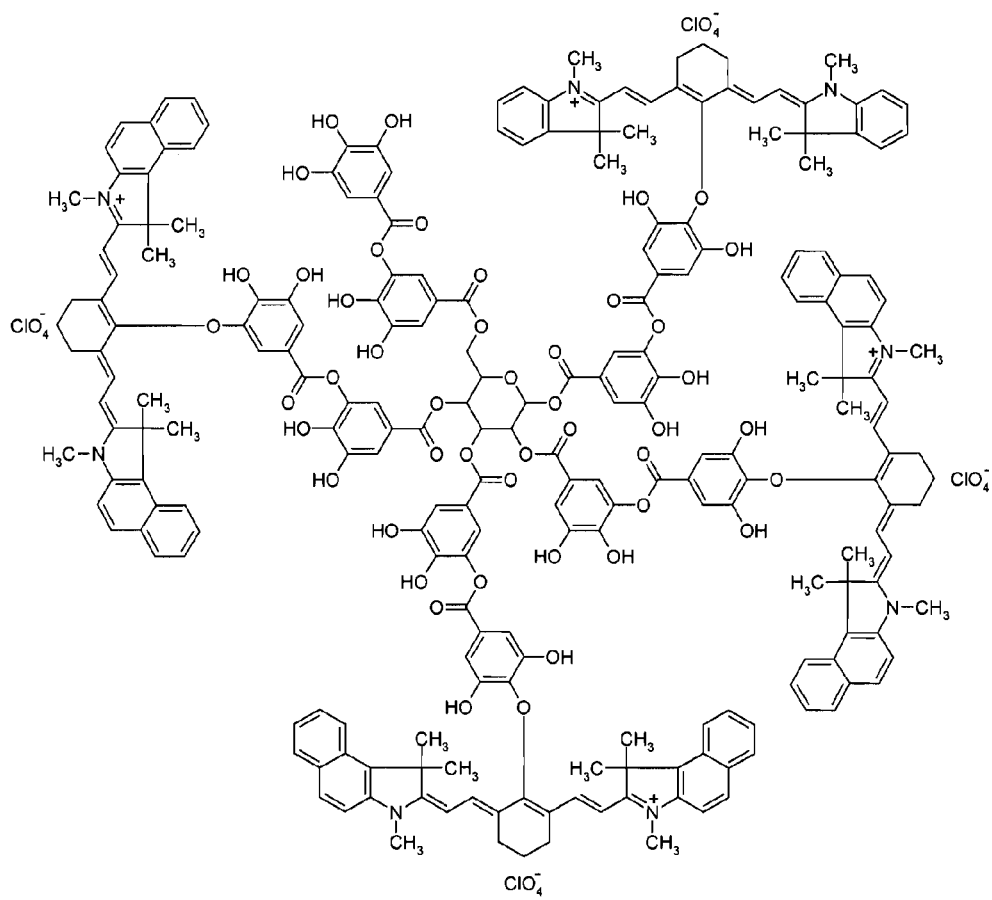
FIG. 15 is the ideal structure of gallotannic compound MCI09-M100.

Gallotannic compound MCI09-M100, which comprises a near infrared absorbing molecular chromophore, was synthesized by slowly adding 90 grams of sodium hydride (60% in mineral oil, available from Sigma-Aldrich, Canada) into a reaction mixture containing 5,000 grams of DMSO and 1,000 grams of gallotannin under nitrogen atmosphere and constant stirring. When the hydrogen gas bubbles disappeared, 375 grams of ADS775PI and 1125 grams of ADS830AT were slowly added into the reaction mixture. The mixture was stirred at 60° C. for an additional 20 hours. The dark green product was precipitated in 20 liters of water containing 0.5 M of perchloric acid, and then filtered and washed copiously with water. The near infrared absorbing gallotannic compound, MCI09-M100, was air-dried until constant weight. Its UV-Vis-NIR spectrum in methanol showed a strong near infrared absorption band at 800 nm, which indicated that the NIR chromophore was covalently bound to the gallotannin. The idealized chemical structure of MCI09-M100 is shown in the FIG. 15.

EXAMPLE 14

Figure 16:
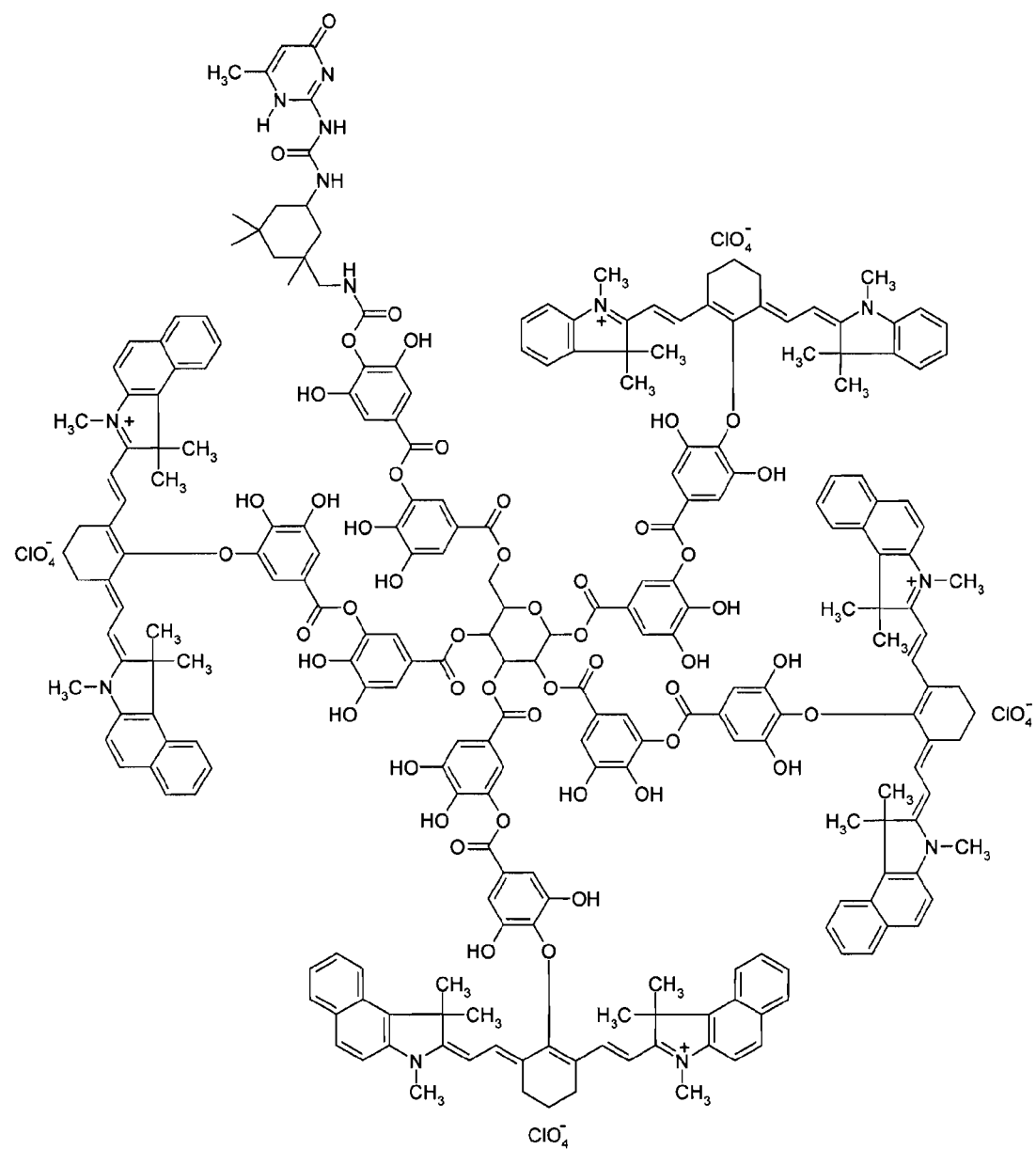
FIG. 16 is the ideal structure of gallotannic compound MCI09-M102.

Gallotannic compound MCI09-M102, shown in the FIG. 16, was prepared in a similar manner.
Polymeric NIR Chromophores

EXAMPLE 15

Figure 17:
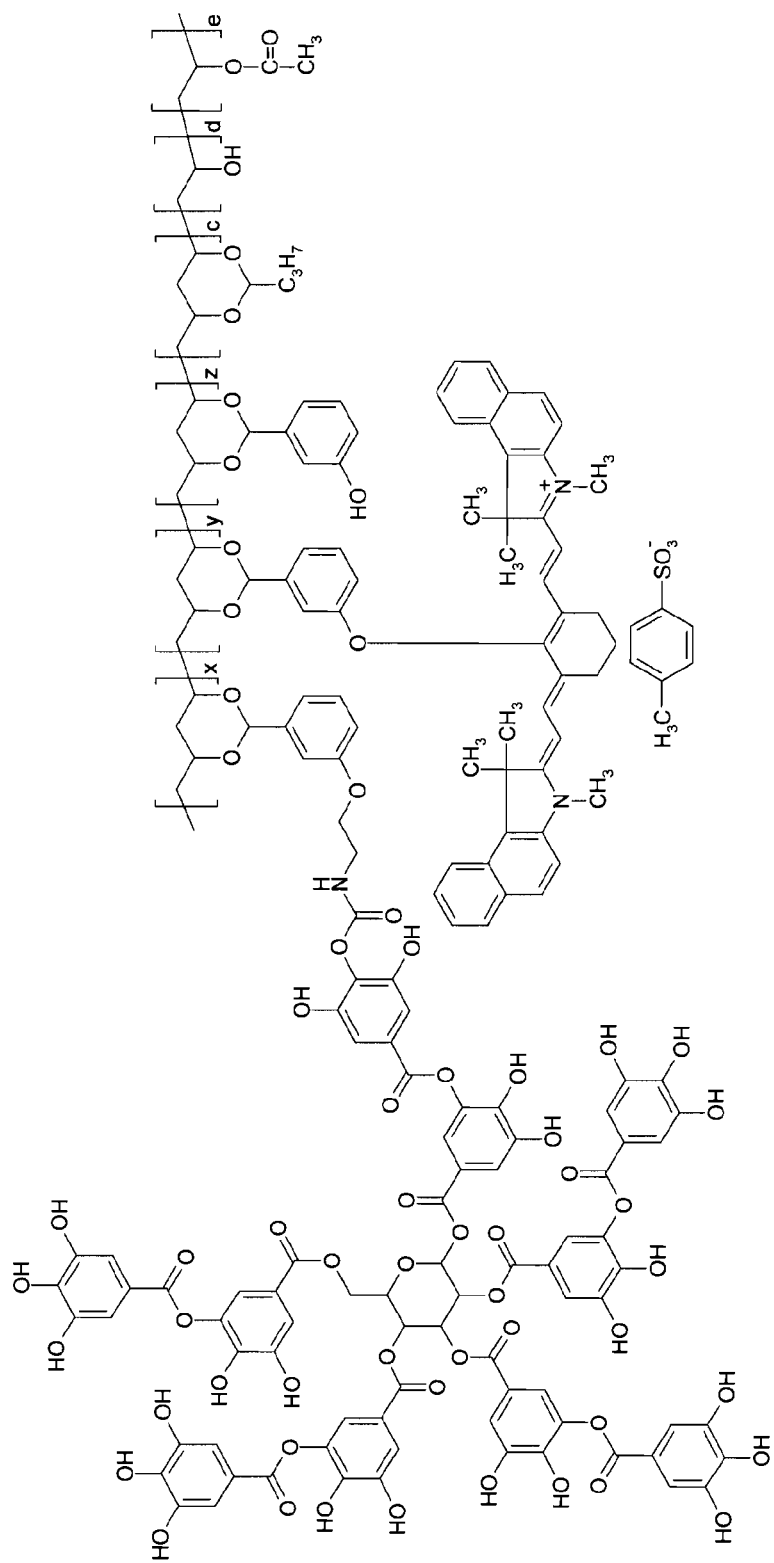
FIG. 17 is the ideal structure of gallotannic compound MCI09-P200.

Gallotannic compound MCI09-P200 was synthesized by slowly adding 1.20 grams of sodium hydride (60% in mineral oil) into 270 grams of DMSO in which were dissolved 30.0 grams of MCI09-P009 acetal copolymer under nitrogen atmosphere and constant stirring at 40° C. When the hydrogen gas bubbles disappeared, a mixture of 5.40 grams of gallotannic compound MCI09-M040 and 30 grams DMSO was slowly added into the reaction mixture. After 5 hours stirring at 60° C., a sample of the reaction mixture was withdrawn for GPC analysis, which indicated that the MCI09-040 was covalently bound to the backbone of MCI09-P009. Then, 1.70 grams of ADS830AT were slowly added into the reaction mixture. Stirring was continued at 60° C. for an additional 16 hours. The average molecular weight of MCI09-009 increased from around 32,000 to around 42,000, which also indicated that MCI09-040 was covalently bonded to the MCI09-009 backbone. The dark green solid product was precipitated in 2 liters of water and then filtered and washed copiously with water. The gallotannic compound was air-dried until constant weight. The ideal structure of MCI09-P200 is shown in FIG. 17, wherein x=3, y=3, z=269, c=76, d=74 and e=7.

Figure 18:
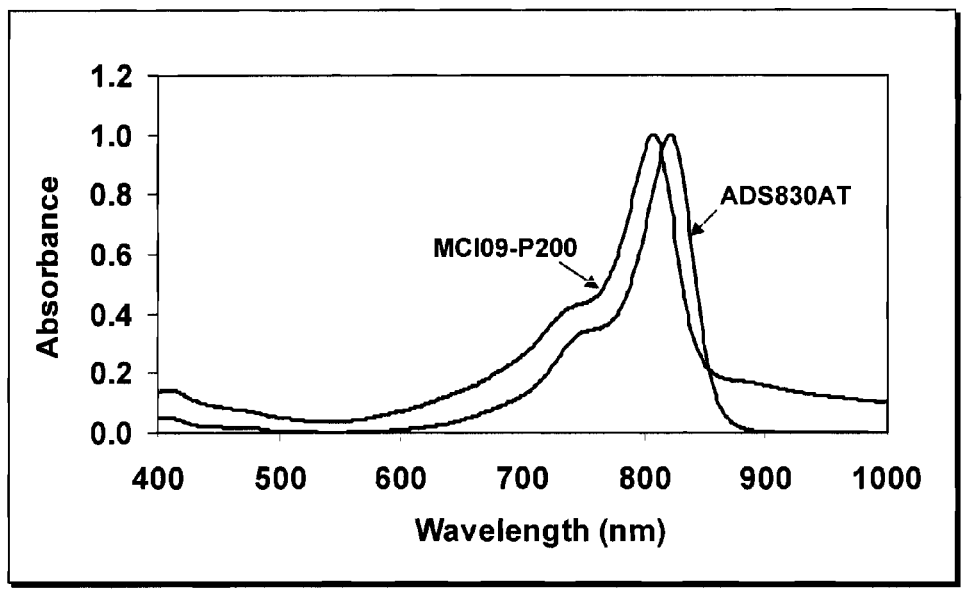
FIG. 18 shows the UV-Vis-NIR spectra of MCI09-P200 and near infrared dye ADS830AT in 2-methoxy propanol.

FIG. 18 shows the UV-Vis-NIR curves of MCI09-P200 and ADS830AT in 2-methoxy-propanol solutions. The maximum absorption peaks of MCI09-P200 and ADS830AT were found at 800 nm and 815 nm. The shift in maximum absorption peak to shorter wavelengths indicates that the near infrared chromophore is covalently bound to acetal copolymer.

EXAMPLE 16

Figure 19:
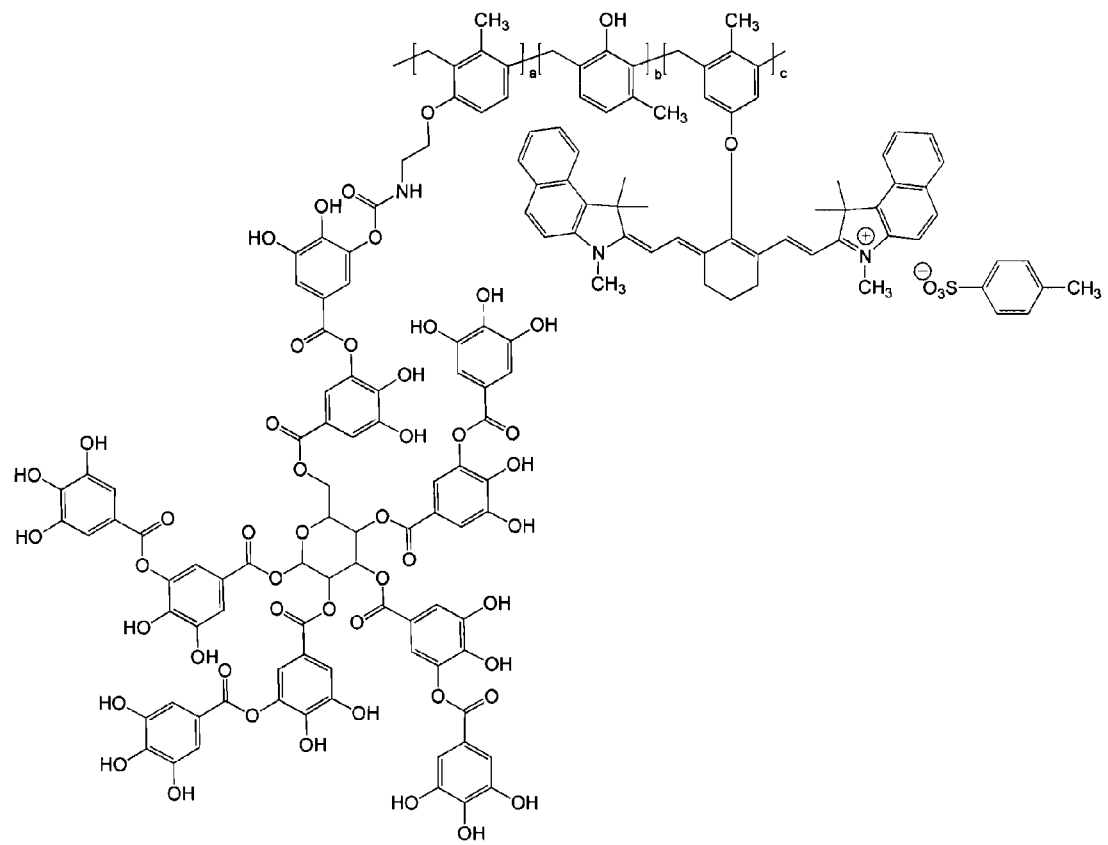
FIG. 19 is the ideal structure of gallotannic compound MCI09-P204.

Gallotannic compound MCI09-P204, shown in the FIG. 19, wherein a is 0.01, b is 0.95, and c is 0.04, was prepared in a similar manner.

UV Chromophores

EXAMPLE 17

Figure 20:
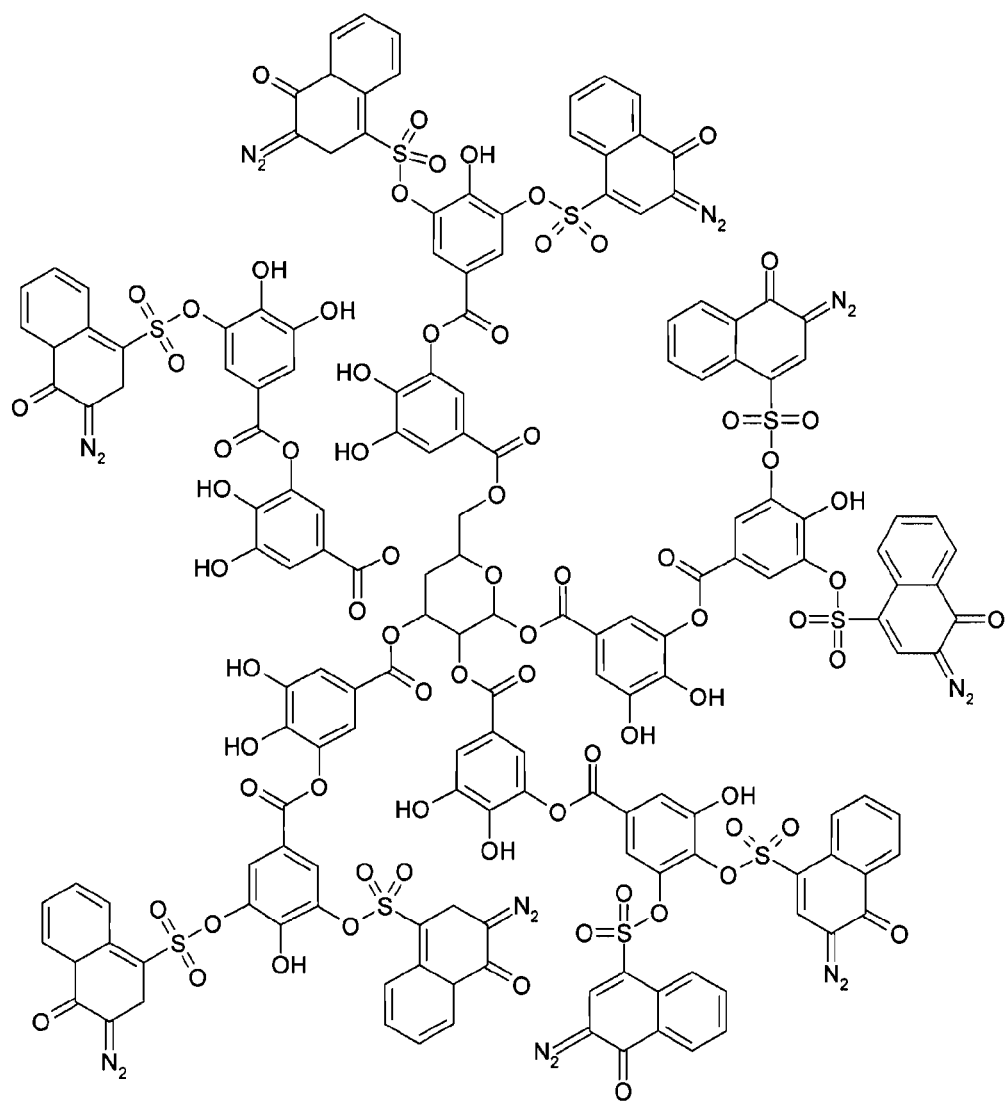
FIG. 20 is the ideal structure of gallotannic compound Gallo-NDQ.

The synthesis of Gallo-NDQ was performed by slowly adding 8.20 grams N-methylmorpholine into 200 grams 1,3-dioxolane, in which were dissolved 14.8 grams of (1,2-napthoquinone-2-diazide)-4-sulfonylchloride and 17.0 grams of gallotannin under nitrogen atmosphere and constant stirring at 25° C. After 5 hours, the product was precipitated in 2 liters of water containing (0.1 N) hydrochloric acid. The yellowish solid powder was filtered, washed copiously with water and air-dried to constant weight. The idealized chemical structure of Gallo-NDQ is shown in FIG. 20.

Gallotannic Compounds with Binders

EXAMPLE 18

Figure 21:
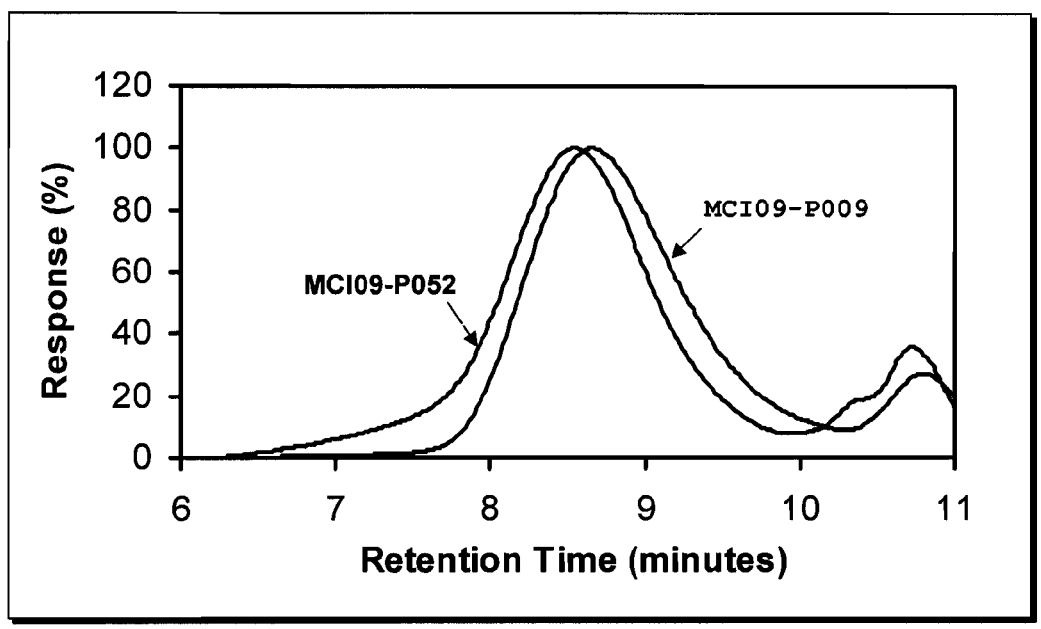
FIG. 21 shows the GPC curves of MCI09-009 and MCI09-052.
Figure 22:
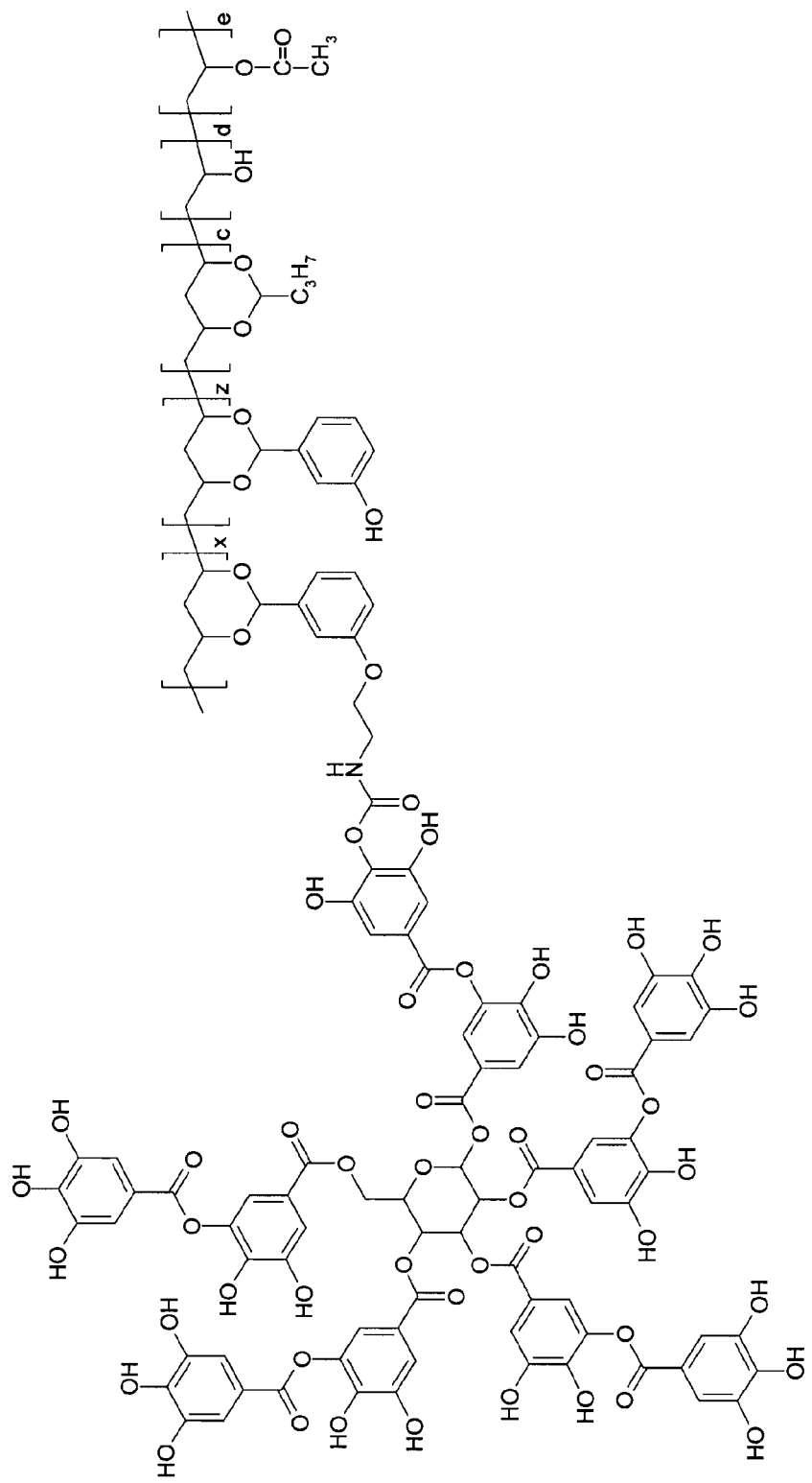
FIG. 22 is the ideal structure of gallotannic compound MCI09-P052.

Gallotannic compound MCI09-P052 was synthesized by slowly adding 0.40 grams of sodium hydride (60% in mineral oil) into 90 grams of DMSO in which were dissolved 10 grams of the MCI09-P009 acetal copolymer under nitrogen atmosphere and constant stirring at 40° C. When the hydrogen gas bubbles disappeared, a mixture of 10.8 grams of gallotannic compound MCI09-M040 and 10 grams DMSO was slowly added into the reaction mixture. Stirring continued at 60° C. for an additional 20 hours. FIG. 21 shows the GPC curves of MCI09-P009 before and after reaction with 6 equivalents of MCI09-M040. The average molecular weight of MCI09-P009 increased from 32,000 g/mole to around 48,000 g/mole, which indicated that MCI09-M040 was covalently bound to the backbone of the MCI09-P009 copolymer. The light pale solid product was precipitated in 2 liters of water, filtered and washed copiously with water. The gallotannic compound was then air-dried until constant weight. The idealized structure of MCI09-P052 is shown in FIG. 22, wherein x=9, z=269, c=76, d=74 and e=7.

EXAMPLE 19

Figure 23:
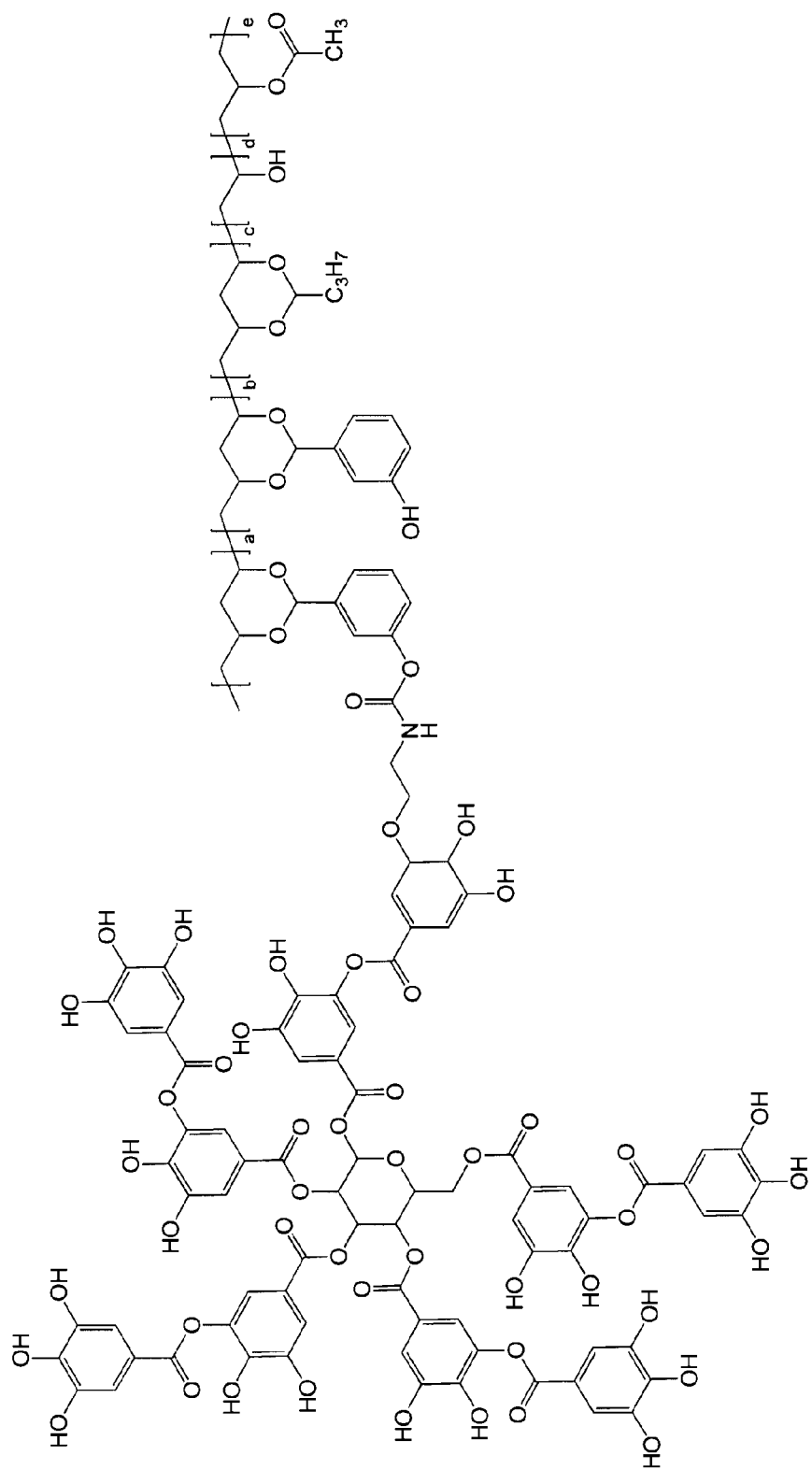
FIG. 23 is the ideal structure of gallotannic compound MCI09-P054.

Gallotannic compound MCI09-P054, shown in the FIG. 23 wherein a=9, b=269, c=76, d=74 and e=7, was prepared in a similar manner.

EXAMPLE 20

Figure 24:
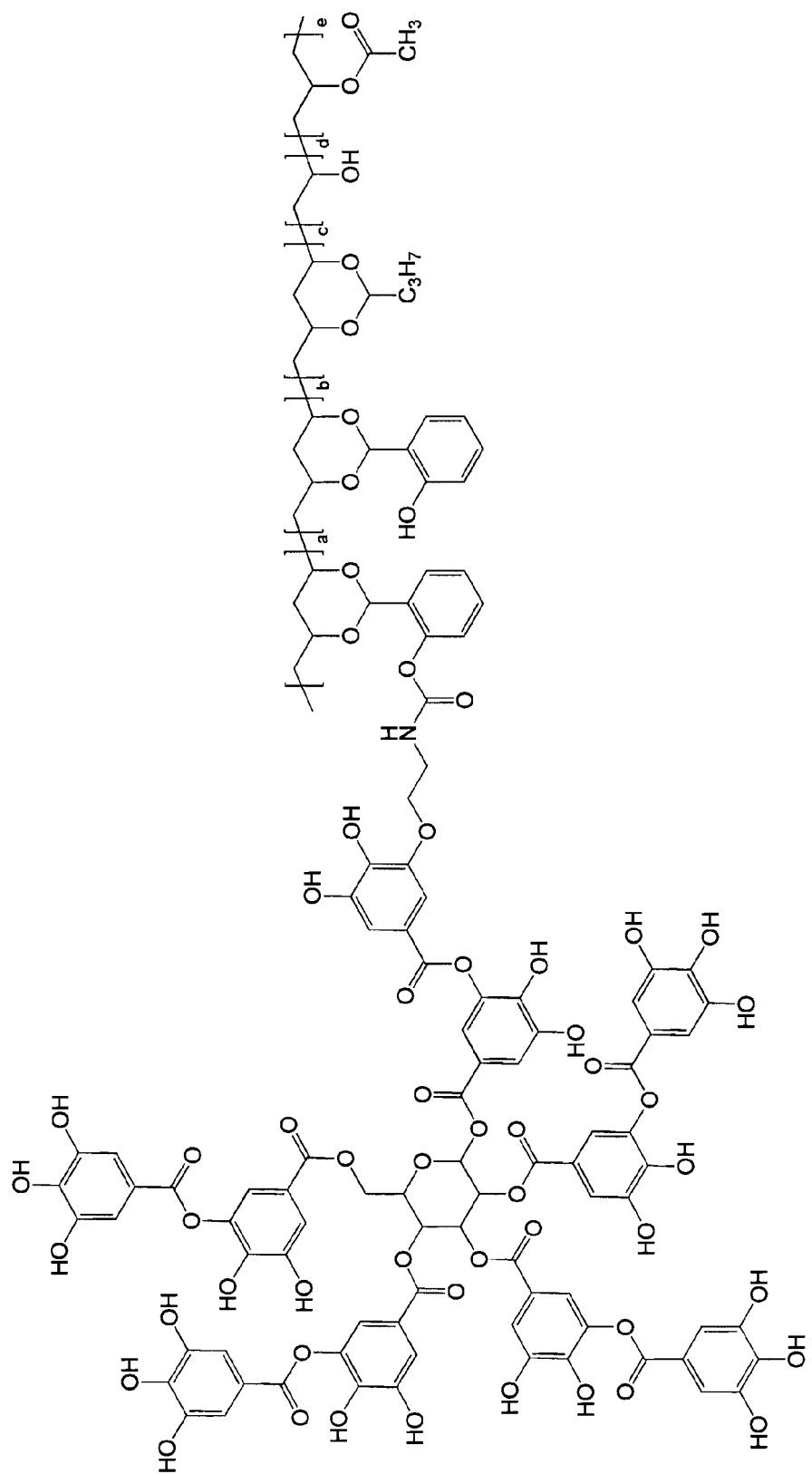
FIG. 24 is the ideal structure of gallotannic compound MCI09-P056.

Gallotannic compound MCI09-P056, shown in the FIG. 24, wherein a is 3, b is 300, c is 83, d is 81 and e is 8 was prepared in a similar manner.

EXAMPLE 21

Figure 25:
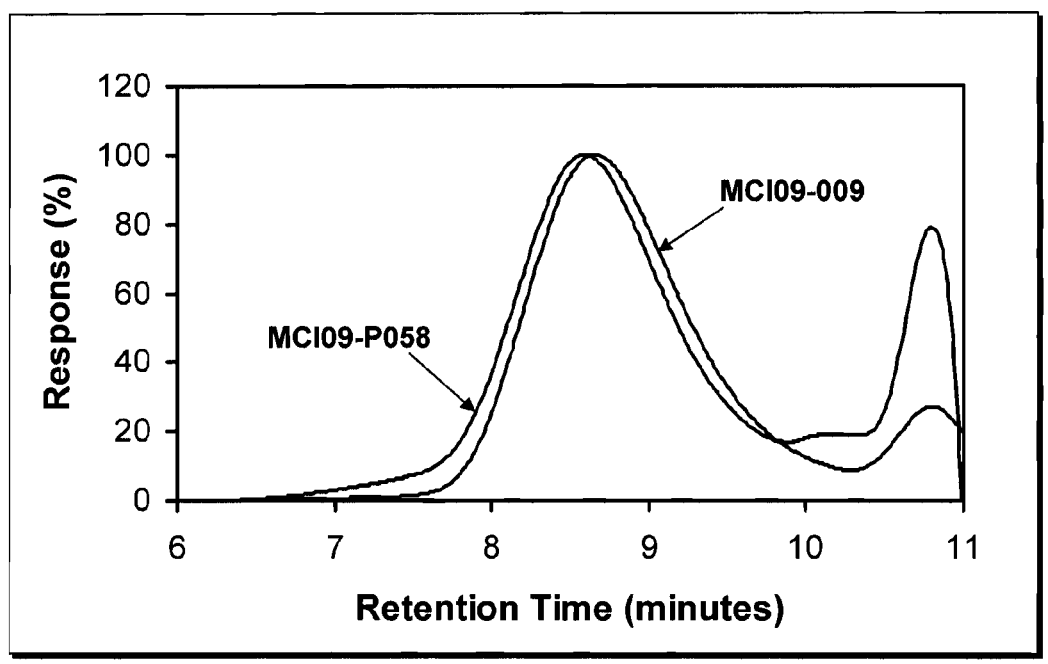
FIG. 25 shows the GPC curves of MCI08-P020 before and after reaction with 3 equivalent of MCI09-M040.
Figure 26:
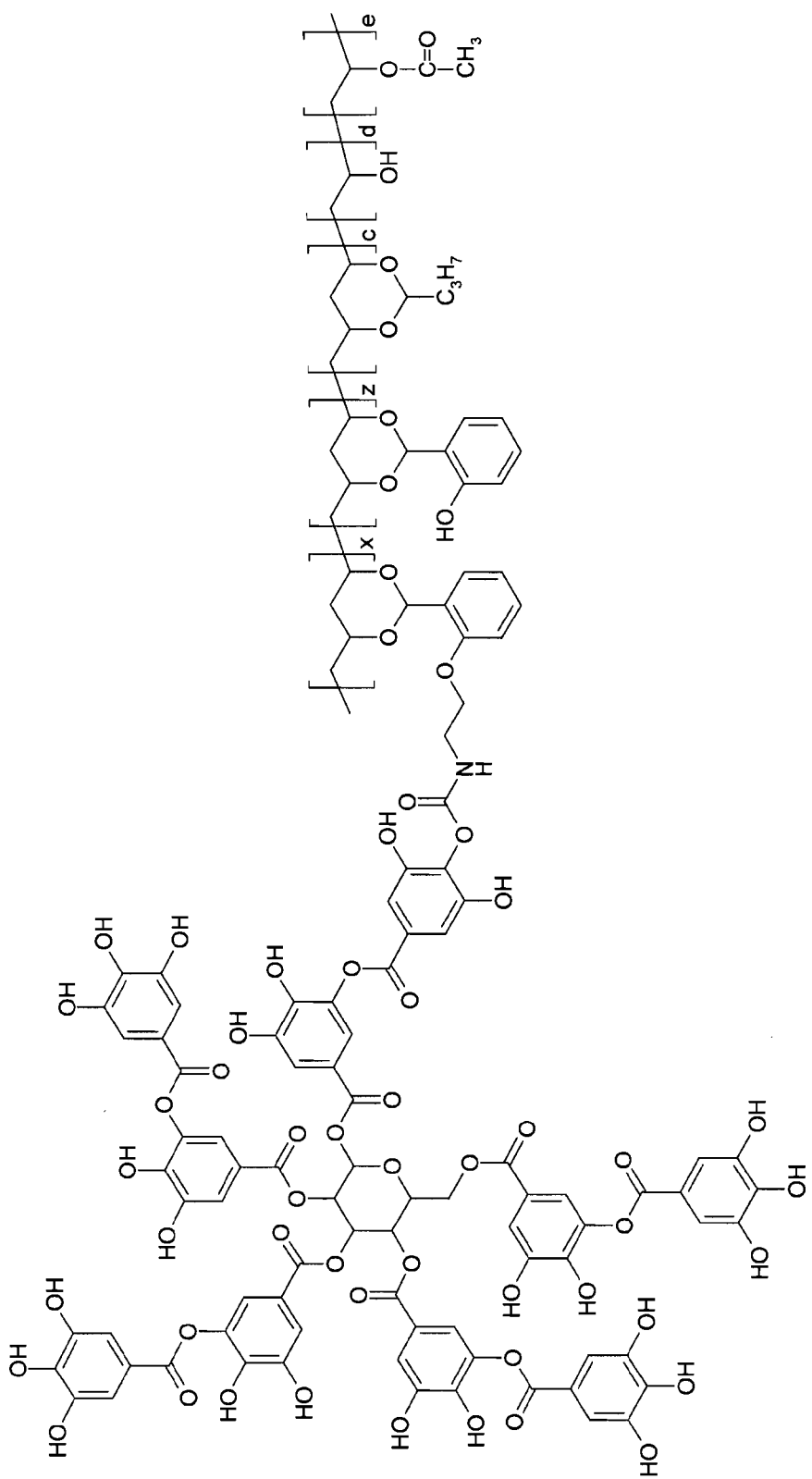
FIG. 26 is the ideal structure of gallotannic compound MCI09-P058.

Gallotannic compound MCI09-P058 was synthesized by slowly adding 0.40 grams of sodium hydride (60% in mineral oil) into 90.0 grams of DMSO in which were dissolved 10.0 grams of MCI08-P020 acetal copolymer under nitrogen atmosphere and constant stirring at 40° C. When the hydrogen gas bubbles disappeared, a mixture of 5.40 grams of gallotannic compound MCI09-M040 and 10.0 grams DMSO was slowly added into the reaction mixture. Stirring continued at 60° C. for an additional 20 hours. FIG. 25 shows the GPC curves of MCI08-P020 before and after reaction with 3 equivalents of MCI09-M040. The average molecular weight of MCI09-P09 increased from 32,000 g/mole to around 48,000 g/mole, which indicated that the MCI09-M040 was covalently bound to the backbone of the MCI08-P020 copolymer. The light pale solid product was precipitated in 2 liters of water and then filtered and washed copiously with water. The gallotannic compound was air-dried until constant weight. The idealized structure of MCI09-P058 is shown in FIG. 26, wherein x=3, z=300, c=83, d=81 and e=8.

Gallotannic Compounds with Binders and NIR chromophore

EXAMPLE 22

Figure 27:
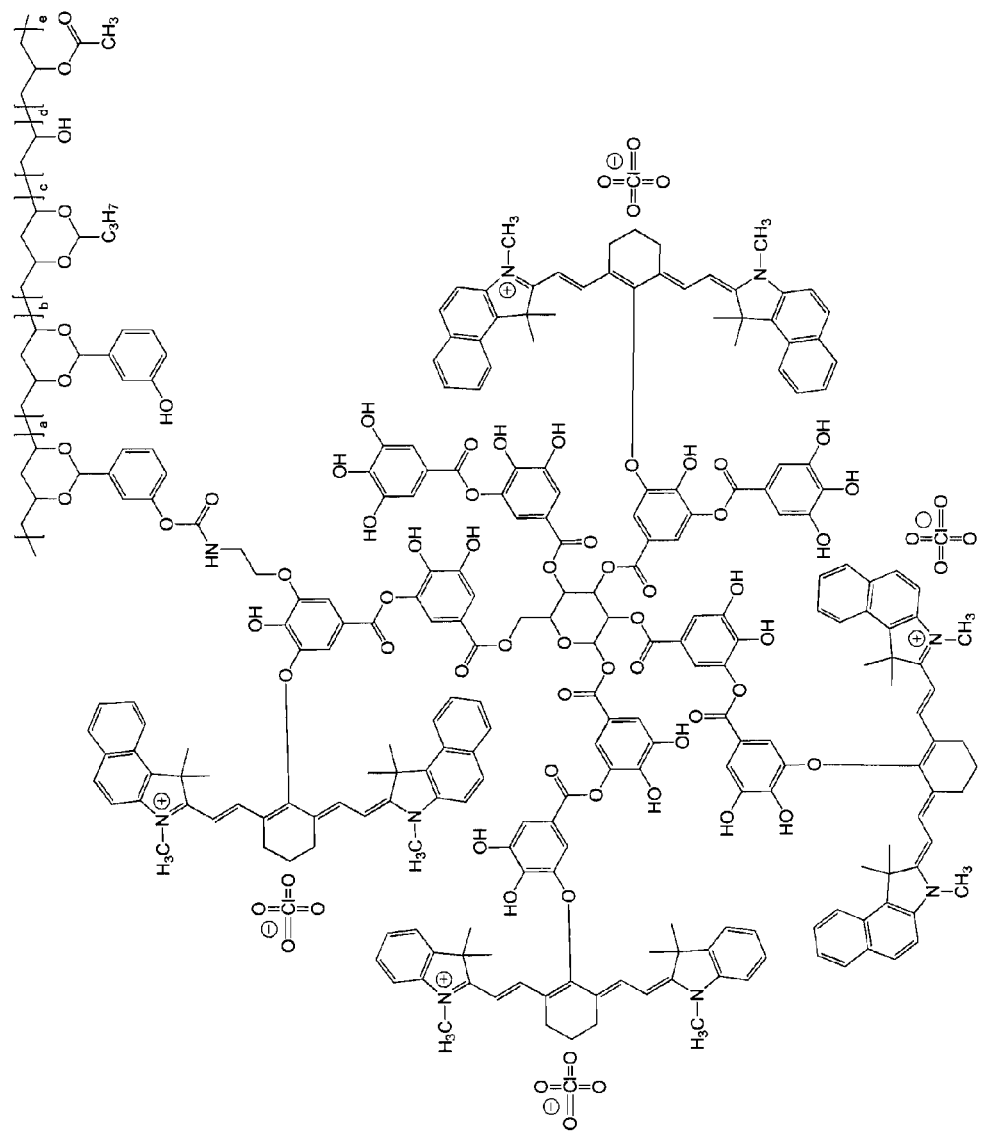
FIG. 27 is the ideal structure of gallotannic compound MCI09-P208.

Gallotannic compound, MCI09-P208, which is shown in FIG. 27 wherein a=9, b=269, b=76, d=74 and e=7, was synthesized by slowly adding 10 grams of sodium hydride (60% in mineral oil, available from Sigma-Aldrich, Canada) into a reaction mixture containing 1,000 grams of DMSO and 15.7 grams of gallotannin under nitrogen atmosphere and constant stirring. When the hydrogen gas bubbles disappeared, 3.75 grams of 2-[2-[2-chloro-3-[2-(1,3-dihydro-1,3,3-trimethyl-2H-indolenine-2-ylidene)-ethylidene]-1-cyclohexen-1-yl]-ethenyl]-1,3,3-trimethyl-1H-indolium iodide and 11.25 grams of 2-[2-[2-chloro-3-[2-(1,3-dihydro-1,3,3-trimethyl-2H-benz[e]indol-2-ylidene)-ethylidene]-1-cyclohexen-1-yl]-ethenyl]-1,3,3-trimethyl-1H-benz[e]indolium 4-methyl-benzenesulfonate were slowly added into the reaction mixture. Then, 5,000 grams of DMSO dissolving with 980 grams of MCI09-030 were slowly added into the reaction mixture. Stirring continued at 60° C. for an additional 20 hours. The dark green product was precipitated in 20 liters of water containing 0.5 M of perchloric acid, and then filtered and washed copiously with water. The gallotannic compound MCI09-P208 was air-dried until constant weight. The UV-Vis-NIR spectrum of this compound in methanol showed a strong near infrared absorption band at 800 nm, which indicated that the near infrared absorption chromophore was covalently bound to the gallotannin.

EXAMPLE 23

Figure 28:
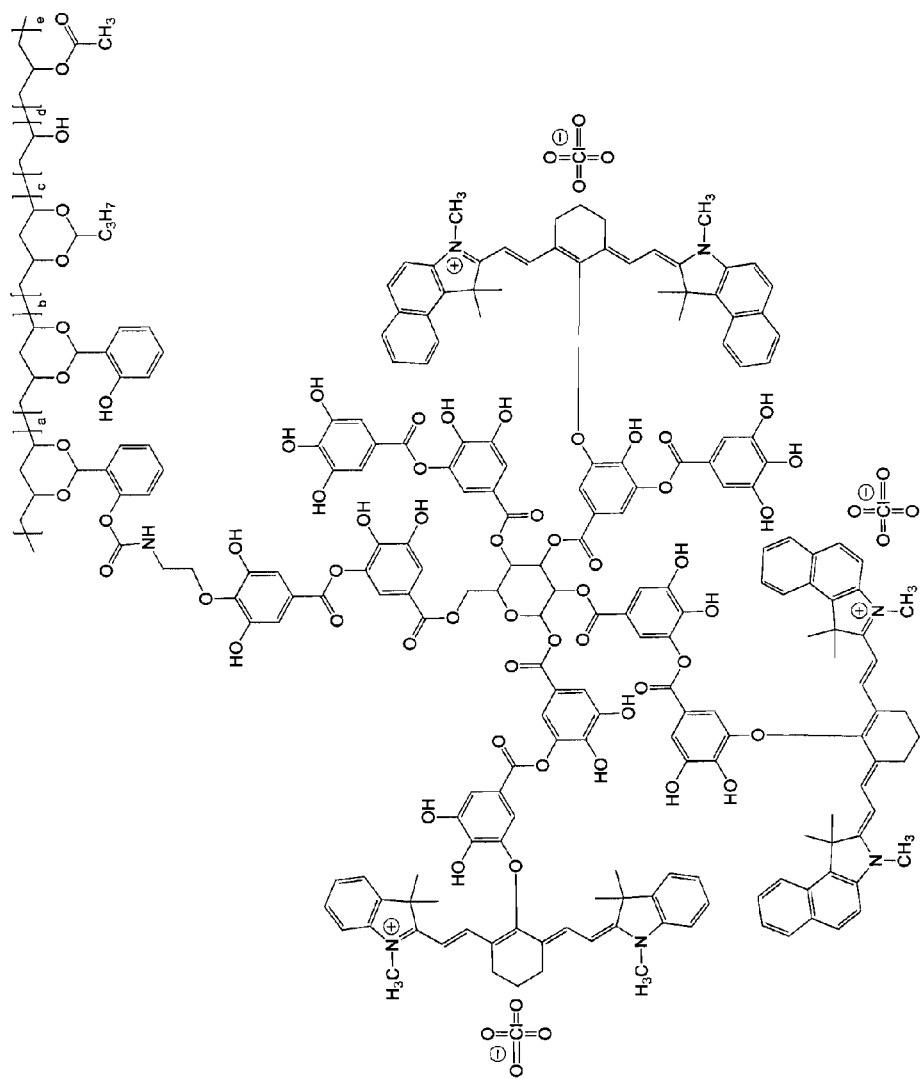
FIG. 28 is the ideal structure of gallotannic compound MCI09-P202.

Gallotannic compound MCI09-P202, shown in the FIG. 28, wherein a is 3, b is 300, c is 83, d is 81 and e is 8 was prepared in a similar manner.

EXAMPLE 24

Figure 29:
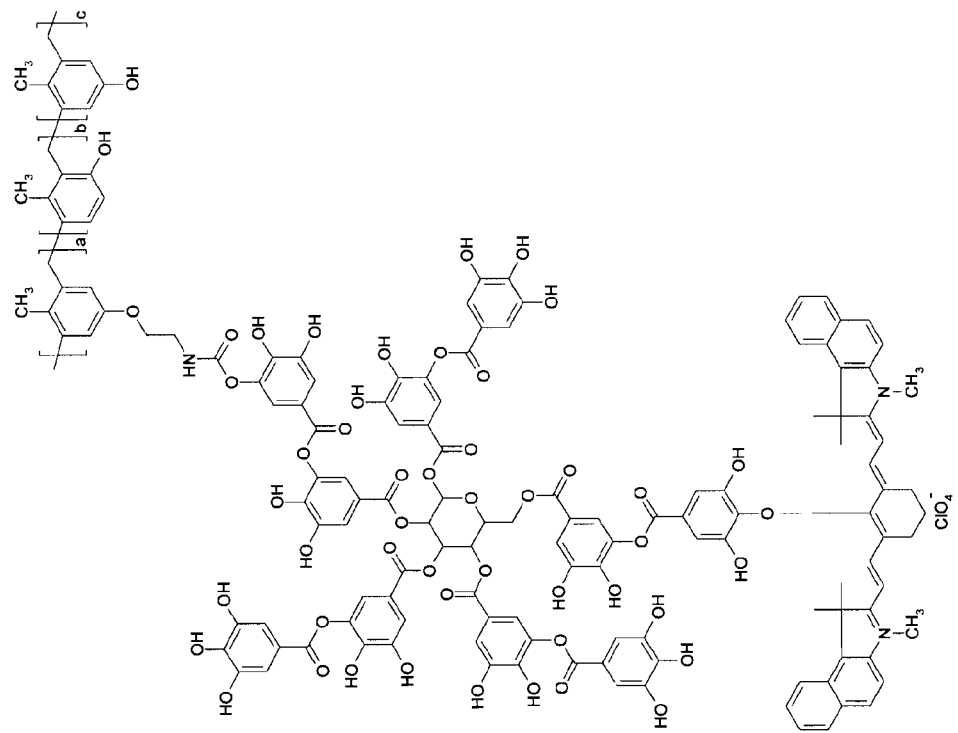
FIG. 29 is the ideal structure of gallotannic compound MCI09-P206.

Gallotannic compound MCI09-P206, shown in the FIG. 29, wherein a is 0.04, b is 0.30, and c is 0.66 was prepared in a similar manner.

Synthesis of Polymeric Particles for Use in Lithographic Printing Plates

The syntheses of the polymeric particles were performed in a 4 necks glass reactor equipped with a water condenser, a mechanical stirrer, a dropping funnel and a nitrogen or oxygen gas inlet. The molecular structures of the obtained materials were determined by proton NMR and FTIR spectroscopy. The average molecular weight of the copolymers obtained was determined by size exclusion chromatography (SEC), using N,N-dimethylformamide (DMF) solution and calibrated with polystyrene standards. The particle size of polymeric particles was determined by the particle size analyzer (available from Brookhaven Instruments Corporation, Model 90PLUS).

Figure 30:
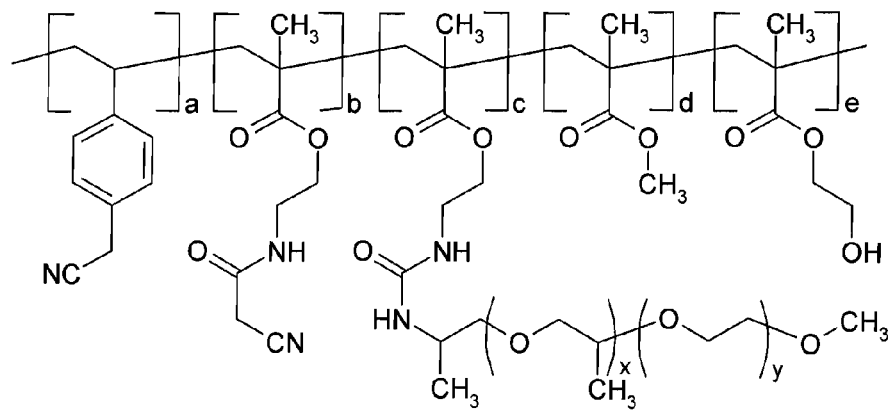
FIG. 30 is the ideal structure of polymeric particle PP-01.

Polymeric particle PP-01 comprising the polymer shown in FIG. 30 was synthesized by heating a mixture of 80 grams of n-propanol and 45 grams of de-ionized water in which were dissolved 4.50 grams of CN-M05 monomer, 8.60 grams of CN-M02, 4.0 grams of cyanoacetamide-ethyl methacrylate, 2.60 grams of HEMA, and 11.21 grams of methacrylate, in a 1 L 4-neck flask at 75° C. under a nitrogen atmosphere with constant stirring. After heating for 30 minutes, 0.4 g of V59 was added into the reaction mixture. The solution became hazy within 30 minutes of polymerization. After polymerization for 10 hours at 75° C., another 0.5 g of V59 was added into the reaction mixture and the polymerization was continued for another 14 hours. Air was introduced into the reaction mixture and stirring at 75° C. was continued for an additional 2 hours to terminate the polymerization. The molecular weight of PP-01 was determined in tetrahydrofuran solution to be around 43,000 with polymer dispersity of 2.5. The particle size was determined to be around 240 nm with dispersity of 0.15. The ideal structure of polymer in PP-01 is shown in FIG. 30, wherein a=0.30, b=0.10, c=0.01, d=0.58, e=0.01, x=1 and y=9.

Figure 31:
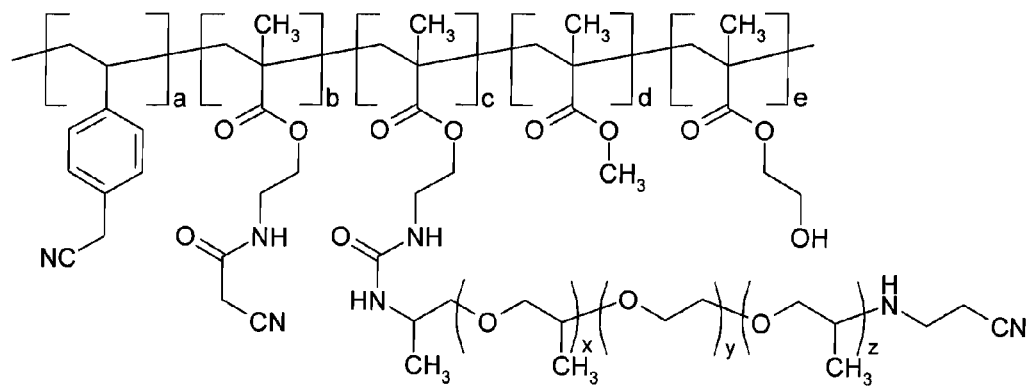
FIG. 31 is the ideal structure of polymeric particle PP-02.

The synthesis of polymeric particle PP-02 was performed similarly to the synthesis of polymeric particle PP-01, except that 4.5 grams of CN-M05 was replaced with 4.80 grams of CN-M06. The molecular weight of PP-02 was determined in DMF solution to be around 47,000 with polymer dispersity of 3.1. The particle size was determined to be around 220 nm with dispersity of 0.12. The ideal structure of the polymer in PP-02 is shown in FIG. 31, wherein a=0.30, b=0.10, c=0.01, d=0.58, e=0.01, x+z=6, and y=9.

Figure 32:
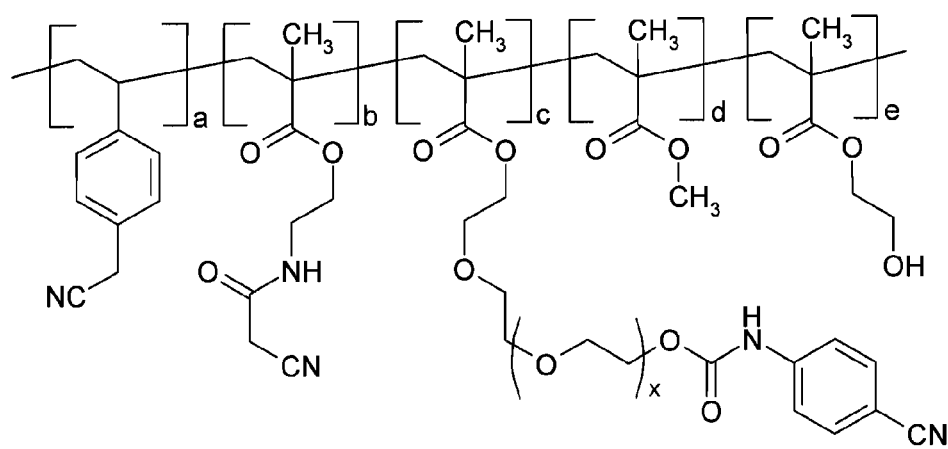
FIG. 32 is the ideal structure of polymeric particle PP-07.

The synthesis of polymeric particle PP-07 was performed similarly to the synthesis of polymeric particle PP-01 except that 4.5 grams of CN-M05 was replaced with 11.8 grams of CN-M07. The molecular weight of PP-03 was determined in DMF solution to be around 38,000 with polymer dispersity of 2.3. The particle size was determined to be around 180 nm with dispersity of 0.10. The ideal structure of the polymer in PP-03 is shown in FIG. 32, wherein a=0.30, b=0.10, c=0.01, d=0.58, e=0.01, and x=25.

Figure 33:
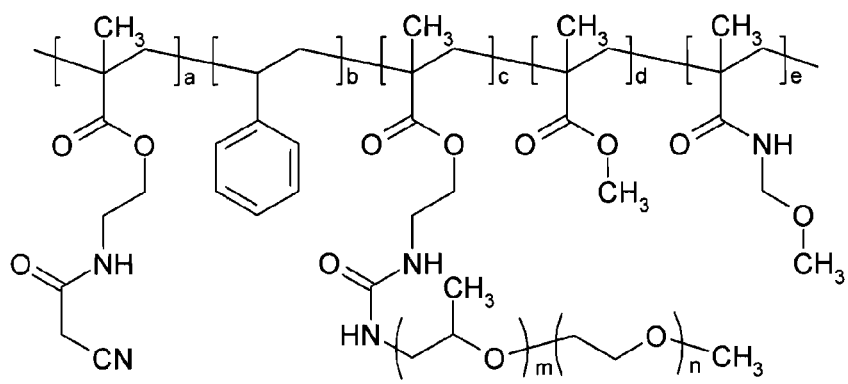
FIG. 33 is the ideal structure of polymeric particle PP-06.

Polymeric particle PP-06 was synthesized by heating a mixture of 95.2 grams of n-propanol and 40.8 grams of de-ionized water in which were dissolved 19.6 grams of CN-M01, 4.50 grams of CN-M05 monomer, 3.10 grams of styrene, 0.85 grams of CN-M04, and 6.70 grams of methyl methacrylate (MMA), in a 1 L 4-neck flask at 75° C. under a nitrogen atmosphere and constant stirring. After heating for 30 minutes, 0.4 g of V59 was added into the reaction mixture. The solution became hazy within 30 minutes of polymerization. After polymerization for 10 hours at 75° C., another 0.5 g of V59 was added into the reaction mixture and the polymerization was continued for another 14 hours. Air was introduced into the reaction mixture and stirring at 75° C. was continued for an additional 2 hours to terminate the polymerization. The molecular weight of PP-06 was determined in tetrahydrofuran solution to be around 32,000 with polymer dispersity of 2.2. The particle size was determined to be around 250 nm with dispersity of 0.15. The solid weight of the PP-06 polymeric particle was adjusted with the mixture of water and IPA (25:75 by weight) to give 20% solid weight. The ideal structure of PP-06 is shown in FIG. 33, wherein a=0.50, b=0.15, c=0.01, d=0.33, e=0.05, m=9, and n=1.

Polymeric particle PP-03 having a general structure as shown below:

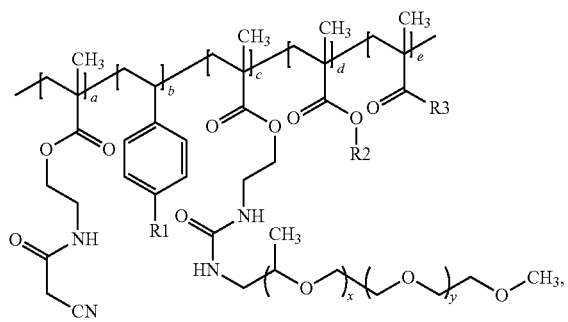

wherein a=0.50 (100 mmoles), b=0.15 (30 mmoles), c=0.02 (4 mmoles), d=0.30 (60 mmoles), e=0.03 (6 mmoles), x=1 and y=9, and wherein R1 is H, R2 is methyl, R3 is —O—C$_2$H$_4$—OH were synthesized by heating a mixture of 46 grams of n-propanol and 107 grams of de-ionized water in which were dissolved with the corresponding monomers in a 1 L 4-neck flask at 75° C. under a nitrogen atmosphere with constant high shear stirring. After heating for 30 minutes, 0.4 g of V59 was added into the reaction mixture. The solution became hazy within 60 minutes of polymerization. After polymerization for 10 hours at 75° C., another 0.5 g of V59 was added into the reaction mixture and the polymerization was continued for another 14 hours. Air was introduced into the reaction mixture and stirring at 75° C. was continued for an additional 2 hours to terminate the polymerization. The molecular weight of the obtained polymeric particles was determined in tetrahydrofuran solution. It was 32,000 g/mol. The particle size was determined in isopropanol-water solution (30-70 w/w %). It was 290 g/mol.

Negative-Working Near Infrared Radiation-Sensitive Lithographic Printing Plates

Printing plates were produced and tested as follows. The coated plates were imaged using Screen PlateRite 8600S platesetter equipped with 830 nm lasers. The imaged plates were mounted on AB Dick duplicator press using black ink (available from Pacific Inks, Vietnam) and fountain solution containing 3.0 parts of MYLAN-FS100 in 97.0 parts of water (available from MyLan Chemicals Inc., Vietnam).

EXAMPLE 25

A coating solution with the following composition was coated on an electro-grained, sulfuric acid anodized aluminum substrate using wire-wound rod and dried at 80° C. with hot air. The obtained coating weight was around 1.0 g/m$^2$.

| Composition | Solid Weight (grams) |
|---|---|
| RGT-01 | 1.00 |
| PP-01 | 4.00 |

| | |
|---|---|
| Tuxedo 600PFB | 4.10 |
| PD08-001 | 0.40 |
| ADS08-008 | 0.40 |
| Blue 63 | 0.10 |

| Solvents | Weight (grams) |
|---|---|
| n-Propanol | 90.0 |
| Water | 10.0 |
| BYK 336 | 0.10 |

The plate was imaged between 100 and 250 mJ/cm² and mounted on the AB Dick press. High quality printing image was obtained on paper after 10 impressions. The plate can be used to print more than 25,000 high-resolution copies. The imaged plate can also be developed off-press using water, WG100 gum solution (available from Agfa, Belgium) or SP200 developer (available from Kodak, USA).

EXAMPLE 26

A coating solution with the following composition was coated on a brush-grained, phosphoric acid anodized aluminum substrate using wire-wound rod and dried at 80° C. with hot air. The obtained coating weight was around 1.0 g/m².

| Composition Solid | Weight (grams) |
|---|---|
| RGT-02 | 1.00 |
| PP-01 | 4.00 |
| Tuxedo 600PFB | 4.10 |
| PD08-001 | 0.40 |
| ADS08-008 | 0.40 |
| Blue 63 | 0.10 |

| Solvents | Weight (grams) |
|---|---|
| n-Propanol | 90.0 |
| Water | 10.0 |
| BYK 336 | 0.10 |

The plate was imaged between 100 and 250 mJ/cm² and mounted on the AB Dick press. High quality printing image was obtained on paper after 10 impressions. The plate can be used to print more than 25,000 high-resolution copies. The imaged plate can also be developed off-press using water, WG100 gum solution (available from Agfa, Belgium) or SP200 developer (available from Kodak, USA).

EXAMPLE 27

A coating solution with the following composition was coated on an electro-grained, sulfuric acid anodized aluminum substrate using wire-wound rod and dried at 80° C. with hot air. The obtained coating weight was around 1.0 g/m².

| Composition | Solid Weight (grams) |
|---|---|
| RGT-03 | 1.00 |
| PP-02 | 4.00 |
| Tuxedo 600PFB | 4.10 |
| PD08-001 | 0.40 |
| ADS08-008 | 0.40 |
| Blue 63 | 0.10 |

| Solvents | Weight (grams) |
|---|---|
| n-Propanol | 90.0 |
| Water | 10.0 |
| BYK 336 | 0.10 |

The plate was imaged between 100 and 250 mJ/cm² and mounted on the AB Dick press. High quality printing image was obtained on paper after 10 impressions. The plate can be used to print more than 25,000 high-resolution copies. The imaged plate can also be developed off-press using water, WG100 gum solution (available from Agfa, Belgium) or SP200 developer (available from Kodak, USA).

EXAMPLE 28

A coating solution with the following composition was coated on an electro-grained, sulfuric acid anodized aluminum substrate using wire-wound rod and dried at 80° C. with hot air. The obtained coating weight was around 1.0 g/m².

| Composition | Solid Weight (grams) |
|---|---|
| RGT-03 | 1.00 |
| PP-07 | 4.00 |
| Tuxedo 600PFB | 4.10 |
| PD08-001 | 0.40 |
| ADS08-008 | 0.40 |
| Blue 63 | 0.10 |

| Solvents | Weight (grams) |
|---|---|
| n-Propanol | 90.0 |
| Water | 10.0 |
| BYK 336 | 0.10 |

The plate was imaged between 100 and 250 mJ/cm² and mounted on the AB Dick press. High quality printing image was obtained on paper after 10 impressions. The plate can be used to print more than 25,000 high-resolution copies. The imaged plate can also be developed off-press using water, WG100 gum solution (available from Agfa, Belgium) or SP200 developer (available from Kodak, USA).

EXAMPLE 29

A coating solution with the following composition was coated on an electro-grained, sulfuric acid anodized aluminum substrate using wire-wound rod and dried at 80° C. with hot air. The obtained coating weight was around 1.0 g/m².

| Composition | Solid Weight (grams) |
|---|---|
| RGT-03 | 1.00 |
| PP-06 | 4.00 |
| Tuxedo 600PFB | 4.10 |
| PD08-001 | 0.40 |
| ADS08-008 | 0.40 |
| Blue 63 | 0.10 |

| Solvents | Weight (grams) |
|---|---|
| n-Propanol | 90.0 |
| Water | 10.0 |
| BYK 336 | 0.10 |

The plate was imaged between 100 and 250 mJ/cm² and mounted on the AB Dick press. High quality printing image was obtained on paper after 10 impressions. The plate can be used to print more than 25,000 high-resolution copies. The imaged plate can also be developed off-press using water, WG100 gum solution (available from Agfa, Belgium) or SP200 developer (available from Kodak, USA).

COMPARATIVE EXAMPLE 1

A coating solution with the following composition was coated on an electro-grained, sulfuric acid anodized aluminum substrate using wire-wound rod and dried at 80° C. with hot air. The obtained coating weight was around 1.0 g/m².

| Composition | Solid Weight (grams) |
|---|---|
| PP-06 | 5.00 |
| Tuxedo 600PFB | 4.10 |
| PD08-001 | 0.40 |
| ADS08-008 | 0.40 |
| Blue 63 | 0.10 |

| Solvents | Weight (grams) |
|---|---|
| n-Propanol | 90.0 |
| Water | 10.0 |
| BYK 336 | 0.10 |

The plate was imaged between 100 and 250 mJ/cm² and mounted on the AB Dick press. High quality printing image was obtained on paper after 10 impressions. The plate can be used to print less than 5,000 high-resolution copies. The imaged plate can also be developed off-press using water, WG100 gum solution (available from Agfa, Belgium) or SP200 developer (available from Kodak, USA).

EXAMPLE 30

A negative working thermal plate was prepared using the following coating solution. It was coated on anodized aluminum substrate using a wire-wound rod on anodized aluminum substrate, then dried with hot air at 80° C. for three minutes to give a coating weight of around 1.0 g/m². The plate was imaged at an energy density between 100 and 200 mJ/cm² and developed using GSN50 aqueous cleaning solution (available from MyLan Chemicals Inc., Travinh, Vietnam) developer using Azura C95 clean out unit at the speed of 500 mm per minute. It produced strong images. The developed plate was mounted on the SpeedMaster 74 press (Heidelberg, Germany) and allowed printing more than 25,000 high resolution copies on paper.

| Ingredients | Solid Weight (grams) |
|---|---|
| Gallo-25X | 0.40 |
| Gallo-Iodonium | 0.12 |
| PP-03 | 0.35 |
| ADS08-008 | 0.04 |
| Klucel E | 0.05 |
| PD08-001 | 0.04 |

| Solvent | Weight (grams) |
|---|---|
| 2-Methoxy propanol | 89.99 |
| Water | 10.00 |
| BYK 307 | 0.001 |

Positive-Working Near Infrared Radiation-Sensitive Lithographic Printing Plates

Coating compositions comprising the gallotannic compounds prepared above were produced by dissolving the coating ingredients in 2-methoxypropanol (Dowanol PM) containing 0.01% BYK 307. The coating solutions were filtered 3 times through a 0.2 μm filter. They were coated using a slot-die coater at the speed of 10 meter per minute on aluminum substrate. The plates were dried at 120° C. for 5 minutes using a hot air oven. The aluminum substrate was electro-grained and anodized with hydrochloric acid and sulfuric acid, respectively. It was then treated with an aqueous solution of NaF/NaH2PO4 at 70° C. to improve its hydrophilicity. The surface roughness (Ra) and oxide weight of the aluminum substrates were around 0.50 and 2.50 g/m², respectively. The coating thickness was adjusted to 1.7 g/m². The coated plates were stored in air conditioned rooms at 25° C. for at-least 10 days before imaging and printing evaluation.

The plates were imaged using a plate-setter (PlateRite 8600S, available from Dinippon Screen, Japan) between 50 and 100% laser power with 2% laser power increment and drum speed 700 RPM. The imaged plates were developed at 23° C. and 30 seconds dwell time using GSP90 developer (available from MyLan Chemicals Inc., Travinh, Vietnam) on a Tung Sung 88 processor.

In the table below,

CE is defined as the correct exposure, which is the required laser power to achieve the same 50% dot on the testing target and on the developed plates.

CP is defined as the clean point, which is the required laser power to have a clean background or 0% dot on the development plates.

CDL is defined as the percent (%) of the coating loss at the non-exposure areas before and after development. The value of CDL was obtained by measuring the cyan optical density at the non-exposure area before and after development with GSP90 developer at 30 seconds dwell time and 22° C.

IPA resistance is tested by dipping the plate in aqueous solution containing 25% by weight of isopropanol at 25° C. until damage was observed on the coating.

The print tests were done using a 4-colors press (Speed Master 74, Heidelberg, Germany). The number of copy was determined at the 10% dot starting to be damaged of peeling off.

EXAMPLES 31-43

| Ingredients (% Solid Weight) | 31 (comparative) | 32 | 33 | 34 | 35 | 36 | 37 | 38 | 39 | 40 | 41 | 42 | 43 |
|---|---|---|---|---|---|---|---|---|---|---|---|---|---|
| MCI08-P020 | 63.0 | 63.0 | 53.0 | 23.0 | 25.0 | 61.0 | 65.0 | 60.0 | 60.0 | 62.0 |  | 48.0 | 68.0 |
| MCI09-P009 | 30.0 |  |  |  |  | 30.0 |  | 30.0 | 30.0 | 20.0 | 25.0 | 20.0 |  |
| MCI09-P052 |  | 30.0 | 30.0 | 30.0 | 30.0 |  |  |  |  |  |  |  |  |
| MCI09-P058 |  |  |  | 30.0 | 30.0 |  |  |  |  |  | 62.0 |  |  |
| MCI09-M090 |  |  |  |  |  |  |  | 3.00 |  |  |  |  |  |
| MCI09-D001 |  |  |  |  |  |  |  |  | 3.00 | 3.00 |  |  |  |
| LB9900 | 2.00 | 2.00 | 2.00 | 2.00 | 2.00 | 2.00 | 2.00 | 2.00 | 2.00 | 2.00 | 2.00 | 2.00 | 2.00 |
| Basic Green 4 | 3.00 | 3.00 | 3.00 | 3.00 | 3.00 | 3.00 | 3.00 | 3.00 | 3.00 | 3.00 | 3.00 | 3.00 | 3.00 |
| ADS775PI | 0.50 | 0.50 |  | 0.50 |  |  |  | 0.50 | 0.50 |  | 3.00 | 3.00 | 3.00 |
| ADS830AT | 1.50 | 1.50 |  | 1.50 |  |  |  | 1.50 | 1.50 |  |  |  |  |
| Thermolak ® 8020 |  |  | 10.0 |  | 10.0 |  |  |  |  |  | 10.0 | 10.0 |  |
| MCI09-M100 |  |  |  |  |  | 4.00 |  |  |  |  |  |  |  |
| MCI09-P200 |  |  |  |  |  |  | 30.0 |  |  |  |  |  |  |
| MCI09-P202 |  |  |  |  |  |  |  |  |  |  |  | 27.0 |  |
| MCI09-P208 |  |  |  |  |  |  |  |  |  |  |  |  | 27.0 |
| Plate Evaluation | | | | | | | | | | | | | |
| IPA resistant (Hours) | <4 * | <30 | <48 | <48 | >48 | >48 | >48 | >48 | >48 | >48 | >48 | >48 | >48 |
| CE (% Laser Power) | 90 | 90 | 90 | 94 | 94 | 88 | 94 | 88 | 88 | 88 | 94 | 90 | 92 |
| CP (% Laser Power) | 74 | 74 | 74 | 74 | 74 | 70 | 74 | 70 | 70 | 70 | 82 | 80 | 80 |
| CDL (%) | 6.70 | 4.60 | 4.15 | 2.23 | 2.45 | 2.17 | 2.04 | 2.04 | 2.04 | 2.04 | 2.23 | 2.17 | 2.04 |
| Print Length × 1,000 (Number of copies) | <11 | <150 | >200 | >200 | >200 | >200 | <150 | <180 | >200 | >200 | >200 | >200 | >200 |

* Delaminating due to poor adhesion to the substrate

EXAMPLES 44-47

Positive Plates Using Unmodified Gallotannin

| Ingredient (% solid weight) | 44 | 45 | 46 (comparative) | 47 (comparative) |
|---|---|---|---|---|
| MCI08-P020 | 62.5 | 61.5 | 59.5 | 57.5 |
| MCI09-P009 | 30.0 | 30.0 | 30.0 | 30.0 |
| Gallotannin | 1.00 | 2.00 | 4.00 | 6.00 |
| LB9900 | 2.00 | 2.00 | 2.00 | 2.00 |
| Basic Green 4 | 3.00 | 3.00 | 3.00 | 3.00 |
| ADS775PI | 0.40 | 0.40 | 0.40 | 0.40 |
| ADS830AT | 1.10 | 1.10 | 1.10 | 1.10 |
| Plate Evaluation | | | | |
| IPA Resistant (Hours) | <8 | <24 | <4 | <1 |
| CE (% Laser Power) | 90 | 90 | 82 | 74 |
| CP (% Laser Power) | 60 | 70 | 60 | 60 |
| CDL (%) | 11.0 | 8.0 | 31.0 | 60.0 |

Negative Working UV Sensitive Lithographic Printing Plate

EXAMPLE 48

A negative working UV sensitive lithographic printing plate comprising Gallo-Triazine as prepared above was prepared with the following composition:

| Ingredients | Solid Weight (grams) |
|---|---|
| PP-03 | 0.30 |
| Gallo-25X | 0.50 |
| Gallo-triazine | 0.11 |
| Klucel E | 0.05 |
| PD08-001 | 0.04 |

| Solvents | Weight (grams) |
|---|---|
| 2-Methoxy propanol | 89.99 |
| Water | 10.00 |
| BYK 307 | 0.001 |

This composition was coated on an anodized aluminum substrate using wire-wound rod and dried using hot air at 90° C. to give a coating weight around 1.0 gram/m². The plate was imaged on the XPose! 230 UV platesetter (available from Luscher, Switzerland) at the energy density between 10 and 50 mJ/cm². The imaged plate was then developed with GSN50 aqueous cleaning solution (available from MyLan Chemicals Inc., Travinh, Vietnam) developer using Azura C95 clean out unit at the speed of 500 mm per minute to give high resolution image with clean background. The developed plate was mounted on the SpeedMaster 74 press (Heidelberg, Germany) to provide more than 20,000 high resolution printing copies.

Positive Working UV Sensitive Lithographic Printing Plate

EXAMPLE 49

A positive working UV sensitive lithographic printing plate comprising Gallo-NQD was prepared with the following composition:

| Ingredients | Solid Weight (grams) |
| --- | --- |
| Novolak Resin 7525 | 7.55 |
| Gallo-NQD | 2.00 |
| CAP | 0.20 |
| Basic violet 3 | 0.20 |
| Solvents | Weight (grams) |
| 2-Methoxy propanol | 90.0 |
| BYK 307 | 0.05 |

This coating composition was coated on an anodized aluminum substrate using wire-wound rod and dried using hot air at 90° C. to give a coating weight around 1.5 grams/m². The plate was imaged on the XPose! 230 UV platesetter (available from Luscher, Switzerland) at the energy density between 80 and 200 mJ/cm². The imaged plate was then developed with GSP90 developer using Tung Sung 88 processor at 30 seconds dwell time to give high resolution image with clean background. The developed plate was mounted on the SpeedMaster 74 press (Heidelberg, Germany) to provide more than 100,000 high resolution printing copies.

Although the present invention has been described hereinabove by way of specific embodiments thereof, it can be modified, without departing from the spirit and nature of the subject invention as defined in the appended claims.

References

The present description refers to a number of documents, the content of which is herein incorporated by reference in their entirety

| European Patents: |
| --- |
| 0 438 123 |
| 0 770 495 |
| 0 823 327 |
| 0 909 657 |
| 1 182 033 |

| US patents: |
| --- |
| 4,565,769 |
| 5,208,135 |
| 5,569,573 |
| 5,629,354 |
| 6,124,425 |
| 6,177,182 |
| 6,255,033 |
| 6,261,740 |
| 6,420,087 |
| 6,461,795 |
| 6,541,181 |
| 6,506,536 |
| 6,562,543 |
| 6,569,603 |
| 6,582,882 |
| 6,613,494 |
| 6,787,281 |
| 6,846,614 |
| 6,899,994 |
| 6,902,860 |
| 6,960,422 |
| 6,969,575 |
| 6,983,694 |
| 7,001,704 |
| 7,083,895 |
| 7,135,271 |
| 7,261,998 |
| 7,473,515 |
| 7,544,462 |

| U.S. patent applications: |
| --- |
| 2003/0064318 |
| 2005/0123853 |
| 2007/0269739 |
| 2007/0808434 |
| 2008/0171286 |
| 2009/0004599 |
| 2009/0035694 |
| 2009/0111051 |
| 2009/0186299 |

| PCT Applications: |
| --- |
| WO 97/39894 |
| WO 98/42507 |
| WO 99/11458 |
| WO 2004/020484- |
| WO 2004/101280 |
| WO 2008/156552 |

| Non-patent References: |
| --- |
| Chemical Review, 1997, 97, pp. 1681-1712 |
| Chemical Review, 2001, 101, pp. 4071-4097 |

The invention claimed is:
1. A gallotannic compound comprising gallotannin:

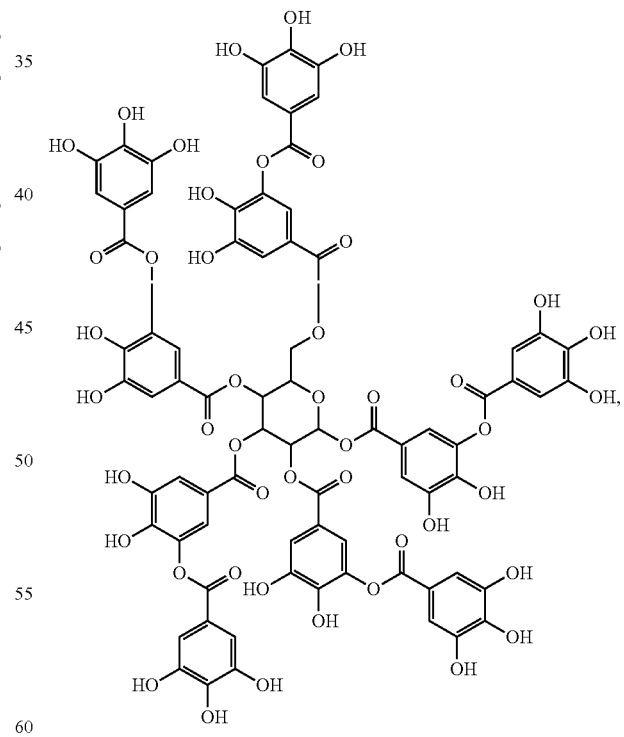

wherein at least one hydroxyl group is replaced by a substituent comprising:
a) a molecule, oligomer or polymer used in lithographic printing plate coatings, and wherein the molecule, oligomer or polymer is a crosslinker comprising a functional group capable of undergoing a crosslinking reaction via radical polymerization, an initiator, an adhesion promoter, or a NIR- or UV-sensitive chromophore, or b) another gallotannic compound comprising gallotannin wherein at least one hydroxyl group in said gallotannin is replaced by a substituent comprising a molecule, oligomer or polymer as defined in a).

2. The gallotannic compound of claim 1, wherein more than one hydroxyl group of gallotannin is replaced by said substituents, wherein the substituents replacing each of the hydroxyl groups are the same or different from each other.

3. The gallotannic compound of claim 1, wherein the substituent(s) is/are attached directly to the gallotannin.

4. The gallotannic compound of claim 1, wherein the substituent(s) is/are attached to the gallotannin through a linking group.

5. The gallotannic compound of claim 4, wherein the linking group is alkyl optionally comprising one or more ester, ether, amine, amido, urea, carbamate, sulfonamide, or

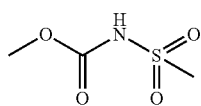

functional group.

6. The gallotannic compound of claim 1, wherein the gallotannic compound is of formula

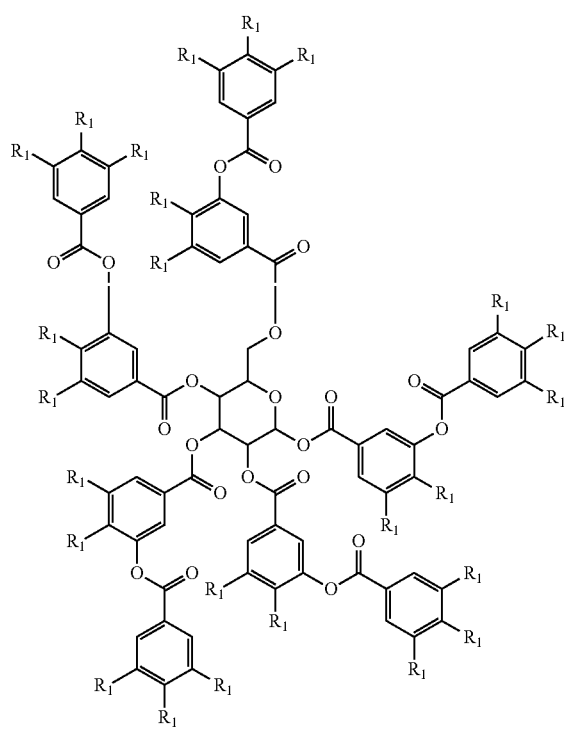

wherein each $R_1$ independently is hydroxyl or comprises one or more of:
a) said crosslinker,
b) said initiator,
c) said adhesion promoter,
d) said chromophore, or
e) said other gallotannic compound,
and optionally comprises a linking group,
with the proviso that at least one $R_1$ is not hydroxyl.

7. The gallotannic compound of claim 1, wherein the substituent comprises said crosslinker.

8. The gallotannic compound of claim 7, wherein the functional group capable of undergoing a crosslinking reaction via radical polymerization is acrylate, methacrylate, acrylamide, methacrylamide, alkylacrylate, alkylmethacrylate, alkylacrylamide, alkylmethacrylamide, vinyl ether, allyl, or styryl.

9. A method of producing a gallotannic compound, the method comprising the step of:

a) providing gallotannin:

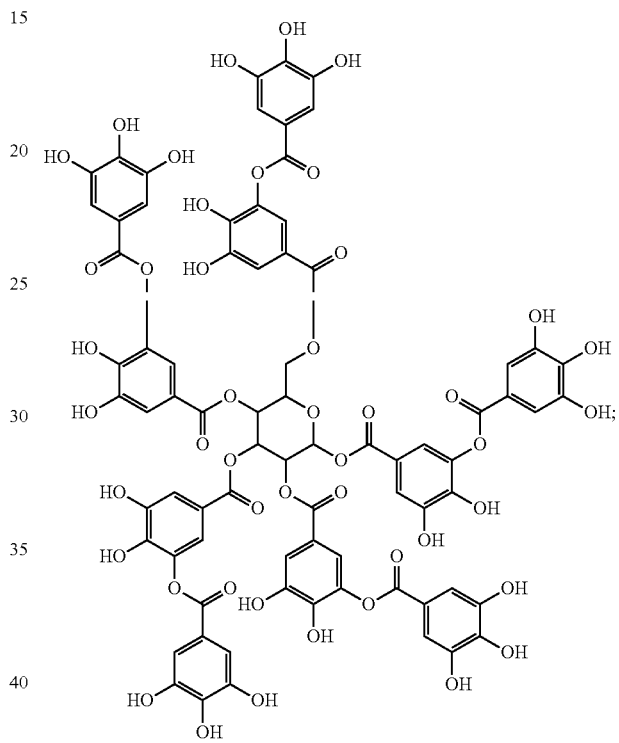

and b) replacing at least one hydroxyl group of the gallotannin with a substituent, wherein the substituent is as described in claim 1.

10. The gallotannic compound of claim 1 being comprised in a printing plate coating composition.

11. The gallotannic compound of claim 10, wherein said coating composition comprises between about 1 and about 40 w/w % of said gallotannic compound.

12. The gallotannic compound of claim 1 being comprised in a lithographic printing plate.

13. The gallotannic compound of claim 1, wherein the substituent comprises said initiator.

14. The gallotannic compound of claim 1, wherein the substituent comprises said adhesion promoter.

15. The gallotannic compound of claim 1, wherein the substituent comprises said chromophore.

16. The gallotannic compound of claim 14, wherein the adhesion promoter comprises one or more cyano, ureido or phosphoric acid functional groups.

17. A gallotannic compound comprising gallotannin:

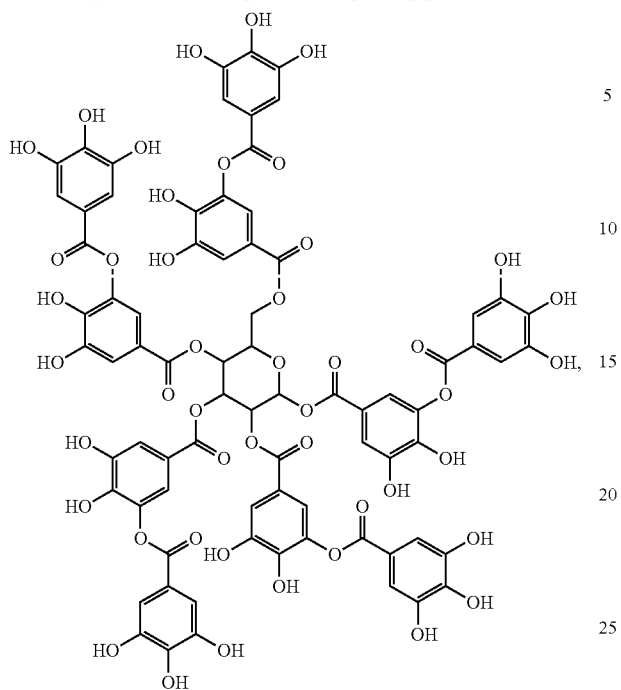

wherein at least one hydroxyl group is replaced by a substituent comprising:

a) a molecule, oligomer or polymer used in lithographic printing plate coatings, and wherein the molecule, oligomer or polymer is a crosslinker comprising a functional group capable of undergoing a crosslinking reaction via radical polymerization, or an initiator, or an adhesion promoter, or b) another gallotannic compound comprising gallotannin wherein at least one hydroxyl group in said gallotannin is replaced by a substituent comprising a molecule, oligomer or polymer as defined in a).

18. The gallotannic compound of claim 17 wherein the functional group capable of undergoing a crosslinking reaction via radical polymerization is acrylate, methacrylate, acrylamide, methacrylamide, alkylacrylate, alkylmethacrylate, alkylacrylamide, alkylmethacrylamide, vinyl ether, allyl, or styryl.

19. The gallotannic compound of claim 17, wherein the adhesion promoter comprises one or more cyano, ureido or phosphoric acid functional groups.

* * * * *